(12) United States Patent
Aboytes et al.

(10) Patent No.: US 11,376,012 B2
(45) Date of Patent: **\*Jul. 5, 2022**

(54) DEVICES, SYSTEMS, AND METHODS FOR TREATMENT OF VASCULAR DEFECTS

(71) Applicant: Covidien LP, Mansfield, MA (US)

(72) Inventors: Maria Aboytes, Palo Alto, CA (US);
Arturo Rosqueta, San Jose, CA (US);
Erik Engelson, Menlo Park, CA (US);
Scott Wilson, Palo Alto, CA (US)

(73) Assignee: COVIDIEN LP, Mansfield, MA (US)

( * ) Notice: Subject to any disclaimer, the term of this patent is extended or adjusted under 35 U.S.C. 154(b) by 253 days.

This patent is subject to a terminal disclaimer.

(21) Appl. No.: 16/526,706

(22) Filed: Jul. 30, 2019

(65) Prior Publication Data
US 2019/0350590 A1    Nov. 21, 2019

Related U.S. Application Data

(63) Continuation of application No. 15/228,278, filed on Aug. 4, 2016, now Pat. No. 10,478,195.

(51) Int. Cl.
*A61B 17/12* (2006.01)
*A61B 17/00* (2006.01)

(52) U.S. Cl.
CPC .. *A61B 17/12172* (2013.01); *A61B 17/12113* (2013.01); *A61B 2017/00867* (2013.01)

(58) Field of Classification Search
CPC ........ A61B 17/12113; A61B 17/12163; A61B 17/12168; A61B 17/12172
See application file for complete search history.

(56) References Cited

U.S. PATENT DOCUMENTS 833,783 A    10/1906  Hall
5,250,071 A  10/1993  Palermo
(Continued)

FOREIGN PATENT DOCUMENTS

CA    2812012 A1    3/2012
DE    102011102933 A1    12/2012
(Continued)

OTHER PUBLICATIONS

International Search Report and Written Opinion dated Oct. 18, 2017; International Application No. PCT/US2017/041905; 12 pages.
(Continued)

*Primary Examiner* — Thomas McEvoy
(74) *Attorney, Agent, or Firm* — Fortem IP LLP; Mary Fox

(57) ABSTRACT

Devices, systems, and methods for treating vascular defects are disclosed herein. One aspect of the present technology, for example, is directed toward an occlusion device that includes a proximal portion, a distal portion, and an intermediate portion extending between the proximal portion and the distal portion. The distal portion can include a directing region and a lead-in member that extends distally from the directing region. When the occlusion device is in a deployed configuration, the intermediate portion can form a preset bend in the occlusion device that positions the directing region at an angle with respect to the proximal portion. As a result, as the occlusion device is pushed distally out of a delivery catheter into the aneurysm, the directing region directs the distal portion away from exiting the aneurysm through the neck such that the proximal portion crosses the neck and generally remains within the aneurysm.

18 Claims, 32 Drawing Sheets

(56) References Cited

U.S. PATENT DOCUMENTS

| | | |
|---|---|---|
| 5,354,295 A | 10/1994 | Guglielmi et al. |
| 5,645,558 A | 7/1997 | Horton et al. |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid et al. |
| 5,749,891 A | 5/1998 | Ken et al. |
| 5,749,919 A | 5/1998 | Blanc |
| 5,814,062 A | 9/1998 | Sepetka et al. |
| 5,911,731 A | 6/1999 | Pham et al. |
| 5,916,235 A | 6/1999 | Guido |
| 5,925,060 A | 7/1999 | Forber |
| 5,928,260 A | 7/1999 | Chin et al. |
| 5,935,148 A | 8/1999 | Millar et al. |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran et al. |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,059,812 A | 5/2000 | Clerc et al. |
| 6,063,070 A | 5/2000 | Eder |
| 6,063,104 A | 5/2000 | Villar |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz et al. |
| 6,139,564 A | 10/2000 | Teoh |
| 6,152,144 A | 11/2000 | Lesh et al. |
| 6,159,531 A | 12/2000 | Dang et al. |
| 6,168,615 B1 | 1/2001 | Ken et al. |
| 6,168,622 B1 | 1/2001 | Mazzocchi |
| 6,309,367 B1 | 10/2001 | Boock |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz et al. |
| 6,371,980 B1 | 4/2002 | Rudakov et al. |
| 6,375,668 B1 | 4/2002 | Gifford et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,602,261 B2 | 8/2003 | Greene et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,486 B2 | 2/2004 | Ho et al. |
| 6,730,108 B2 | 5/2004 | Van Tassel et al. |
| 6,746,468 B1 | 6/2004 | Sepetka |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,905,503 B2 | 6/2005 | Gifford, III et al. |
| 6,936,055 B1 | 8/2005 | Ken et al. |
| 6,991,617 B2 | 1/2006 | Hektner et al. |
| 6,994,092 B2 | 2/2006 | Van Der Burg et al. |
| 6,994,717 B2 | 2/2006 | Kónya et al. |
| 7,011,671 B2 | 3/2006 | Welch |
| 7,029,487 B2 | 4/2006 | Green, Jr. et al. |
| 7,083,632 B2 | 8/2006 | Avellanet et al. |
| 7,128,073 B1 | 10/2006 | Van Der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,326,225 B2 | 2/2008 | Ferrera et al. |
| 7,331,980 B2 | 2/2008 | Dubrul et al. |
| 7,419,503 B2 | 9/2008 | Pulnev et al. |
| 7,597,704 B2 | 10/2009 | Frazier et al. |
| 7,601,160 B2 | 10/2009 | Richter |
| 7,708,754 B2 | 5/2010 | Balgobin et al. |
| RE42,625 E | 8/2011 | Guglielmi |
| 8,043,326 B2 | 10/2011 | Hancock et al. |
| 8,142,456 B2 | 3/2012 | Rosqueta et al. |
| 8,211,160 B2 | 7/2012 | Garrison et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,425,541 B2 | 4/2013 | Masters et al. |
| 8,470,013 B2 | 6/2013 | Duggal et al. |
| 8,715,317 B1 | 5/2014 | Janardhan et al. |
| 8,834,515 B2 | 9/2014 | Win et al. |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,844,382 B2 | 12/2017 | Aboytes et al. |
| 9,855,051 B2 | 1/2018 | Aboytes et al. |
| 9,907,684 B2 | 3/2018 | Connor et al. |
| 9,962,146 B2 | 5/2018 | Hebert et al. |
| 10,028,745 B2 | 7/2018 | Morsi |
| 2001/0000797 A1 | 5/2001 | Mazzocchi |
| 2001/0001835 A1 | 5/2001 | Greene et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2004/0172056 A1 | 9/2004 | Guterman et al. |
| 2005/0085836 A1 | 4/2005 | Raymond |
| 2005/0222580 A1 | 10/2005 | Gifford et al. |
| 2005/0267511 A1 | 12/2005 | Marks et al. |
| 2005/0277978 A1 | 12/2005 | Greenhalgh |
| 2006/0034883 A1 | 2/2006 | Dang |
| 2006/0052816 A1 | 3/2006 | Bates et al. |
| 2006/0064151 A1 | 3/2006 | Guterman et al. |
| 2006/0089618 A1 | 4/2006 | McFerran et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |

(56) References Cited

U.S. PATENT DOCUMENTS

| | | |
|---|---|---|
| 2006/0155323 A1 | 7/2006 | Porter et al. |
| 2006/0190025 A1 | 8/2006 | Lehe et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito |
| 2007/0010850 A1 | 1/2007 | Balgobin et al. |
| 2007/0083226 A1 | 4/2007 | Buiser et al. |
| 2007/0100426 A1 | 5/2007 | Rudakov et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179520 A1 | 8/2007 | West et al. |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer |
| 2007/0191924 A1 | 8/2007 | Rudakov |
| 2007/0219619 A1 | 9/2007 | Dieck et al. |
| 2007/0276426 A1 | 11/2007 | Euteneuer et al. |
| 2007/0276427 A1 | 11/2007 | Euteneuer et al. |
| 2007/0282373 A1 | 12/2007 | Ashby et al. |
| 2007/0288083 A1 | 12/2007 | Hines |
| 2008/0082176 A1 | 4/2008 | Slazas |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0200945 A1 | 8/2008 | Amplatz et al. |
| 2008/0200979 A1 | 8/2008 | Dieck et al. |
| 2008/0221600 A1 | 9/2008 | Dieck et al. |
| 2008/0281350 A1 | 11/2008 | Sepetka et al. |
| 2009/0043375 A1 | 2/2009 | Rudakov et al. |
| 2009/0062841 A1 | 3/2009 | Amplatz et al. |
| 2009/0062899 A1 | 3/2009 | Dang et al. |
| 2009/0112251 A1 | 4/2009 | Qian et al. |
| 2009/0187214 A1 | 7/2009 | Amplatz et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0297582 A1 | 12/2009 | Meyer et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0139465 A1 | 6/2010 | Christian et al. |
| 2010/0144895 A1 | 6/2010 | Porter |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | Debeer et al. |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283769 A1 | 11/2012 | Cruise et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0116722 A1 | 5/2013 | Aboytes et al. |
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0316012 A1 | 10/2014 | Freyman et al. |
| 2014/0371734 A1 | 12/2014 | Truckai |
| 2015/0216684 A1 | 8/2015 | Enzmann et al. |
| 2015/0250628 A1 | 9/2015 | Monstadt et al. |
| 2015/0272590 A1 | 10/2015 | Aboytes et al. |
| 2015/0313737 A1 | 11/2015 | Tippett et al. |
| 2015/0327843 A1 | 11/2015 | Garrison |
| 2015/0342613 A1 | 12/2015 | Aboytes et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0262766 A1 | 9/2016 | Aboytes et al. |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0036012 A1 | 2/2018 | Aboytes et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2019/0350590 A1 | 11/2019 | Aboytes et al. |

FOREIGN PATENT DOCUMENTS

| | | |
|---|---|---|
| EP | 0717969 A2 | 6/1996 |
| EP | 1295563 A1 | 3/2003 |
| EP | 1813213 A2 | 8/2007 |
| EP | 2208483 A1 | 7/2010 |
| EP | 2609888 A1 | 7/2013 |
| EP | 2932921 A1 | 10/2015 |
| FR | 2890306 A1 | 3/2007 |
| JP | 2005261951 A | 9/2005 |
| JP | 2008521492 A | 6/2008 |
| JP | 2010523260 | 7/2010 |
| JP | 2013027592 A | 2/2013 |
| WO | 9406502 A2 | 3/1994 |
| WO | 9409705 A1 | 5/1994 |
| WO | 9907294 A1 | 2/1999 |
| WO | 9929260 A2 | 6/1999 |
| WO | 0164112 A1 | 9/2001 |
| WO | 02054980 A2 | 7/2002 |
| WO | 02089863 A1 | 11/2002 |
| WO | 2005099634 A1 | 10/2005 |
| WO | 2006034149 A2 | 3/2006 |
| WO | 2007121405 A2 | 10/2007 |
| WO | 2008036156 A1 | 3/2008 |
| WO | 2008074027 A1 | 9/2008 |
| WO | 2009014528 | 1/2009 |

(56) References Cited

FOREIGN PATENT DOCUMENTS

| WO | 2010009019 A1 | 1/2010 |
|---|---|---|
| WO | 2010027363 A1 | 3/2010 |
| WO | 2010077599 A1 | 7/2010 |
| WO | 2011066962 A1 | 6/2011 |
| WO | 2011095966 A1 | 8/2011 |
| WO | 2012034135 A1 | 3/2012 |
| WO | 2013112944 A1 | 8/2013 |
| WO | 2013138615 A2 | 9/2013 |
| WO | 2014105932 A1 | 7/2014 |
| WO | 2013138615 A3 | 9/2014 |
| WO | 2017074411 A1 | 5/2017 |
| WO | 2018051187 A1 | 3/2018 |

OTHER PUBLICATIONS

International Search Report and Written Opinion for International Application No. PCT/US2013/077767, dated Mar. 19, 2014, 9 pages.
International Search Report and Written Opinion for International Application No. PCT/US2013/031466, dated Jun. 25, 2014, 11 pages.
International Search Report and Written Opinion for International Application No. PCT/US11/51268, dated Jan. 2, 2012, 10 pages.
Extended European Search Report dated Jan. 7, 2015 in European Patent Application No. 11824250.2, 7 pages.
Extended European Search Report dated Jul. 1, 2016 in European Patent Application No. 13867906.3; 9 pages.
Extended European Search Report dated Mar. 2, 2016 in European Patent Application No. 137616710.0; 13 pages.
Extended European Search Report dated Jan. 30, 2017 in European Patent Application No. 16190494.1; 9 pages.

DEVICES, SYSTEMS, AND METHODS FOR TREATMENT OF VASCULAR DEFECTS

CROSS-REFERENCE TO RELATED APPLICATION

This application is a continuation of U.S. patent application Ser. No. 15/228,278, filed Aug. 4, 2016, which is incorporated herein by reference in its entirety.

TECHNICAL FIELD

The present technology is directed generally to devices, systems, and methods for the treatment of vascular defects.

BACKGROUND

Aneurysms are blood-filled dilations of a blood vessel generally caused by disease or weakening of the blood vessel wall. The wall of the aneurysm may progressively thin, which increases the risk of rupture causing hemorrhagic stroke or even sudden death. There are about 30,000 to 40,000 cases of aneurysmal rupture per year in the United States, accounting for about 5% of all strokes. The prognosis after aneurysmal rupture is poor; the 30-day mortality rate is approximately 45% and a positive functional outcome is achieved in only 40-50% of survivors. Traditional approaches to preventing aneurysmal rupture often include packing the aneurysm with metal coils to reduce the inflow of blood to the aneurysm and prevent further enlargement and rupture. Such coils are often referred to as "embolic coils" or "microcoils," and can be categorized into the following three groups based on their structural properties: framing coils, filling coils, and finishing coils. Framing coils are inserted first into the aneurysm and form the base structure into which the later-delivered filling coils are packed. As such, framing coils are stiffer than filling and finishing coils to provide structural stability and generally have a complex or three-dimensional shape for approximating the periphery of the aneurysm. Filling coils, in contrast, are softer than framing coils, and multiple filling coils are packed within the framework of the framing coil(s) to achieve a high packing density. Finishing coils are delivered last to fill any remaining gaps left between filling coils.

Embolic coils, however, have several drawbacks. First, embolic coils generally only achieve a 20-40% packing density (i.e., ratio of the volume of the coils inserted into the aneurysm sac and the volume of the aneurysm sac). As a result, blood continues to flow into the aneurysm (also known as recanalization) in about 30% of coil cases, which can cause further swelling of the aneurysm over time. In addition, because the coils must be very small to fit within a microcatheter for delivery through the tiny cranial vessels, numerous coils are often required to adequately fill the aneurysm. These numerous coils must be delivered one-by-one, thereby increasing procedure time and complexity. Yet another drawback is that embolic coils cannot accommodate the wide range of aneurysm shapes and sizes. Embolic coils, for example, are difficult to stabilize within wide-necked aneurysms, which can result in migration of one or more coils across the neck such that a portion of the migrated coil(s) protrudes into the parent blood vessel. The protruding portion of the migrated coil(s) can be a nidus for thromboembolism, which can be fatal if left unaddressed. To address this shortcoming, many existing treatments include positioning an intracranial stent across the neck of the aneurysm to prevent all or part of a coil from migrating across the neck. However, intracranial stents can also be a nidus for thromboembolism, and further increase procedure time and cost. Thus, there is a need for improved devices, systems, and methods for treating aneurysms.

SUMMARY

Figure 1:
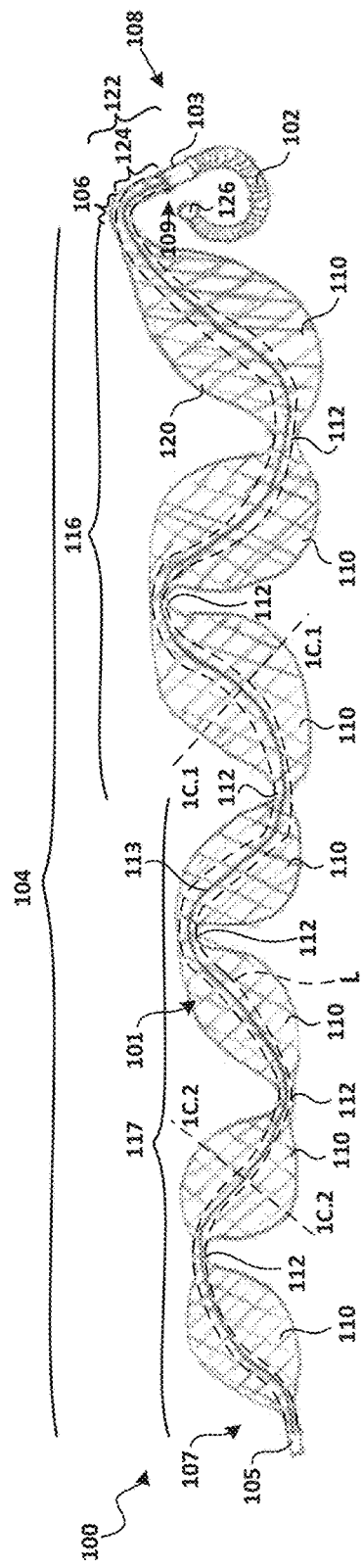
FIG. 1A is an isometric view of an occlusion device in a deployed configuration in accordance with an embodiment of the present technology.
FIG. 1B is a top view of the occlusion device shown in FIG. 1A, unfurled and held in an elongated configuration.
FIG. 1C is a schematic illustration showing cross-sections of the occlusion device at different locations along the longitudinal axis of the occlusion device.

An aspect of at least some of the embodiments disclosed herein involves an occlusion device having a preset bend at its distal portion that positions a directing region of the occlusion device at an angle with respect to a proximal portion of the occlusion device. As the occlusion device is pushed distally out of a delivery catheter (e.g., a microcatheter) into an aneurysm, the directing region positions the distal portion such that the proximal portion generally remains within the aneurysm.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 8, 22, 32, 40, 47, 56, 65, or 69. The other clauses can be presented in a similar manner.

1. A vascular occlusion device for treating an aneurysm, wherein a neck of the aneurysm opens to a blood vessel, the device comprising:
    a proximal portion having a mesh configured to be positioned within the aneurysm;
    a distal portion including a directing region having:
        a proximal terminus that coincides with a proximal terminus of the distal portion,
        a distal terminus, wherein the directing region extends along a first direction that runs through the proximal terminus and the distal terminus, and
        a length measured along the first longitudinal direction between the proximal terminus and the distal terminus; and
    an intermediate portion between the proximal and distal portions that, when in a deployed configuration, forms a preset bend in the device that orients the first longitudinal direction of the directing region at an angle to a portion of the proximal portion adjacent the intermediate portion, and
    wherein, when the device is being pushed distally out of a delivery catheter into the aneurysm, the directing region directs the distal portion to inhibit the distal portion from exiting the aneurysm through the neck such that the proximal portion crosses the neck and generally remains within the aneurysm.

2. The device of Clause 1 wherein the directing region includes an elongated, generally cylindrical portion of the mesh.

3. The device of Clause 1 wherein:
    the intermediate portion includes a portion of the mesh having a preset, curved shape; and
    the directing region includes an elongated, generally cylindrical portion of the mesh.

4. The device of any one of Clauses 1-3 wherein the directing region has a generally linear shape.

5. The device of any one of Clauses 1-4 wherein the proximal portion has a second longitudinal direction immediately adjacent the intermediate portion, and wherein the angle is between the first longitudinal direction of the directing region and the second longitudinal direction of the proximal portion.

6. The device of any one of Clauses 1-5 wherein the mesh is a braid.

7. The device of any one of Clauses 1-6 wherein the length of the directing region is from about 25% to about 75% of a diameter of the aneurysm.

8. The device of any one of Clauses 1-7 wherein the length of the directing region is between about 0.05 inches and about 0.20 inches.

9. The device of any one of Clauses 1-7 wherein the length of the directing region is between about 0.021 inches and about 0.20 inches.

10. The device of any one of Clauses 1-7 wherein the length of the directing region is between about 0.021 inches and about 0.18 inches.

11. The device of any one of Clauses 1-10 wherein the angle is between about 45 degrees and about 135 degrees.

12. The device of any one of Clauses 1-10 wherein the angle is between about 65 degrees and about 115 degrees.

13. The device of any one of Clauses 1-10 wherein the angle is between about 70 degrees and about 110 degrees.

14. The device of Clause 1 wherein the angle is between about 80 degrees and about 105 degrees.

15. A vascular occlusion device for treating an aneurysm, wherein a neck of the aneurysm opens to a blood vessel, the device comprising:
an expandable mesh having an elongated configuration and a deployed configuration, wherein, in the deployed configuration, the mesh includes:
a proximal portion formed of a flattened tubular braid configured to contact and conform to an inner surface of the aneurysm,
a radially compacted distal portion,
an intermediate portion extending between the proximal portion and the distal portion, wherein the intermediate portion is curved such that the distal portion is positioned at a predetermined angle with respect to the proximal portion; and
a directing region at the distal portion of the expandable mesh having a proximal terminus and a distal terminus, wherein the directing region extends along a first longitudinal direction that runs through the proximal terminus and the distal terminus, and wherein the directing region is positioned at an angle relative to the proximal portion between about 45 degrees and about 135 degrees, and
wherein, when the device is being pushed distally out of a delivery catheter into the aneurysm, the directing region directs the distal portion to inhibit the distal portion from exiting the aneurysm through the neck such that the proximal portion crosses the neck and generally remains within the aneurysm.

16. The device of Clause 15 wherein the directing region includes an elongated, generally cylindrical portion of the mesh.

17. The device of Clause 15 or Clause 16 wherein the directing region has a generally linear shape.

18. The device of any one of Clauses 15-17 wherein the proximal portion of the mesh forms a predetermined three-dimensional structure when the mesh is in a deployed configuration.

19. The device of any one of Clauses 15-18 wherein the proximal portion of the mesh forms a plurality of curved, broad portions that together form a three-dimensional spherical structure when the mesh is in the deployed configuration.

20. The device of any one of Clauses 15-19 wherein, when the mesh is in the deployed configuration, the proximal portion of the mesh forms (1) a first plurality of concave, broad portions that together form a first three-dimensional structure, and (2) a second plurality of concave, broad portions that together form a second three-dimensional structure that is configured to be deployed within an interior region defined by the first three-dimensional structure.

DETAILED DESCRIPTION

The present technology is directed generally to devices, systems, and methods for the treatment of vascular defects, and in particular, to vascular occlusion devices for treating hemorrhagic stroke. Unlike conventional devices, the occlusion device of the present technology is deliverable through a microcatheter, self-anchors within the aneurysm, and provides improved neck coverage. In one embodiment, the present technology includes an expandable occlusion device having a proximal portion, a distal portion, and an intermediate portion extending between the proximal portion and the distal portion. The distal portion of the occlusion device can include an elongated directing region and a lead-in member that extends distally from the directing region. The directing region can have a length that is about 25% to about 75% of a diameter of the targeted aneurysm. In operation, as the occlusion device is initially deployed from the delivery catheter, the intermediate portion forms a preset bend in the occlusion device that positions the directing region at an angle with respect to the proximal portion. As the occlusion device is pushed further distally out of a delivery catheter (e.g., a microcatheter) into the aneurysm, the directing region positions the distal portion such that the proximal portion generally remains within the aneurysm. For example, the directing region can direct the distal portion to consistently span across or even away from the neck of the aneurysm.

As used herein, the terms "distal" and "proximal," unless otherwise specified, refer to a position of the occlusion device and/or portions of the occlusion device relative to an operator along a longitudinal axis of the occlusion device, and/or a position of associated delivery components (or portions thereof) relative to an operator along a longitudinal axis of the relevant delivery component.

1.0 OVERVIEW

FIG. 1A is an isometric view of an occlusion device 100 in accordance with the present technology shown in a deployed (e.g., unsheathed) configuration in which it is not constrained (e.g., relaxed). FIG. 1B is a top view of the occlusion device 100 after being unfurled from the deployed, relaxed configuration shown in FIG. 1A and held in an unfurled, elongated configuration to provide a better view of the entire length of the occlusion device 100. As shown in FIGS. 1A and 1B, the occlusion device 100 includes a mesh 101, a lead-in member 102, a proximal connector 105 (FIG. 1B), and a distal connector 103 coupling the lead-in member 102 to the mesh 101. The mesh 101 is formed of a superelastic and/or shape memory material. The properties of these materials allow the device to deform and be constrained within a delivery catheter in a low-profile configuration (not shown) and then return to a preset deployed configuration (FIG. 1A) upon release from the delivery catheter. In other embodiments, the mesh can be formed of an elastic material or other suitable self-forming material capable of moving into a desired shape upon release from the delivery catheter.

As best shown in FIG. 1B, the occlusion device 100 includes a proximal portion 104, a distal portion 108, and an intermediate portion 106 extending between the proximal portion 104 and the distal portion 108. In both the deployed configuration shown in FIG. 1A and the unfurled configuration shown in FIG. 1B the occlusion device 100 has a longitudinal dimension L (shown in dashed lines) extending generally along a midline or medial area through the proximal portion 104, the intermediate portion 106, and the distal portion 108 (only a portion of the longitudinal dimension L is labeled in FIG. 1A). The occlusion device 100 is configured to be arranged in the delivery catheter (not shown) such that the distal portion 108 deploys first, which is followed by the intermediate portion 106 and then the proximal portion 104.

In the embodiment of the occlusion device 100 shown in FIGS. 1A and 1B, the mesh 101 comprises the proximal portion 104 of the occlusion device 100. The mesh 101 has a proximal end portion 107 (FIG. 1B) coupled to the proximal connector 105 (FIG. 1B) and a distal end portion 109 (FIG. 1B) coupled to the distal connector 103. In the embodiment shown in FIGS. 1A and 1B, the mesh 101 includes a plurality of curved, broad portions 110 positioned along the longitudinal dimension L, and a plurality of narrow portions 112 individually positioned between adjacent broad portions 110 along the longitudinal dimension L. The mesh 101 is configured such that, when the mesh 101 is in the deployed, relaxed configuration, the broad portions 110 assume a layered, spherically-shaped arrangement, as shown in FIG. 1A. Individual broad portions, for example, can be positioned over all or a portion of the neck of the aneurysm, thereby preventing egress of the implant into the parent vessel, and also disrupting the flow of blood into the aneurysm. Even if a single broad region covers only a portion of the aneurysm neck, a plurality of broad regions near the neck collectively provide complete or near complete neck coverage. In other embodiments, the mesh 101 can be configured to have other flat, broad, or layered configurations.

The broad portions 110 can have the same general characteristics, such as size, curvature and/or shape, along the longitudinal dimension L, or the characteristics of the broad portions 110 can vary along the longitudinal dimension L. For example, in the embodiment shown in FIG. 1B, the broad portions 110 include a plurality of first broad portions 116 having a first size and a plurality of second broad portions 117 having a second size smaller than the first size. Additionally, each of the broad portions 110 has a generally concave shape that defines a generally constant radius of curvature, and in a particular embodiment, one or more of the broad portions 110 can have different radii of curvature. To illustrate this feature, FIG. 1C is a cross-sectional representation of two broad portions 110 of the occlusion device 100 taken along lines 1C.1-1C.1 and 1C.2-1C.2, respectively, in FIG. 1B, that schematically shows the relative radial positioning of the broad portions in the unconstrained, deployed configuration shown in FIG. 1A. Also, the first and second broad portions 116 and 117 are shown opposed to each other for ease of illustration with the understanding that in practice these broad portions may overlap or have different circumferential positions. In this example, the first broad portions 116 individually have a first radius of curvature $R_1$ and the second broad portions 117 individually have a second radius of curvature $R_2$ less than the first radius of curvature $R_1$. As demonstrated by FIG. 1C, each of the first broad portions 116 has an inner surface 116a that defines a portion of the circumference of a circle $C_1$ having a first radius $R_1$, and each of the second broad portions 117 has an inner surface 117a that defines a portion of the circumference of a circle $C_2$ having a second radius $R_2$ less than the first radius $R_1$.

Referring to FIGS. 1A and 1B, the plurality of first broad portions 116 in this embodiment are positioned along the longitudinal dimension L distal of the plurality of second broad portions 117. As such, the larger first broad portions 116 are delivered to the aneurysm first and form an outer mesh structure configured to contact and conform to an inner surface of the aneurysm. As shown in FIG. 1A, the outer mesh structure defines an interior region 118, and the smaller second broad portions 117 are deployed within the interior region 118 to form an inner mesh structure nested within the outer mesh structure. In the embodiment shown in FIGS. 1A-1C, each of the outer mesh structure and the inner mesh structure is generally spherical. In other embodiments, one or both of the outer mesh structure and the inner mesh structure can have other suitable shapes. In yet other embodiments, one or more portions of the mesh 101 are not heat set to form a predetermined three-dimensional shape (independently or collectively).

In the embodiment shown in FIGS. 1A-1C, the mesh 101 is formed of a tubular braid that has been heat set after being wrapped around a series of spherical molds. For example, in one method of manufacture in accordance with the present technology, a first portion of the tubular braid is wrapped one or more times around all or a portion of a first spherical mold having a first diameter. The portion of the braid wrapped around the first spherical mold forms the smaller second broad portions 117 of the inner mesh structure. As the tubular braid is wrapped around the spherical mold, opposing portions of the tubular sidewall are pressed toward one another along the length of the tubular braid, thereby "flattening" the tubular braid while conforming the braid to the curvature of the spherical mold. For example, the cross-sections of the mesh 101 shown in FIG. 1C schematically illustrate the flattened opposing portions 111a, 111b of the sidewall 111 of the once-tubular braid. The resulting broad portion 110 has lateral edges 119, an outer convex braided layer 111a, and an inner concave braided layer 111b that contacts the outer layer 111a along all or a portion of their respective lengths. The outer layer 111a and the inner layer 111b meet at the lateral edges 119. To form a broad portion 110 having a desired arc length between the lateral edges 119, the braid can be flattened against the first spherical mold such that the lateral edges 119 span a particular width of the spherical mold. The braid can be wrapped 180 degrees around the first spherical mold any number of times to achieve a desired number of smaller second broad portions 117. Between wraps, the braid can be pinched together (e.g., via a temporary tubular band, clamp, or other methods) to form the narrow portions 122 (FIGS. 1A and 1B). In the embodiment shown in FIGS. 1A-1C, the mesh 101 has four smaller second broad portions 117. In other embodiments, the mesh 101 can have more or fewer smaller second broad portions 117.

To form the larger broad portions 116 of the outer mesh structure, a second hollow spherical mold having a second diameter greater than the first diameter is placed over the first spherical mold, thereby trapping the first portion of the braid that has been wrapped around the first spherical mold between an outer surface of the first spherical mold and an inner surface of the second spherical mold. A second portion of the tubular braid is fed through an opening in the second spherical mold, and the second portion of the tubular braid is wrapped around the second spherical mold in a similar manner as the first portion. In the embodiment shown in FIGS. 1A-1C, the mesh 101 has three larger first broad portions 116. In other embodiments, the mesh 101 can have more or fewer larger first broad portions 116. A mesh fixture is then positioned over the assembly, and the assembly is heat set. Although the mesh 101 shown in FIGS. 1A-1C is configured to form two spherical layers (e.g., the outer mesh structure and the inner mesh structure), in other embodiments, the mesh 101 can be configured to form more or fewer layers. For example, one or more additional molds can be used to form additional mesh structures from a remaining portion of the tubular braid.

The braid is formed of a plurality of metallic wires, and at least a portion of the wires can have a radiopaque core (e.g., platinum) surrounded by a shape memory alloy and/or superelastic alloy (e.g., nitinol). In these and other embodiments, at least a portion of the wires can be made of other suitable materials.

In some embodiments, the stiffness of the occlusion device 100 varies along its longitudinal dimension L. For example, the stiffness of one or more portions of the mesh 101 is different than other portions of the mesh 101 by varying one or more parameters such as the materials, porosity, thickness, braid count (if applicable), and braid pitch (if applicable) in the individual portions. The stiffness of one broad portion 110 is different from that of another broad portion 110. For example, for the mesh 101 shown in FIGS. 1A-1C, it may be desirable for the larger first broad portions 116 comprising the outer mesh structure to have a first stiffness for framing the aneurysm, and the smaller second broad portions 117 comprising the inner mesh structure to have a second stiffness less than the first stiffness so that the smaller second broad portions 117 are more flexible than the larger first broad portions 116 for packing the aneurysm. Moreover, it may be desirable for the larger first broad portions 116 to be relatively stiffer than the more proximal second broad portions 117 since, once the occlusion device 100 is positioned within the aneurysm, the stiffness will enhance the anchoring and structural integrity of the first broad portions 116 that span across at least a portion of the neck of the aneurysm.

To enhance visibility of the occlusion device 100 and/or mesh 101 during delivery to the aneurysm and/or subsequent to implantation within the aneurysm, the embodiment of the occlusion device 100 shown in FIGS. 1A and 1B optionally includes a flexible member 113, such as a radiopaque element (e.g., a platinum coil), that extends along and/or within at least a portion of the length of the mesh 101. The proximal and distal ends of the flexible member 113 is coupled to the proximal and distal end portions 107, 109, respectively, of the mesh 101 and/or the proximal and distal connectors, 105, 103, respectively (e.g., directly or via a suture). In other embodiments, only one end of the flexible member 113 is connected to one of the proximal connector 105 or the distal connector 103.

Referring still to embodiment shown in FIGS. 1A and 1B, the intermediate portion 106 of the occlusion device 100 has a preset shape that orients the distal portion 108 of the occlusion device 100 at a predetermined angle with respect to the proximal portion 104 upon deployment to prevent the distal portion 108 from. The intermediate portion 106 comprises a radially compacted, curved or bent portion of the mesh 101 that connects a distal-most broad portion 120 to the distal portion 108 of the occlusion device 100. In other embodiments, the intermediate portion 106 can be a separate component coupled to the mesh 101 and/or the proximal portion 104, and/or the intermediate portion 106 can have other suitable shapes and/or configurations (some of which are detailed below with reference to FIGS. 6-12).

The distal portion 108 of the embodiment of the occlusion device 100 shown in FIGS. 1A and 1B includes a directing region 122, and the lead-in member 102 extends distally from the directing region 122. The directing region 122 has a proximal terminus 122a and a distal terminus 122b (FIG. 1A). The directing region 122 extends distally from the intermediate portion 106 along the longitudinal axis L of the occlusion device 100 and, as such, a proximal terminus of the distal portion 108 corresponds to the proximal terminus 122a of the directing region 122. The directing region 122 shown in FIGS. 1A and 1B has an elongated, generally straight configuration and includes a distal zone 124 of the mesh 101 and the connector 103. In this particular embodiment, the distal zone 124 of the mesh 101 has a radially compacted, substantially cylindrical shape. In other embodiments, the directing region 122 and/or the distal zone 124 can have other suitable shapes, sizes, and/or configurations, such as those shown in FIGS. 6-12. The directing region 122 does not need to include any portion of the mesh 101, but instead can be a separate component coupled to the intermediate portion 106. Additionally, the proximal and distal connectors 105, 103 can be made of, include, and/or be coated with a radiopaque material to enhance visibility of the occlusion device 100.

As shown in FIGS. 1A and 1B, this embodiment of the lead-in member 102 has a curved shape in a deployed configuration For example, the lead-in member 102 initially extends distally with respect to the directing region 122 (e.g., from the connector 103) then curves proximally toward the directing region 122 until terminating at an atraumatic tip 126. Because the lead-in member 102 is the first portion of the occlusion device 100 that exits the delivery catheter and contacts the aneurysm wall, the atraumatic tip and/or curved shape of the lead-in member 102 reduces or eliminates stress on the aneurysm wall when delivering the occlusion device 100 to the aneurysm sac. The lead-in member 102 does not necessarily need to be curved as shown, but can be generally straight and/or have other atraumatic yet sufficiently resilient configurations. In the embodiment shown in FIGS. 1A and 1B, the lead-in member 102 is a separate, coiled tube (e.g., a radiopaque coil) that is coupled to the connector 103. In other embodiments, the lead-in member 102 can be formed integrally or monolithically with the occlusion device 100. For example, in some embodiments, the elongated member 113 can extend beyond the distal terminus of the mesh 101 and/or connector 103 to form the lead-in member 102. In yet other embodiments, the occlusion device 100 does not include a lead-in member 102 and the distal portion 108 is comprised solely of the directing region 122.

2.0 REPRESENTATIVE EMBODIMENTS

Figure 2:
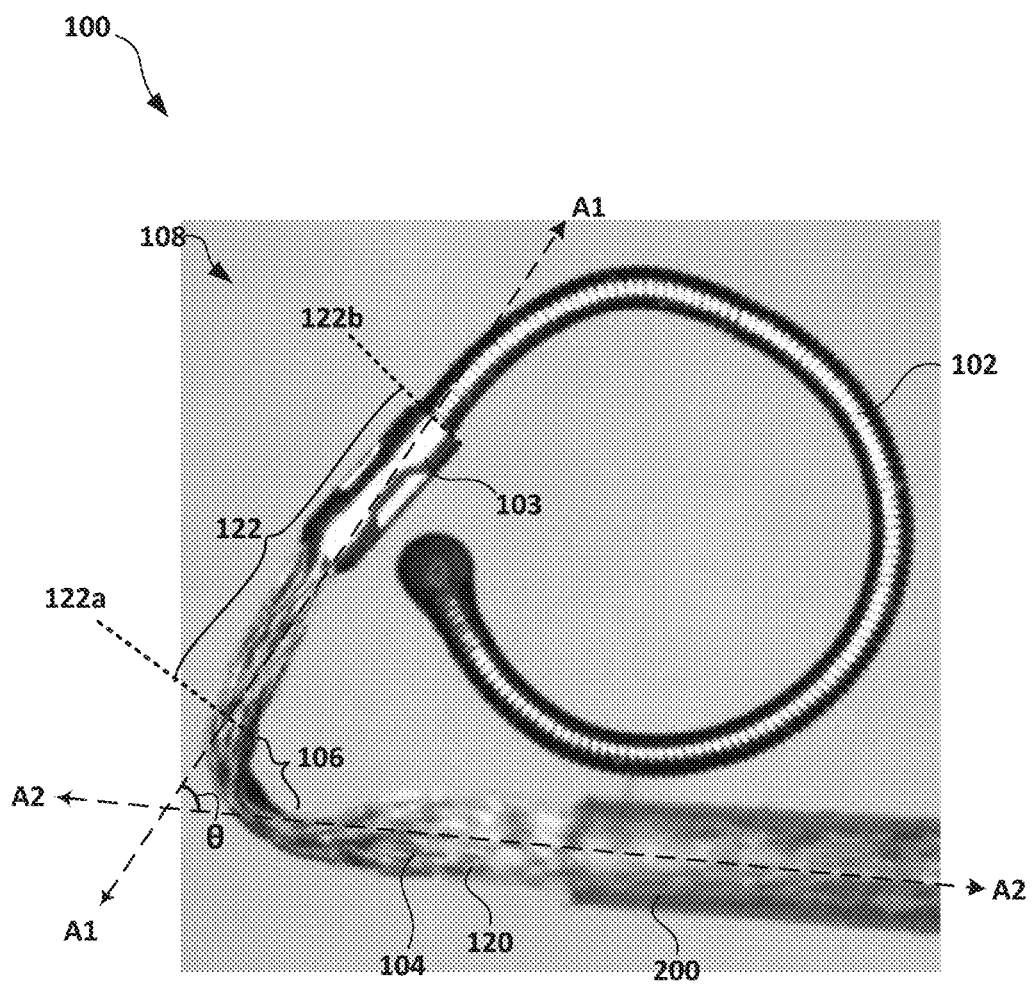
FIG. 2 is a side view of the occlusion device of FIGS. 1A-1B while being deployed from a delivery catheter in accordance with an embodiment of the present technology.

FIG. 2 is a side view of the occlusion device 100 of FIGS. 1A and 1B, shown in a partially-deployed configuration after the distal portion 108 and intermediate portion 106 have exited a delivery catheter 200. As shown in FIG. 2, the directing region 122 extends along a first direction A1 that runs through its proximal terminus 122a and its distal terminus 122b. In some embodiments, the proximal terminus 122a and the distal terminus 122b can refer to a corresponding cross-sectional area of the directing region 122, and the first direction A1 can be defined by a straight line extending through a center of each cross-sectional area. The proximal portion 104 extends along a second direction A2 for the portion of its length immediately proximate the intermediate portion 106. For example, a medially located path along a longitudinal direction of the distal-most broad portion 120 can define the second direction A2.

As shown in FIG. 2, the intermediate portion 106 can be configured such that the first direction A1 of the directing region 122 extends at an angle θ with respect to the second direction A2 of the proximal portion 104 when the occlusion device 100 is in a deployed configuration. The angle θ is between about 45 degrees and about 135 degrees, or between about 60 degrees and about 120 degrees (e.g., 65 degrees, 66 degrees, 70 degrees, 75 degrees, 78 degrees, 82 degrees, 84 degrees, 90 degrees, 95 degrees, 98 degrees, 105 degrees, 107 degrees, 115 degrees, etc.). In particular embodiments, the angle θ is between about 80 degrees and about 110 degrees, and in some embodiments, between about 85 degrees and about 105 degrees. As detailed below with reference to FIGS. 4A-5, when the angle θ is between about 45 degrees and about 135 degrees, it enables pushing the occlusion device 100 out of the delivery catheter 200 and/or re-sheathing the occlusion device 100 while preventing, or at least inhibiting, the distal portion 108 from exiting the aneurysm through the neck during deployment. By preventing or at least inhibiting the distal portion from passing through the neck during deployment, the whole occlusion device 100 is deployed within the aneurysm such that no portion of the occlusion device 100 protrudes into the parent vessel. As such, in contrast to traditional embolic coils and/or intracranial stents, the occlusion device 100 of the present technology significantly reduces and/or eliminates the presence of any nidus in the parent vessel that could be the site for the formation of a thromboembolism.

In addition to the angle θ, the length of the directing region 122 (measured along the first direction A1 between its proximal terminus 122a and its distal terminus 122b) is a design factor related to deployment of the occlusion device 100. For example, if the length of the directing region 122 is too short, the directing region 122 can catch on the distal end of the delivery catheter 200. If the length of the directing region 122 is too long, the distal portion 108 is more likely to exit the aneurysm through the neck, especially in shallow aneurysms. The directing region 122 generally has a length that is from about 25% and about 75% of the aneurysm diameter. For example, the length is from about 0.005 inches and about 0.25 inches, and in some embodiments, from about 0.05 inches and about 0.20 inches. More specifically, the length is between about 0.09 inches and about 0.20 inches, or from about 0.09 inches and about 0.18 inches. The length of the directing region 122, however, is a function of several factors and is not necessarily limited to being within the above ranges.

Figure 3A:
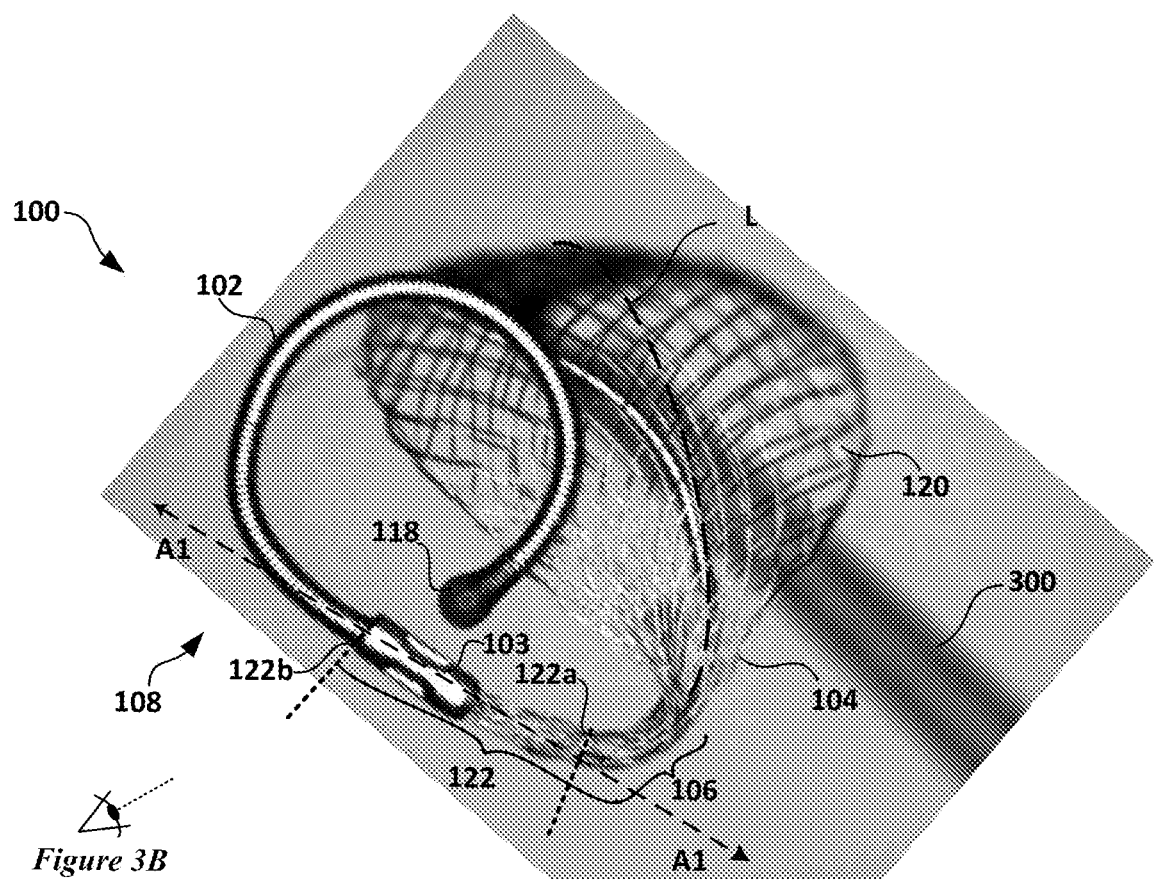
FIG. 3A is a top view of a portion of the occlusion device of FIGS. 1A-1B being deployed from a delivery catheter configured in accordance with an embodiment of the present technology.
Figure 3B:
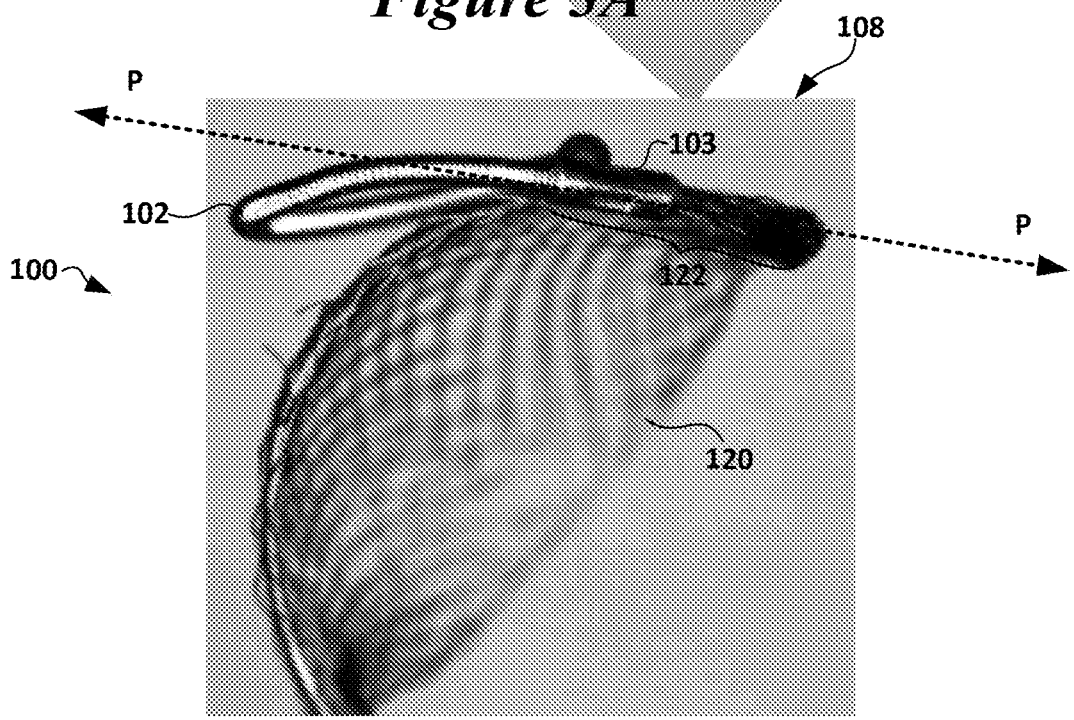
FIG. 3B is a side view of the portion of the occlusion device shown in FIG. 3A from the view indicated by view indicator "FIG. 3B."

FIGS. 3A and 3B are top and side views of the occlusion device 100 of FIGS. 1A-2 in a partially-deployed configuration once the distal portion 108, intermediate portion 106, and distal-most broad portion 120 have exited the delivery catheter 300 (only shown in FIG. 3A). In its deployed configuration, the intermediate portion 106 positions the distal portion 108 of the occlusion device 100 generally within the same plane P (FIG. 3B) as the distal region of the distal-most broad portion 120 of the mesh 101 (FIGS. 1A and 1B). As such, during delivery of the occlusion device 100 to a target aneurysm, the distal portion 108 slides along the inner surface of the aneurysm while the proximal portion 104 is pushed out of the delivery catheter 300 to fill the aneurysm.

Figure 4B:
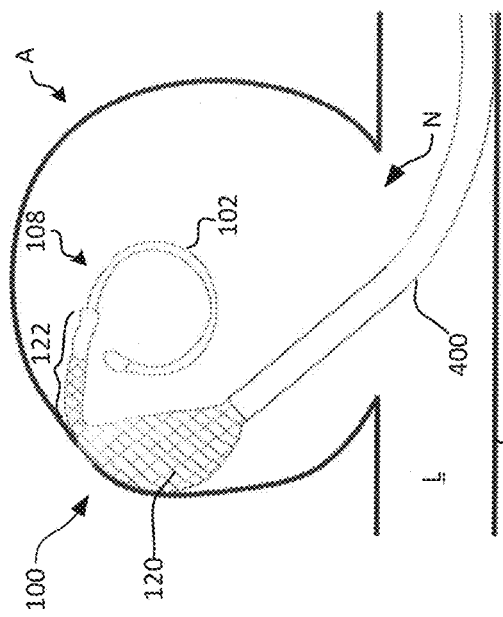
FIGS. 4A-4E are partial schematic illustrations showing a method for deploying an occlusion device within an aneurysm in accordance with an embodiment of the present technology.
Figure 4D:
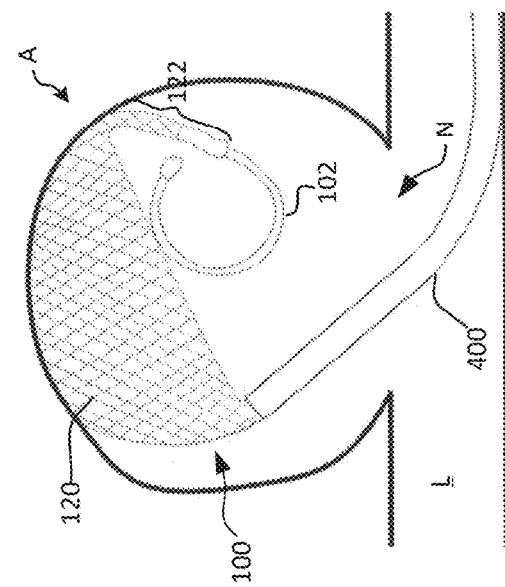
Figure 4A:
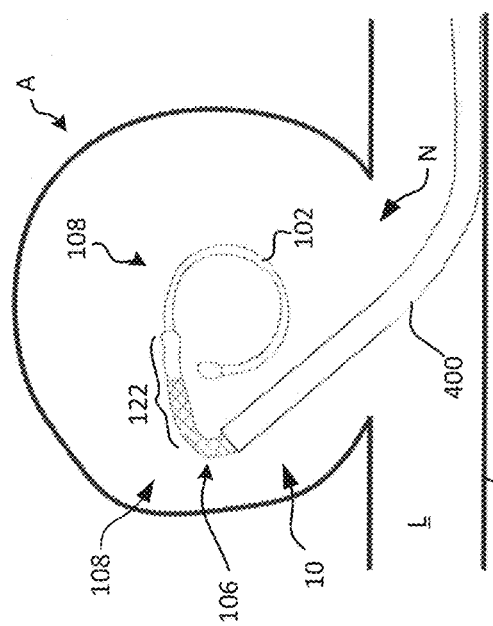

FIGS. 4A-4E illustrate a method of positioning the occlusion device 100 within an aneurysm A having a neck N open to a blood vessel V in accordance with an embodiment of the present technology. The occlusion device 100 is intravascularly delivered to a location within a blood vessel lumen L adjacent a target aneurysm A in a low-profile configuration (not shown) within a delivery catheter 400. The distal portion of the delivery catheter 400 is then advanced through the neck N of the aneurysm A to an interior region of the aneurysm A. As shown in FIG. 4A, the occlusion device 100 is then deployed by pushing the occlusion device 100 distally through the distal opening of the delivery catheter 400 towards a wall of the aneurysm A. As the distal portion 108 and intermediate portion 106 exit the delivery catheter 400, the intermediate portion 106 moves into a pre-set curved shape to position the directing region 122 at a predetermined angle with respect to the emerging proximal portion, as well as with respect to an axis of the distal end region of the delivery catheter 400.

Figure 4C:
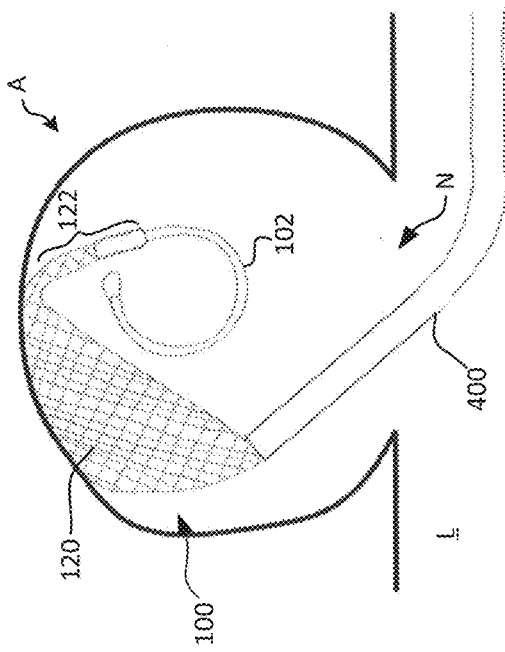
Figure 4E:
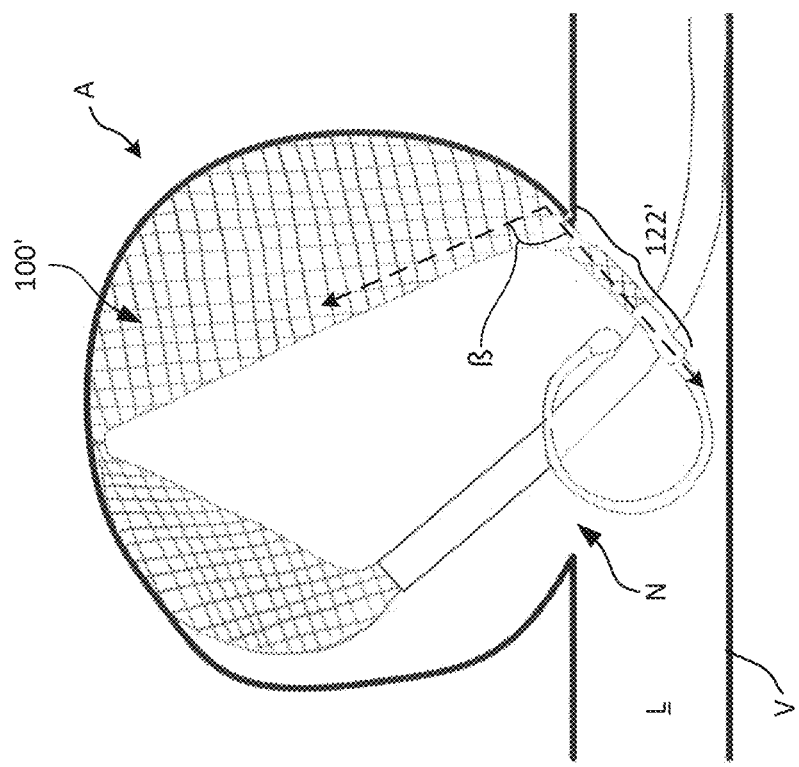

Referring to FIGS. 4B-4D, as more of the occlusion device 100 exits the delivery catheter 400, the distal portion 108 contacts the aneurysm wall and slides up and around the curved inner surface of the aneurysm A. FIG. 4E shows the distal portion 108 as it reaches the neck N of the aneurysm. At this point of deployment, the angle of the directing region 122 with respect to the proximal portion 104 directs the distal portion 108 away from exiting the aneurysm A through the neck N, and instead guides the distal portion 108 across the neck N of the aneurysm A. As shown in FIG. 4E, the combination of the preset angle θ between the directing region 122 and the proximal portion 104 and the length of the directing region 122 relative to a diameter of the aneurysm A enables the directing region 122 to direct the distal portion 108 as the occlusion device 100 is being pushed distally out of the delivery catheter 400 into the aneurysm A. As such, the directing region 122 inhibits the distal portion 108 from exiting the aneurysm A through the neck N and instead directs the proximal portion 104 to cross the neck N and generally remain within the aneurysm A.

Figure 5:
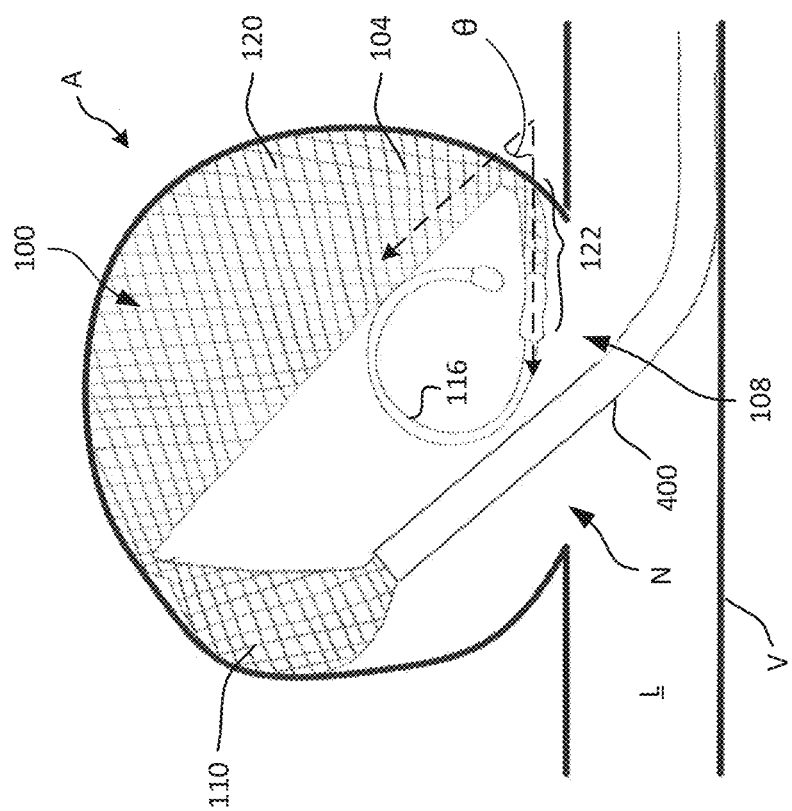
FIG. 5 schematically illustrates an occlusion device without the structure of the present technology for preventing re-entering a lumen of a blood vessel adjacent a targeted aneurysm during delivery of the occlusion device to the targeted aneurysm.

To better appreciate the operation of the directing region 122 of the present technology, FIG. 5 shows a hypothetical occlusion device 100' with a region 122' where the angle β can allow a portion of the hypothetical device 100' to extend into the aneurysm A. As shown in the FIG. 5, the hypothetical occlusion device 100' is not configured in accordance with the present technology (and included for illustrative purposes only) because the angle between the region 122' and the distal-most broad portion is too large such that the distal portion will slide along the inner surface of the aneurysm A and, upon reaching the neck N, exit the aneurysm A into the blood vessel lumen L.

3.0 ADDITIONAL EMBODIMENTS

Figure 6:
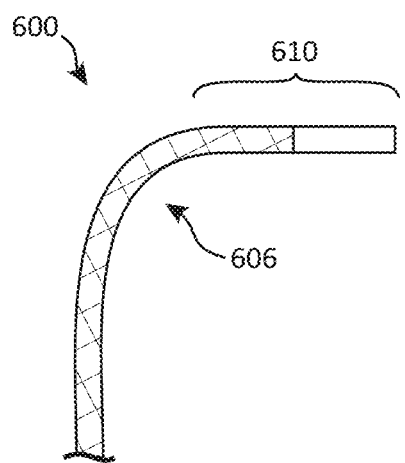
FIG. 6 shows a portion of an occlusion device in accordance with an embodiment of the present technology.
Figure 7:
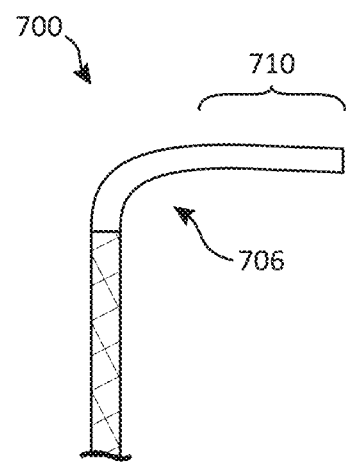
FIG. 7 shows a portion of an occlusion device in accordance with another embodiment of the present technology.

FIGS. 6-12 shows portions of several embodiments of occlusion devices configured in accordance with the present technology. FIG. 6, for example, shows a portion of one embodiment of an occlusion device 600 having a distal portion 608 that does not include a lead-in member such that a directing region 622 comprises the entire distal portion 608. FIG. 7 shows a portion of another embodiment of an occlusion device 700 that, like the occlusion device 600 shown in FIG. 6, does not include a lead-in member. Additionally, the occlusion device 700 has an intermediate portion 706 and a directing region 722 that are formed a single, continuous non-mesh component (e.g., a tube or solid member).

Figure 8:
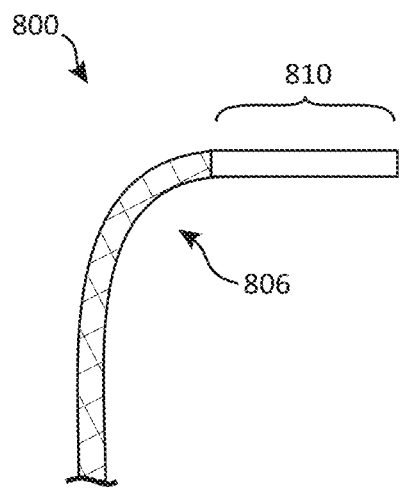
FIG. 8 shows a portion of an occlusion device in accordance with a further embodiment of the present technology.

FIG. 8 illustrates a portion of an occlusion device 800 configured in accordance with a further embodiment of the present technology. The occlusion device 800, like the occlusion device 600 shown in FIG. 6, does not include a lead-in member. The occlusion device 800 of FIG. 8 has an intermediate portion 806 defined by a mesh structure, and a directing region 822 comprising a generally cylindrical component coupled to the mesh structure at the intermediate portion 806.

Figure 9:
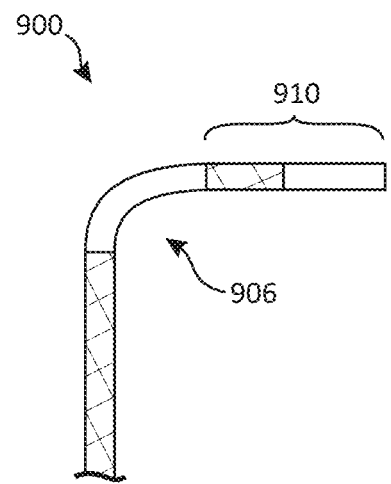
FIG. 9 shows a portion of an occlusion device in accordance with yet another embodiment of the present technology.

A portion of an occlusion device 900 configured in accordance with yet another embodiment of the present technology is shown in FIG. 9. The occlusion device 900 includes an intermediate portion 906 and a directing region 922 extending from the intermediate portion. The intermediate portion 906 is a curved, non-mesh component. The directing region 922 includes a radially compacted, elongated mesh that terminates at a distal crimp. The occlusion device 900 does not include a lead-in member. As such, a distal terminus of the directing region 922 comprises a distal terminus of the occlusion device 900.

Figure 10:
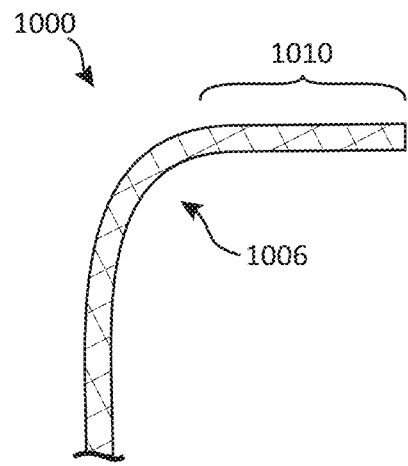
FIG. 10 shows a portion of an occlusion device in accordance with another embodiment of the present technology.
Figure 11:
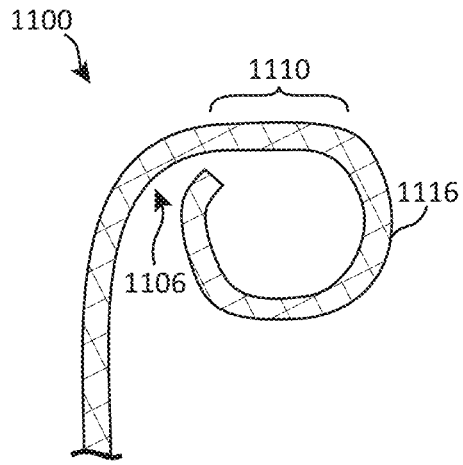
FIG. 11 shows a portion of an occlusion device in accordance with another embodiment of the present technology.

FIGS. 10 and 11 show occlusion devices 1000 and 1100, respectively, that are made entirely of a mesh structure. For example, in FIG. 10, the occlusion device 1000 has an intermediate portion 1006 and a directing region 1022 formed of a continuous mesh structure. As shown in FIG. 10, the directing region 1022 can be defined by the distal-most portion of the mesh structure. The occlusion device 1000 of FIG. 10 does not include a lead-in member. The occlusion device 1100 of FIG. 11 also includes an intermediate portion 1106 and a directing region 1122 formed of a single, continuous mesh structure, as well as a lead-in member 1102 formed of a curved, distal-most portion of the mesh structure.

Figure 12:
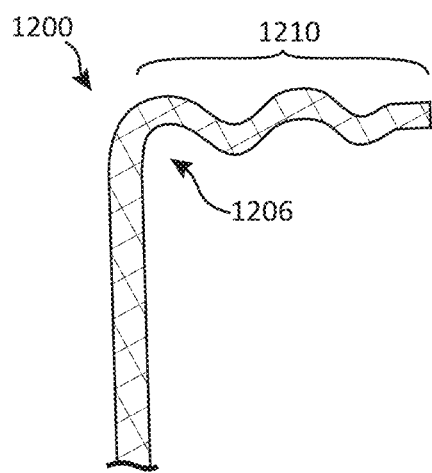
FIG. 12 shows a portion of an occlusion device in accordance with another embodiment of the present technology.

FIG. 12 illustrates a portion of an occlusion device 1200 configured in accordance with a further embodiment of the present technology. In FIG. 12, the occlusion device 1200 includes a non-linear directing region 1222 having an axis A1 defined by a straight line between the proximal and distal termini of the directing region 1222. The occlusion device 1200 includes an intermediate portion 1206 that positions the axis A1 of the directing region 1222 at about a right angle θ with respect to an axis A2 of the proximal portion 1204 of the occlusion device 1200.

4.0 ADDITIONAL EMBODIMENTS OF OCCLUSION DEVICES FOR USE WITH THE DIRECTING REGIONS DISCLOSED HEREIN

Any of the distal portions, intermediate portions, and/or directing regions disclosed herein can be used with additional occlusion devices. For example, the distal ends of any of the occlusion devices described below with reference to FIGS. 13A-38 can be configured to include any of the intermediate portions (e.g., 106, 606, 706, 806, 906, 1006, 1106, etc.), distal portions (e.g., 108, 608, etc.), and/or directing regions (e.g., 122, 622, 722, 822, 922, 1022, 1122, 1222, etc.) disclosed above with reference to FIGS. 1A-12.

Figure 13A:
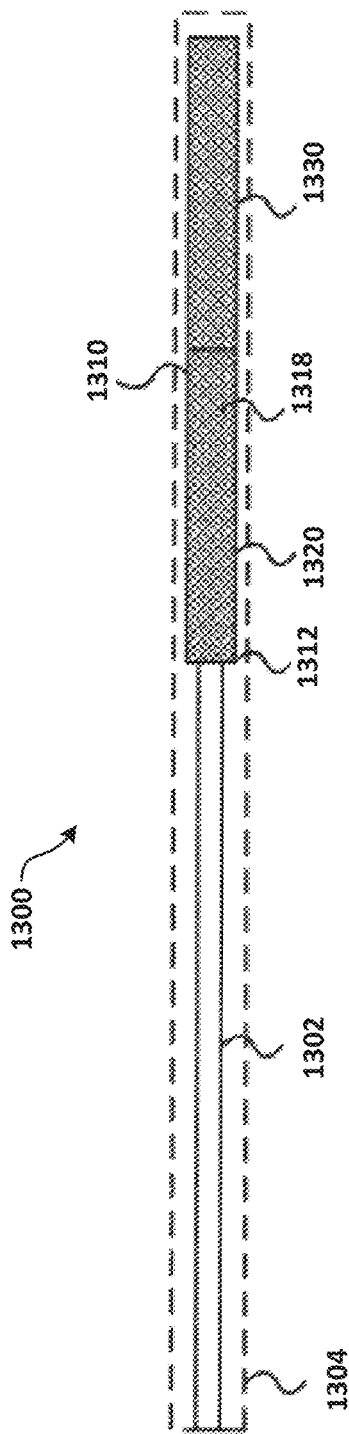
FIG. 13A is a schematic illustration of a medical device according to an embodiment in a first configuration.
Figure 13B:
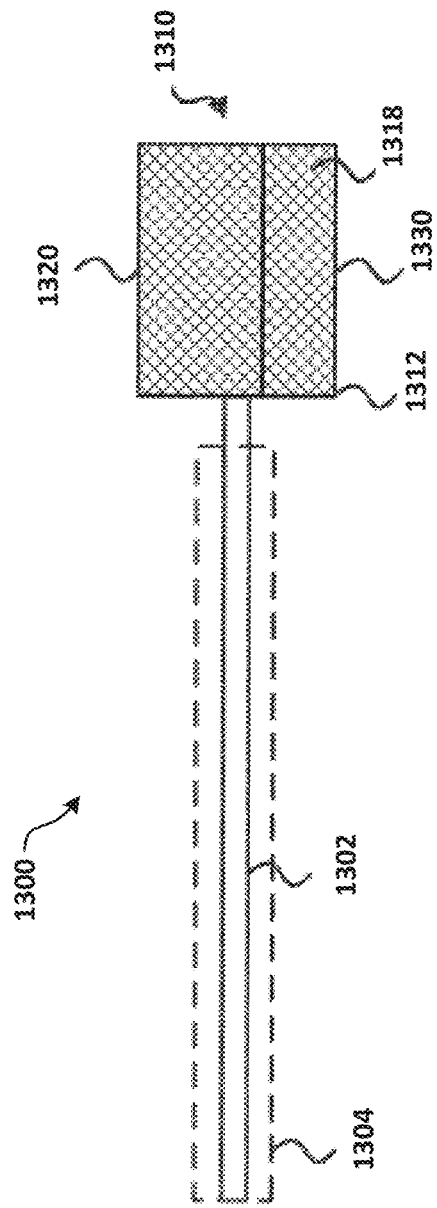
FIG. 13B is a schematic illustration of a medical device according to an embodiment in a second configuration.

FIGS. 13A and 13B, for example, are schematic illustrations of a medical device 1300 shown in a first configuration and a second configuration, respectively. The medical device 1300 is configured to promote healing of an aneurysm. More specifically, at least a portion of the medical device 1300 is configured to occupy at least a portion of the volume defined by a sac of the aneurysm and, in some embodiments, at least a portion of the medical device 1300 is configured to promote endothelial cell attachment over a neck of the aneurysm. Once endothelialization over the aneurysm neck is complete, blood flow into the aneurysm sac from a parent blood vessel (i.e., the vessel on which the aneurysm formed) is prevented.

The medical device 1300 can include an insertion portion 1302 and an occlusion device 1310. The insertion portion 1302 is coupled to the occlusion device 1310, such as, for example, at a proximal portion 1312 of the occlusion device 1310. In some embodiments, the insertion portion 102 is removably coupled to the occlusion device 1310. In this manner, the insertion portion 102 can be separated from the occlusion device 1310 following delivery of the occlusion device to the aneurysm and removed from a patient's vasculature. The insertion portion 1302 can be, for example, a guide wire or a distal end portion of a wire. The medical device 1300 can be used with a cannula or catheter 1304 (shown in dashed lines in FIGS. 13A and 13B) to, for example, deliver the occlusion device 1310 to the aneurysm.

The occlusion device 1310 is configured to be deployed in the aneurysm (e.g., in a sac of an aneurysm). The occlusion device 1310 has a first portion 1320 and a second portion 1330. As shown in FIG. 13A, the occlusion device 1310 has a first configuration in which the first portion 1320 and the second portion 1330 are substantially linearly aligned. In its first configuration, the occlusion device 1310 is configured for insertion through a blood vessel. The occlusion device 1310 is also configured for insertion through a neck of the aneurysm when in its first configuration.

The occlusion device 1310 is movable between its first configuration and a second configuration in which the second portion 1330 at least partially overlaps the first portion 1320, as shown in FIG. 13B. For example, the second portion 1330 can be configured to bend, curve and/or twist in multiple turns such that multiple segments of the first portion 1320 and the second portion 1330 are overlapped. Additionally, at least one of the first portion 1320 and the second portion 1330 can be configured to bend or curve in multiple turns such that the respective first or second portion is overlapped with itself. In some embodiments, the occlusion device 1310 can be understood to have multiple first portions and multiple second portions. In other words, the occlusion device can continually overlap itself in its deployed configuration to occupy all or substantially all of the volume of the aneurysm.

In its second configuration, the occlusion device 1310 is configured to occupy at least a portion of the volume defined by the sac of the aneurysm. In some embodiments, when the occlusion device 1310 is in its second configuration, at least a portion of the occlusion device is configured to be positioned over the neck of the aneurysm. For example, the portion of the occlusion device 1310 at which the second portion 1330 overlaps the first portion 1320 can be configured to be positioned over the neck of the aneurysm. As such, the portion of the occlusion device 1310 disposed over the aneurysm neck has an increased density (e.g., a dual density compared to the first portion 120 or the second portion 1330 individually), which helps to limit or prevent blood flow from entering the sac of the aneurysm. The portion of the occlusion device 1310 positioned over the aneurysm neck can be a scaffold for endothelial cell attachment at the aneurysm neck. For example, the portion of the occlusion device 1310 positionable over the aneurysm neck can be porous, such as by including a porous mesh, as described in more detail herein. In some embodiments, the first portion 1320 and the second portion 1330 of the occlusion device 1310 are biased to the second configuration.

As noted above, in some embodiments, at least a portion of the occlusion device 1310 is porous. For example, in some embodiments, at least a portion of the occlusion device 1310 can include and/or be constructed of a mesh (e.g., woven, braided, or laser-cut) material such that a wall or layer of the occlusion device 1310 defines multiple openings or interstices 1318. More specifically, in some embodiments, at least one of or both the first portion 1320 and the second portion 1330 of the occlusion device 1310 can include the porous mesh. The porous mesh can have a first porosity when the occlusion device 1310 is in its first configuration and a second porosity when the occlusion device is in its second configuration. More specifically, in some embodiments, the porous mesh can have a greater porosity when the occlusion device 1310 is in its second configuration than when the occlusion device is in its first configuration. The porosity of the porous mesh can be increased, for example, because one or more individual pores or openings are larger when in the second configuration than in the first configuration. For example, the porous mesh can be expanded in the second configuration, thereby increasing the space between filaments of the mesh (and thus the size of one or more openings of the mesh). In other words, an overall volume of pore openings can be increased. In another example, the porosity of the porous mesh can be increased because one or more openings that were closed off when the occlusion device 1310 was collapsed into its first configuration are reopened when the occlusion device is moved to its second configuration. In other words, a number of open pores can be increased.

In some embodiments, the first portion 1320 and the second portion 1330 can have one of the same or different porosities. For example, the first portion 1320 can have a porosity greater than a porosity of the second portion 1330. in another example, the second portion 1330 can have a porosity greater than the porosity of the first portion 1320. In still another example, the first and second portions 1320, 1330 can have substantially equivalent porosities in the expanded configuration.

In some embodiments, at least one of the first portion 120 and the second portion 130 includes one, two, three, or more layers. For example, in some embodiments, the first portion 120 of the occlusion device 1310 includes a first layer (not shown in FIG. 13A or 13B) of porous mesh and a second layer (not shown in FIG. 13A or 13B) of porous mesh. The first layer and the second layer can have the same or different porosities. In some embodiments, the first layer is offset from the second layer. As such, the porosity of the first portion is determined by the porosities of the first and second layers and the manner in which the first layer is offset from the second layer.

In some embodiments, at least a portion of the occlusion device 1310, such as at least one of the first portion 1320 or the second portion 1330 can include a shape-memory material, such as, for example, nitinol, and can be pre-formed to assume a desired shape. Thus, in such an embodiment, the portion of the occlusion device 1310 (e.g., the first portion 1320 and/or the second portion 1330) can be biased into an expanded second configuration and moved to a collapsed first configuration by restraining or compressing the portion of the occlusion device.

In some embodiments, at least a portion of the occlusion device 1310, such as at least one of the first portion 1320 or the second portion 1330 can include an electropositive material, described in more detail below.

The occlusion device 1310 when in the expanded configuration can have a variety of different shapes, sizes and configurations. For example, in some embodiments, when in the expanded configuration the occlusion device 1310 can be substantially spherical. In some embodiments, the occlusion device 1310 can be substantially helical. In some embodiments, the occlusion device 1310 can be substantially circular, disc-shaped, or ring-shaped. In some embodiments, the occlusion device 1310 can be a custom-made shape based on a shape of a target aneurysm within a patient: for example, a shape modeled after the shape of the target aneurysm as detected by an imaging device. For example, an image of the aneurysm shape can be acquired using an angiogram, and the occlusion device 1310 can be modeled after the shape of the aneurysm shown in the angiogram. In some embodiments, the occlusion device 1310 can include multiple portions having varying outer perimeters or outer diameters. For example, in some embodiments, when in the expanded configuration the occlusion device 1310 can include a first portion having a first outer perimeter, a second portion having a second outer perimeter and a third portion having a third outer perimeter. In such an embodiment, the second outer perimeter can be smaller than each of the first outer perimeter and the third outer perimeter.

In one example use of the medical device 100, a catheter 1304 can be inserted into a blood vessel and directed to a desired treatment site near a vascular defect, such as the aneurysm. The occlusion device 1310 is inserted into an elongate lumen of the catheter 1304 for delivery to the treatment site. A distal portion of the catheter 1304 is positioned adjacent the aneurysm within the blood vessel. The occlusion device 1310 is moved from a first position inside the catheter to a second position outside the catheter. When the occlusion device 1310 is in its first position, each of the first portion 1320 and the second portion 1330 are in a first configuration. For example, in the first configuration, each of the first and second portions 1320, 1330 can be compressed or collapsed within the lumen of the catheter 1304 and are substantially linear in configuration.

The occlusion device 1310 can be oriented with respect to an opening in the vessel wall in fluid communication with the aneurysm such that the occlusion device can enter a sac of the aneurysm when the occlusion device 1310 is moved to its second position. The occlusion device 1310 can be moved from its first position to its second position with the assistance of the insertion portion 1302 such that the occlusion device 1310 is directed into and positioned within a sac of the aneurysm. When the occlusion device 1310 is in its second position, the first and second portions each have a second configuration. For example, in the second configuration, each of the first and second portions 1320, 1330 can be expanded into a three-dimensional shape. The three-dimensional shape of the first portion 1320 in the second configuration can be similar to or different from the three-dimensional shape of the second portion 1330. In the second configuration, the first portion 1320 of the occlusion device 1310 substantially overlaps the second portion 1330. In some embodiments, the second portion 1330 is disposed in an interior region defined by the first portion when each of the first portion and the second portion are in their respective second configurations.

The first and second portions 1320, 1330 can be moved to their respective second configurations concurrently or sequentially. For example, in some embodiments, the second portion 1330 is moved to its second configuration before the first portion 1320 is moved to its second configuration. The occlusion device 1310 can assume a biased expandable configuration such that the walls of the occlusion device 1310 contact at least a portion of the wall of the aneurysm and/or such that a portion of the occlusion device is disposed over the neck of the aneurysm. The presence of the occlusion device 1310 over the neck of the aneurysm can substantially reduce and/or prevent further blood flow from the parent vessel into the aneurysm sac because the occlusion device can act as a physical flow disruptor for blood flowing from the parent vessel and as a scaffold for endothelial cell attachment at the aneurysm neck to promote endothelialization of the neck/vessel wall. The insertion portion 1302 can then be disconnected from a proximal end of the occlusion device 1310 and removed through the catheter 1304.

FIGS. 14A-14E illustrate a medical device according to an embodiment. The medical device 1400 can include all or some of the same features and functions as described above for medical device 1300. The medical device 1400 includes an insertion portion 1402 and an occlusion device 1410. The occlusion device 1410 is removably coupled at its proximal end to a distal end of the insertion portion 1402.

Figure 14A:
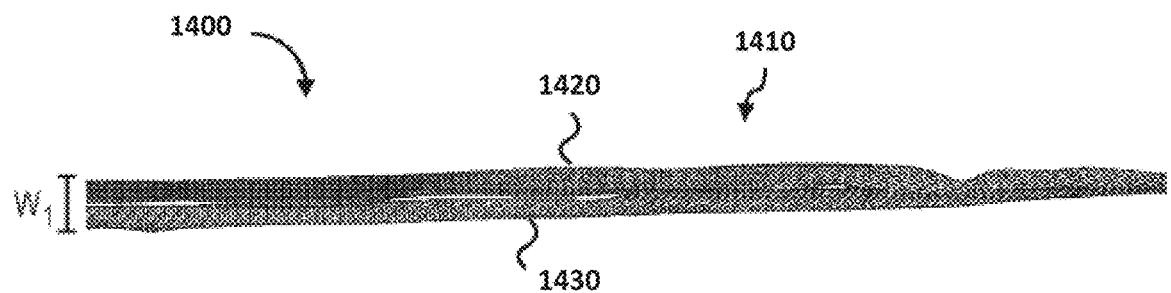
FIG. 14A is a side view of a medical device according to an embodiment in a first configuration.
Figure 14B:
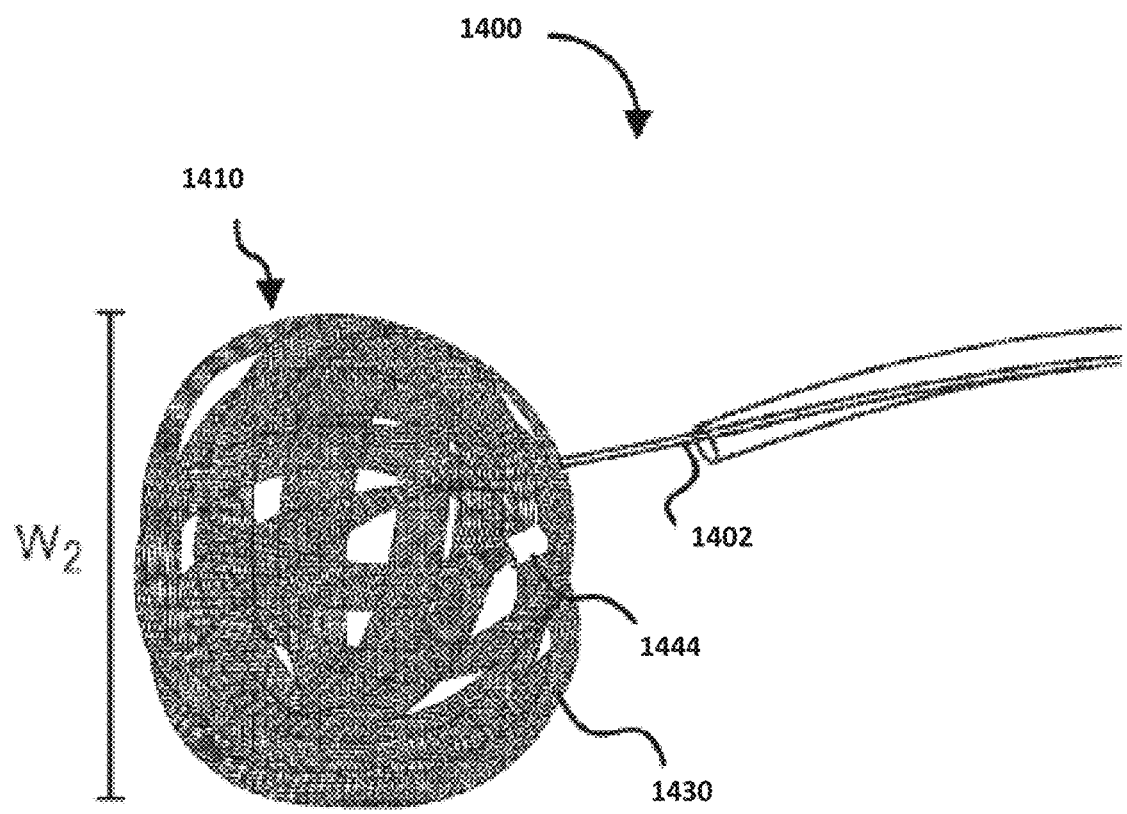
FIG. 14B is a side view of a medical device according to an embodiment in a second configuration.
Figure 14C:
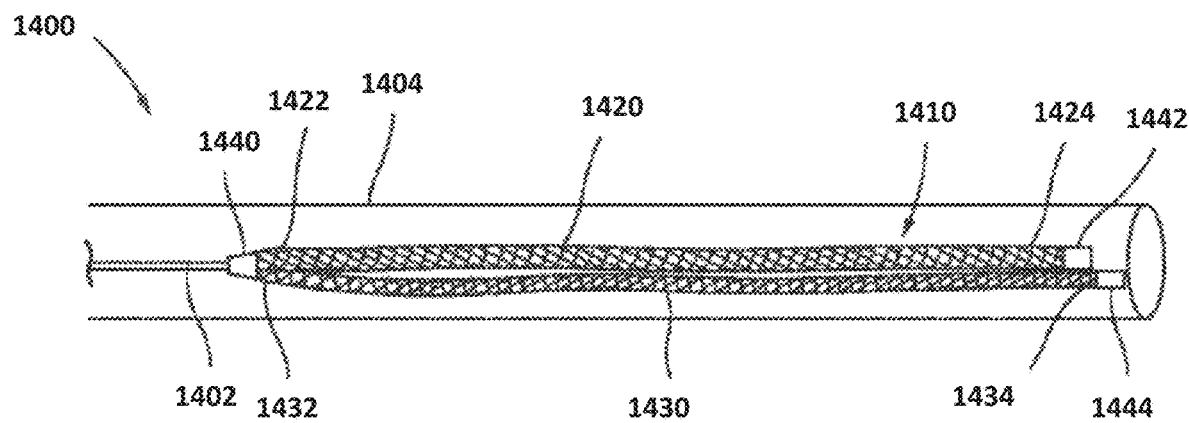
FIG. 14C is a view of the medical device of FIG. 14A in a first configuration during insertion into an aneurysm.
Figure 14D:
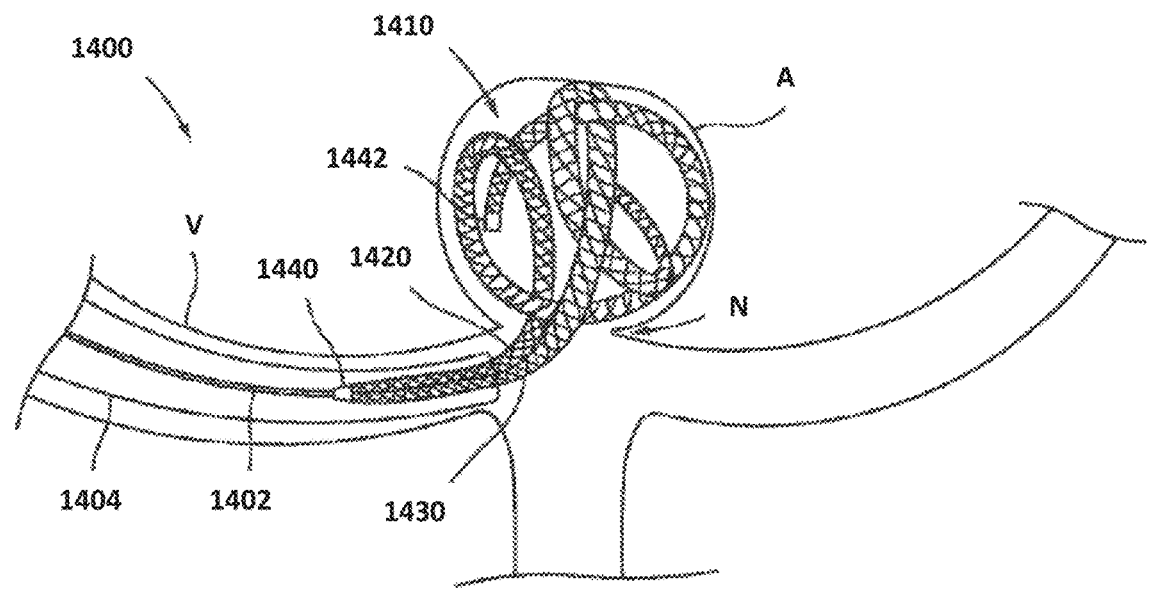
FIG. 14D is a view of the medical device of FIG. 14A in a second configuration during insertion into an aneurysm.
Figure 14E:
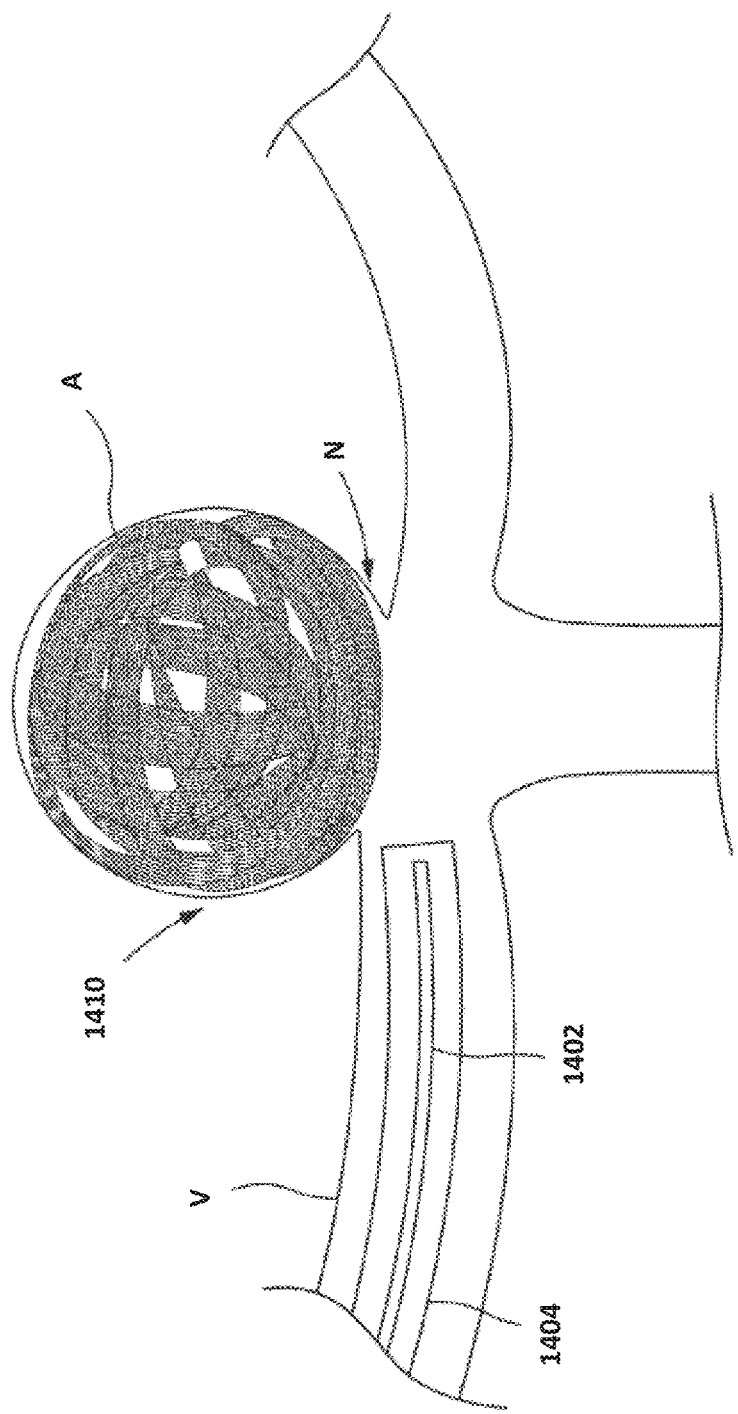
FIG. 14E is a view of the medical device of FIG. 14A in a third configuration during insertion into an aneurysm.

The occlusion device 1410 includes a first portion 1420 and a second portion 1430. As shown in FIGS. 14A and 14C, the occlusion device 1410 has a first, or collapsed, configuration in which the first and second portions 1420, 1430 are substantially linearly aligned. In this manner, the occlusion device 1410 can be disposed within a lumen of a catheter 1404 for delivery through a blood vessel V to a treatment site, such as to an aneurysm A. In its first configuration, the occlusion device 1410 has a first width W1, as shown in FIG. 14A. As shown in FIGS. 14B, 14D, and 14E, the occlusion device 1410 is moveable to a second, or expanded or deployed, configuration. The insertion portion 1402 is configured to move the occlusion device 1410 from the first configuration to the second configuration. The insertion portion 1402 can be disconnected from the occlusion device 1410 when the occlusion device 1410 is in its second configuration.

In its second configuration, the occlusion device 1410 is configured to occupy at least a portion of the volume defined by a sac of the aneurysm A. As such, the occlusion device 1410 has a second width W2 in the second, expanded, configuration greater than its first width W1. For example, the occlusion device 1410 can be substantially narrow and elongate in its first configuration and can assume a three-dimensional shape in its second configuration. In the embodiments illustrated in FIGS. 14A-14E, the occlusion device 1410 has a substantially spherical shape in its second configuration. The occlusion device 1410 can be compliant such that its three-dimensional shape can accommodate any irregularities in the shape of the aneurysm. In the second configuration, the second portion 1430 of the occlusion device 1410 at least partially overlaps the first portion 1420. At least a portion of the occlusion device 1410 is configured to be positioned over a neck N of the aneurysm A when the occlusion device is in its second configuration within the sac of aneurysm A. The occlusion device 1410 is configured to facilitate endothelial cell attachment at the neck N of the aneurysm A, as described in more detail herein.

In the embodiment illustrated in FIG. 14A, the first portion (or member) 1420 is a first ribbon-like strand and the second portion (or member) 1430 is a second ribbon-like strand discrete from the first portion. In other embodiments, an occlusion device can include a first portion and a second portion from a single ribbon-like strand (e.g., integrally or monolithically constructed), instead of discrete portions. A first end 1422 of the first portion 1420 is coupled to a first end 1432 of the second portion 1430. Any suitable mechanism for coupling the first end 1422 of the first portion 1420 to the first end 232 of the second portion 1430 can be used, such as an adhesive, a mechanical coupler, a weld, or the like, or any combination of the foregoing. For example, the first ends 1422, 1432 can be coupled by a band 1440. The band 1440 can also be configured to help couple the insertion portion 1402 to the occlusion device 1410. The band 1440 can be or can include, for example, a radiopaque marker.

A second end 1424 of the first portion 1420 and a second end 1434 of the second portion 1430 each have a radiopaque marker 1442, 1444, respectively, coupled thereto. The radiopaque markers 1442, 1444 are configured to facilitate imaging of the occlusion device 1410 during delivery to the treatment site and/or subsequent to implantation. The markers 1442, 1444 are configured to be wholly disposed within the sac of the aneurysm A when the occlusion device 1410 is in its second configuration. As such, the markers 1442, 1444 will not puncture the wall of the aneurysm A or the vessel V, and the markers 1442, 1444 will not interfere with endothelial cell attachment at the aneurysm neck. This is also beneficial because if the markers 1442, 1444 were positioned at or proximate to the neck of the aneurysm, blood from a parent blood vessel could have a tendency to clot around the marker.

When the expandable member 1410 is moved between its first configuration and its second configuration, at least one of the first portion 1420 and the second portion 1430 is also moveable between a first configuration and a second configuration. The first portion or member 1420 has a first, collapsed, configuration in which the first portion 1420 is substantially elongate and has a first width. The first portion 1420 has a second, expanded, configuration, in which the first portion 1420 has a second width greater than the first width. For example, the first portion 1420 can be moveable from a substantially linear, elongate collapsed configuration to a multi-dimensional (e.g., three-dimensional) shape in the expanded or deployed configuration. As shown in FIGS. 14B and 14E, the first portion 1420 can have a three-dimensional shape in the expanded configuration that lends an overall spherical shape to the occlusion device 1410. The first portion 1420 can be biased to its second, expanded, configuration.

The first portion or member 1420 is porous and, for example, can include or be constructed of a porous mesh. The porous mesh can be formed using filaments that are woven or braided together in a manner that openings or interstices are present between portions of the filaments at least when the occlusion device 1410 is in its second configuration. For example, the porous mesh can include a plurality of braided wires. Suitable mesh material is described in more detail herein. The porous mesh can have a first porosity when the first portion 1420 is in the first configuration and a second porosity when the first portion 1420 is in the second configuration. For example, when the first portion 1420 is moved from its first, collapsed, configuration to its second, expanded, configuration, the mesh can be expanded such that the size of the openings of the mesh is increased, thus increasing the porosity of the mesh. The porous mesh is configured to act as a scaffold that promotes clot formation and endothelium cell attachment when the mesh is disposed within the aneurysm A. Specifically, endothelial cells will migrate to the openings of the mesh.

The first portion 1420 of the occlusion device 1410 includes a first layer of porous mesh and a second layer of porous mesh. In this manner, the density of the first portion 1420 is greater than the density of either the first or second layers individually. Such a dual-density structure can help to limit or prevent blood flow into the aneurysm A, for example when the first and second layers of the first portion 1420 arc disposed over the neck N of the aneurysm A. The first layer of porous mesh and the second layer of porous mesh can have the same porosities, or different porosities. The first layer of porous mesh can be offset from the second layer of porous mesh. In this manner, the overall porosity of the first portion 1420 is greater than the porosity of either the first or second layers individually. The first and second layers of porous mesh can be coupled together in any suitable manner. For example, the first portion 1420 can be formed using an elongate tubular mesh having an elongate lumen therethrough. In such an embodiment, the elongate mesh can be flattened from a tubular structure to a ribbon-like structure such that a first side, or layer, of the mesh is disposed on or proximate to a second side, or layer, of the mesh, thus forming a dual density, or dual-layered, mesh structure.

The second portion, or member, 1430 of the occlusion device 1410 can be configured the same as or similar to, and can be used in the same or similar manner, as the first portion 1420. When the expandable member 1410 is moved between its first configuration and its second configuration, the second portion 1430 is also moveable between a first, collapsed, configuration in which the second portion is substantially elongate and has a third width, and a second, expanded, configuration, in which the second member has a fourth width greater than the third width. For example, the second portion 1430 can be moveable from a substantially linear, elongate collapsed configuration to a multi-dimensional (e.g., three-dimensional) shape in the expanded configuration. As shown in FIGS. 14B and 14E, the second portion 1430 can have a three-dimensional shape in the expanded configuration that lends an overall spherical shape to the occlusion device 1410. The second portion 1430 can be biased to its second, expanded, configuration.

The second portion 1430 is porous and can include or be constructed of a porous mesh. The porous mesh can be configured the same as or similar to, and can be used in the same or similar manner, as the porous mesh described above with respect to the first portion 1420 of the occlusion device 1410. For example, the porous mesh can include a weave or braid of filaments that is porous at least when the occlusion device 1410 is in its second configuration. Additionally, the porous mesh of the second portion 1430 can have a first porosity when the second portion 1430 is in the first configuration and a second porosity when the second portion 1430 is in the second configuration. In some embodiments, the second portion 1430 of the occlusion device 1410 includes a first layer of porous mesh and a second layer of porous mesh, which can be of the same or different porosities. In this manner, the total density of the second portion 1430 is greater than the density of either the first or second layers individually. The first layer of porous mesh can be offset from the second layer of porous mesh such that the overall porosity of the second portion 1430 is greater than the porosity of either the first or second layers individually. Similarly as described above with respect to the first portion 1420, the first and second layers of porous mesh of the second portion 1430 can be formed from a monolithically constructed elongate tubular mesh that is flattened into a ribbon-like structure.

The first portion 1420 and the second portion 1430 of the occlusion device 1410 can be the same or different sizes. For example, as shown in FIG. 14E, the first portion 1420 can have a length in its first, collapsed, configuration, that is less than a length of the second portion 1430 in its first, collapsed, configuration. In this manner, the markers 242, 1444 will be sequentially introduced through the neck N of the aneurysm A, which permits the occlusion device 1410 to be introduced through a narrower neck N. In another example, the first portion 1420 and the second portion 1430 can have the same or different widths. In some embodiments, for example, the first width of the first portion 1420 in its first configuration is wider than the third width of the second portion 1430 in its first configuration. The second width of the first portion 1420 in its second configuration can also be wider than the fourth width of the second portion 1430 in its second configuration. In another example, the fourth, expanded, width of the second portion 1430 can be greater than the second, expanded, width of the first portion 1420. In some embodiments, the porous mesh of the first portion 1420 can have a multi-dimensional shape with a first width when the occlusion device 1410 is in its second configuration, and the porous mesh of the second portion 1430 can have a multi-dimensional shape with a second width less than the first width when the occlusion device is in its second configuration.

In some embodiments, for example, the first portion 1420 (or the porous mesh of the first portion) can have a width of about 8 mm when the occlusion device is expanded in its second configuration, and the second portion 1430 (or the porous mesh of the second portion) can have a width of about 9.5 mm when the occlusion device is expanded in its second configuration. As such, in an embodiment in which the first portion 1420 has a smaller overall size in the expanded configuration than the second portion 1430, the first portion 1420 can be configured to be disposed within an open interior region formed by the second portion 1430 in its second configuration.

In some embodiments, a variation of medical device 1400 is contemplated. For example, in such an embodiment, the first portion of the occlusion device can include a first tubular mesh that defines a lumen therethrough, and the second portion of the occlusion device can include a second tubular mesh disposed within the lumen of the first tubular mesh. The first and second tubular mesh structures can be formed into a substantially ribbon-like strand. As such, the occlusion device has a four-layer density. The occlusion device can include additional ribbon-like strands in addition to the strand formed by the first and second portions. For example, the occlusion device can include one, two, three, four, five, six, seven, eight, or nine strands, with each of the strands having a desired number of layers (e.g., two, four, or more layers). As such, an occlusion device can be formed that has a desired amount of density. As noted above, a highly dense structure helps to prevent blood flow from the parent blood vessel into the aneurysm. Each layer or portion of the occlusion device can have the same or different density as the other layers or portions. Furthermore, each layer or portion of the occlusion device can have the same or different porosity as the other layers or portions.

Figure 15:
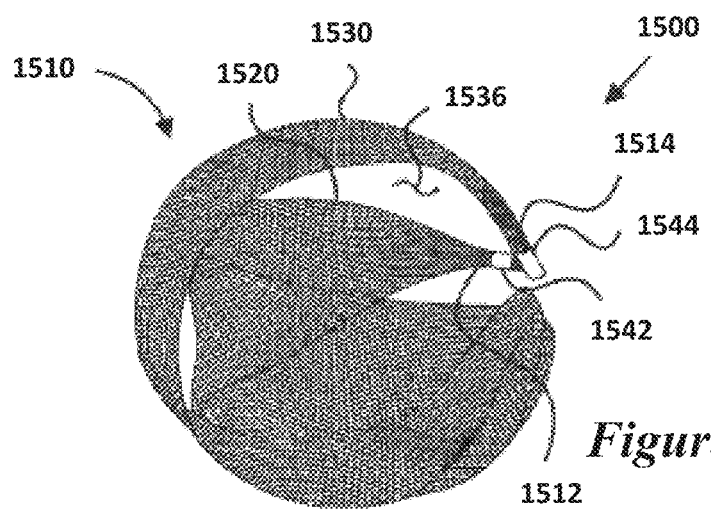
FIG. 15 is a view of a portion of a medical device in an expanded configuration, according to an embodiment.

FIG. 15 illustrates a portion of another embodiment of a medical device. The medical device 1500 can include the same or similar features and functions as described above for previous embodiments. For example, the medical device 1500 includes an occlusion device 1510 and an insertion portion or member (not shown in FIG. 15). The occlusion device 1510 is shown in an expanded configuration and can be moved between a compressed or collapsed configuration in which the occlusion device is substantially elongate and the expanded configuration in the same or similar manner as described above for occlusion device 1410. In the expanded configuration, a first portion 1520 of the occlusion device 1510 is overlapped by a second portion 1530 of the occlusion device. Additionally, at least a portion of the first portion 1520 is disposed within an open interior region 1536 defined by the second portion 1530 when the occlusion device 1510 is in its expanded configuration.

The occlusion device 1510 includes a ribbon-like strand of porous mesh. At least a portion of the porous mesh is configured to be positioned over a neck of an aneurysm when the occlusion device 1510 is in the expanded configuration. The porous mesh is configured to bend, curve, and/or twist at multiple turns into a substantially spherical shape when the occlusion device 1510 is in the expanded configuration. The porous mesh can be a ribbon-like structure that is wider than the porous mesh of occlusion device 1410. In this manner, the porous mesh of occlusion device 1510 can be a shorter length than that of occlusion device 1410 and still provide a similar amount of coverage within the aneurysm (and over the neck of the aneurysm) as occlusion device 1410. The porous mesh can include one, two, or more layers depending on the desired density and porosity of the occlusion device 1510. In some embodiments, a first radiopaque marker 1542 is coupled to a first end 1512 of the occlusion device 1510 and a second radiopaque marker 1544 is coupled to a second end 1514 of the occlusion device. The occlusion device 1510 is configured to be wholly disposed within the aneurysm such that the radiopaque markers 1542, 1544 are wholly disposed within the aneurysm sac and the porous mesh is disposed over the neck of the aneurysm. In some embodiments, the radiopaque markers are configured to be positioned at a side of the aneurysm (i.e., disposed away from the neck of the aneurysm).

Figure 16:
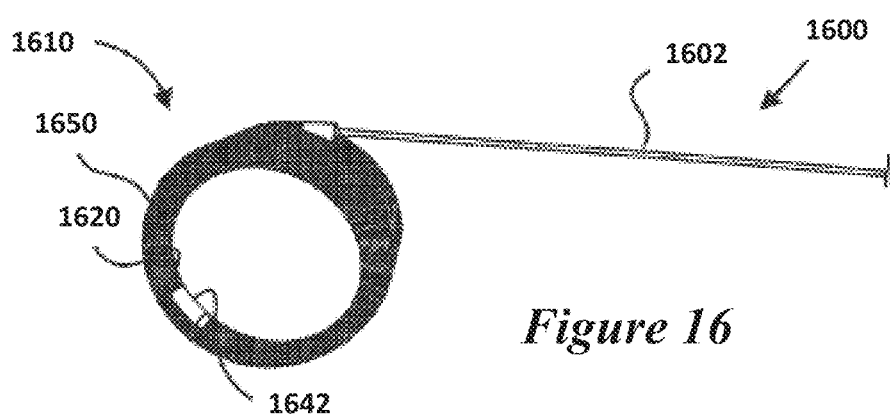
FIGS. 16-22 are views of a medical device in an expanded configuration, according to embodiments.

FIG. 16 illustrates another embodiment of a medical device. The medical device 1600 can include the same or similar features and functions as described above for previous embodiments. For example, the medical device 1600 includes an occlusion device 1610 and an insertion portion or member 1602. The occlusion device 1610 is sized to occupy the sac of an aneurysm, and the insertion member 1602 is configured to facilitate delivery of the occlusion device into the sac of the aneurysm. The occlusion device 1610 is shown in an expanded configuration and can be moved between a compressed or collapsed configuration and the expanded configuration in the same or similar manner as described above for previous embodiments.

The occlusion device 1610 includes at least one ribbon-like strand of porous mesh configured to be expanded within the aneurysm as a 360 degree spiral or ring-shaped structure. In the expanded configuration, a first portion 1620 of the occlusion device 1610 is overlapped by a second portion (not shown in FIG. 16) of the occlusion device, which is overlapped by a third portion 1650 of the occlusion device. In this manner, at least a portion of the occlusion device 1610 includes two, three, four, or more layers of implant material (e.g., porous mesh, as described above in previous embodiments), which can be positioned over the neck of the aneurysm from within the aneurysm to function as a dense flow disruptor. In some embodiments, a radiopaque marker 1642 is coupled to the occlusion device 1610.

Figure 17:
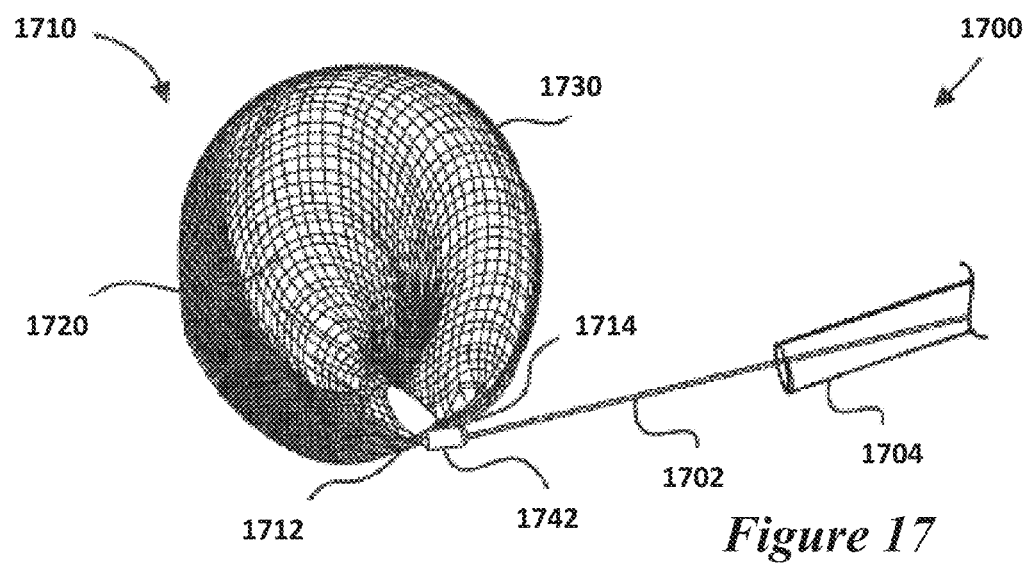

FIG. 17 illustrates another embodiment of a medical device. The medical device 1700 can include the same or similar features and functions as described above for medical device 1600. For example, the medical device 1700 includes an occlusion device 1710 and an insertion portion or member 1702. The medical device 1700 can be delivered to an aneurysm or other vascular defect using a microcatheter 1704. The occlusion device 1710 is sized to occupy at least a portion of the volume defined by the sac of the aneurysm, and the insertion member 1702 is configured to facilitate delivery of the occlusion device into the sac of the aneurysm. The occlusion device 1710 is shown in an expanded configuration and can be moved between a compressed or collapsed configuration and the expanded configuration in the same or similar manner as described above for previous embodiments.

The occlusion device 1710 includes a porous mesh configured to be expanded within the aneurysm as a substantially circular or disc-shaped structure, as shown in FIG. 17. In the expanded configuration, a first end portion 1712 of the occlusion device 1710 is engaged with and/or overlapped with a second end portion 1714 of the occlusion device. The occlusion device 1710 includes a first portion 1720 having a first density of porous mesh and a second portion 1730 having a second, higher, density of porous mesh. More specifically, a weave or braid of the porous mesh has a higher density in the second portion 1730 than in the first portion 1720 of the occlusion device. The occlusion device 1710 is configured to be disposed within the aneurysm (or other vascular defect) such that at least a portion of the second portion 1730 is disposed over the neck of the aneurysm, because the higher density promotes endothelial cell attachment to the occlusion device. The occlusion device 1710 includes at least one radiopaque marker 1742, which can be disposed on one of the first end portion 1712 (as shown in FIG. 17) and/or the second end portion 1714. When the occlusion device 1710 is disposed within the aneurysm in its expanded configuration such that the higher density second portion 1730 is disposed over the neck of the aneurysm, the at least one radiopaque marker 1742 is disposed within the sac of the aneurysm away from the neck of the aneurysm.

Figure 18:
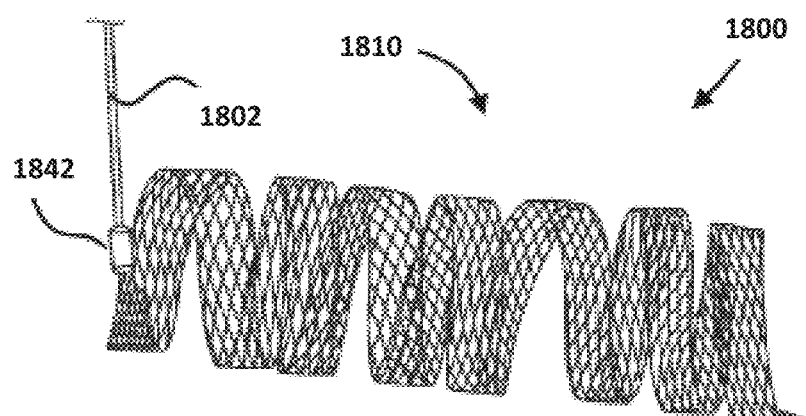

FIG. 18 illustrates another embodiment of a medical device. The medical device 1800 can include the same or similar features and functions as described above for previous embodiments. For example, the medical device 1800 includes an occlusion device 1810 and an insertion portion or member 1802. The occlusion device 1810 is sized to occupy at least a portion of a volume defined by the sac of the aneurysm, and the insertion member 1802 is configured to facilitate delivery of the occlusion device into the sac of the aneurysm. The occlusion device 1810 is shown in an expanded configuration and can be moved between a compressed or collapsed configuration and the expanded configuration in the same or similar manner as described above for previous embodiments.

The occlusion device 1810 includes a ribbon-like strand of porous mesh having at least two layers of mesh. The occlusion device 1810 is configured to be expanded within the aneurysm as a substantially helical or coil shaped structure, as shown in FIG. 18. The occlusion device 1810 can be disposed within the aneurysm (or other vascular defect) such that at least a portion of the implant is disposed over the neck of the aneurysm to facilitate endothelial cell attachment at the neck. The occlusion device 1810 includes at least one radiopaque marker 1842, which can be disposed on an end of the occlusion device 1810, as shown in FIG. 18. The insertion member 1802 can be removably coupled to the occlusion device at the radiopaque marker.

Figure 19:
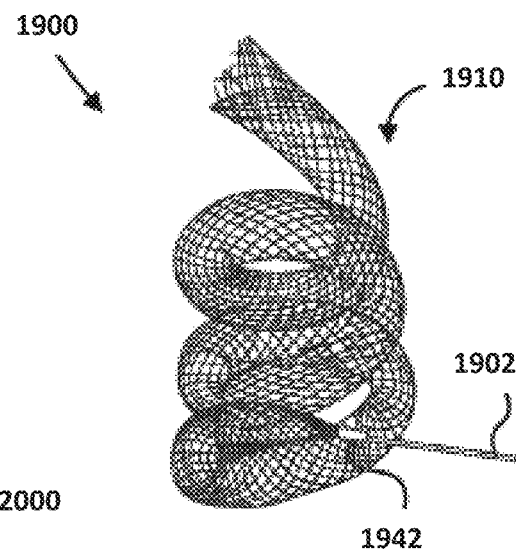

FIG. 19 illustrates another embodiment of a medical device. A medical device 1900 includes all the same or similar features and functions as described above for medical device 1800. For example, the medical device 1900 includes an occlusion device 1910, an insertion portion or member 1902, and a radiopaque marker 1942 coupled to an end of the occlusion device. The occlusion device 1910 includes a porous mesh formed of a tubular or rounded braid structure. The rounded braid structure can lend more softness to the occlusion device 1910 than, for example, the flattened ribbon-like structure previously described.

Figure 20:
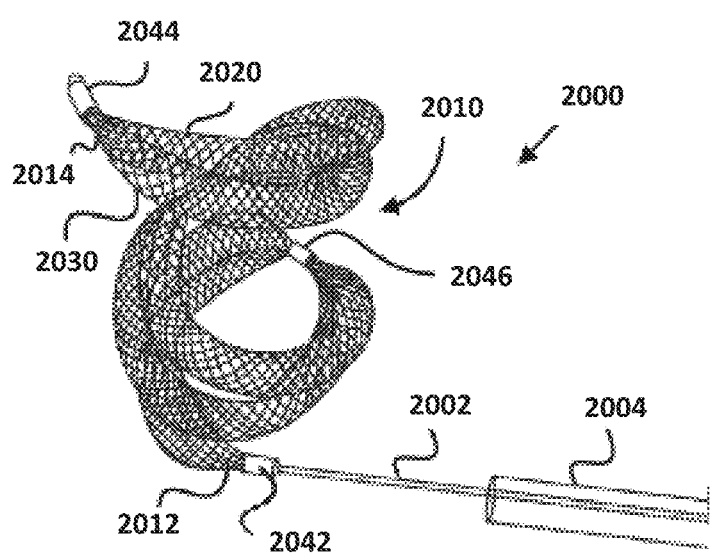

FIG. 20 illustrates another embodiment of a medical device. The medical device 2000 can include the same or similar features and functions as described above for previous embodiments. For example, the medical device 2000 includes an occlusion device 2010 and an insertion portion or member 2002. The medical device 2000 can be delivered to an aneurysm or other vascular defect using a microcatheter 2004. The occlusion device 2010 is sized to occupy at least a portion of the volume of the sac of the aneurysm, and the insertion member 2002 is configured to facilitate delivery of the occlusion device from the microcatheter 2004 into the sac of the aneurysm. The occlusion device 2010 is shown in an expanded configuration and can be moved between a compressed or collapsed configuration and the expanded configuration in the same or similar manner as described above for previous embodiments.

The occlusion device 2010 includes a first member 2020 and a second member 2030. The first and second members 2020, 2030 are coupled at a first end 2012 of the occlusion device 2010 and a second end 2014 of the occlusion device. The first and second members 2020, 2030 are also coupled together at at least one middle portion of the occlusion device 2010 between the first end 2012 and the second end 2014. The first and second members 2020, 2030 can be coupled, for example, using radiopaque markers 2042, 2044, 2046. Each site of coupling is configured to be a folding point of the occlusion device 2010 when the occlusion device is delivered into the aneurysm and is expanded within the aneurysm to comply with the shape of the aneurysm. As such, the occlusion device 2010 can be more densely packed into the aneurysm, for example, as compared to an implant that cannot bend or fold in response to the shape of the aneurysm. At least one of the first member 2020 and the second member 2030 of the occlusion device 2010 includes a porous mesh formed of a tubular or rounded braid structure.

Figure 21:
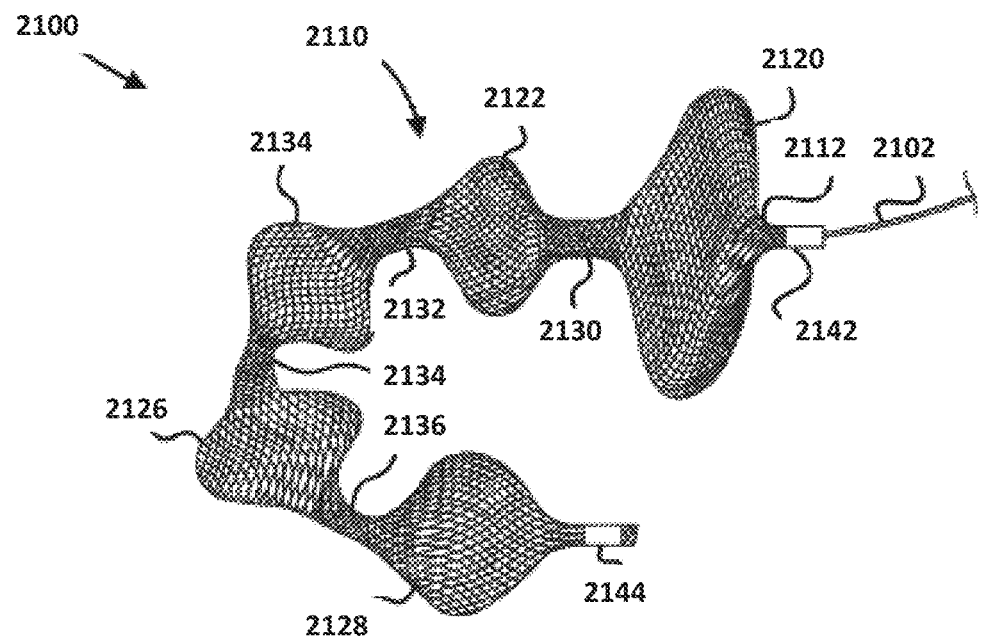

FIG. 21 illustrates another embodiment of a medical device. The medical device 2100 can include the same or similar features and functions as described above for previous embodiments. For example, the medical device 2100 includes an occlusion device 2110 and an insertion portion or member 2102. The occlusion device 2110 is sized to occupy the sac of the aneurysm, and the insertion member 2102 is configured to facilitate delivery of the occlusion device from a microcatheter (not shown in FIG. 21) into the sac of the aneurysm. The occlusion device 2110 is shown in an expanded configuration and can be moved between a compressed or collapsed configuration and the expanded configuration in the same or similar manner as described above for previous embodiments.

The occlusion device 2110 includes a series of expandable portions 2120, 2122, 2124, 2126, 2128 separated by a series of constricted portions 2130, 2132, 2134, 2136. The expandable portions 2120, 2122, 2124, 2126, 2128 can be configured to expand to any suitable multi-dimensional shape, including, for example, that resembling a sphere, a disc, a parabola, or the like. Additionally, each expandable portion 2120, 2122, 2124, 2126, 2128 can have an expanded shape distinct from an expanded shape of another expandable portion.

When the occlusion device 2110 is in its expanded configuration, as shown in FIG. 21, the expandable portions 2120, 2122, 2124, 2126, 2128 are more porous and less dense then the constricted portions 2130, 2132, 2134, 2136. The density and/or porosity of each expandable portion 2120, 2122, 2124, 2126, 2128 can be varied from the other expandable portions 2120, 2122, 2124, 2126, 2128, and the density and/or porosity of each expandable portion 2120, 2122, 2124, 2126, 2128 can be varied along a length and/or width of the respective expandable portion. For example, a first expandable portion 2120 can be more dense and/or less porous proximate to a first constriction portion 2130 and less dense and/or more porous at a middle, wider portion of the first expandable portion 2120. Additionally, the expandable portions 2120, 2122, 2124, 2126, 2128 are each configured to have a width greater than when the occlusion device 2110 is in its collapsed configuration, and the constricted portions 2130, 2132, 2134, 2136 are each configured to have a width narrower than a width of the expandable portions 2120, 2122, 2124, 2126, 2128. As such, the occlusion device 2110 is configured to bend, curve, and/or fold at the constricted portions 2130, 2132, 2134, 2136 to help comply with the shape of the aneurysm.

When the occlusion device 2110 is in its expanded configuration, the first expandable portion 2120 is configured to have a width greater than the width of the other expandable portions 2122, 2124, 2126, 2128. The first expandable portion 2120 can be, as illustrated in FIG. 21, the most proximal of the expandable portions 2120, 2122, 2124, 2126, 2128. The first expandable portion 2120 is configured to be positioned over a neck of the aneurysm when the occlusion device 2110 is disposed within the aneurysm in its expanded configuration. In this manner, the first expandable portion 2120 is configured to act as a flow disruptor at the neck of the aneurysm to help limit the flow of blood into the aneurysm from the parent blood vessel. The remaining, more distal, expandable portions 2122, 2124, 2126, 2128 are configured to be packed into the aneurysm to embolize the aneurysm.

The occlusion device 2110 includes a first radiopaque marker 2142 coupled to a first end 2112 of the implant and a second radiopaque marker 2144 coupled to a second end 2114 of the implant. The radiopaque markers 2142, 2144 are configured to be wholly disposed within the sac of the aneurysm when the occlusion device 2110 is disposed in the aneurysm in its expanded configuration.

Figure 22:
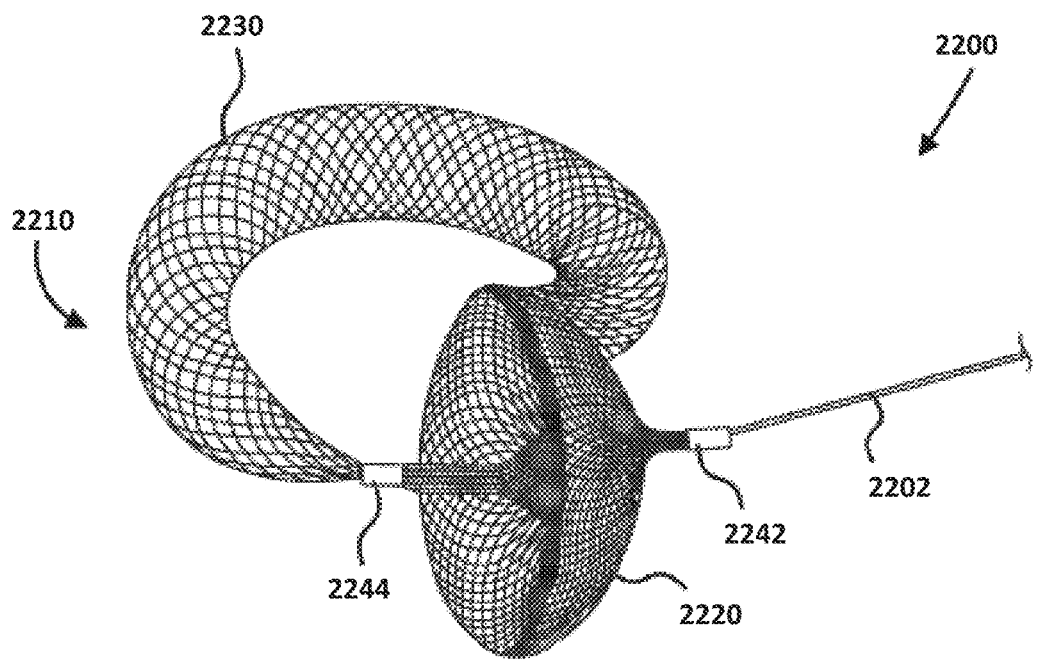

FIG. 22 illustrates another embodiment of a medical device. The medical device 2200 can include the same or similar features and functions as described above for previous embodiments. For example, the medical device 2200 includes an occlusion device 2210 and an insertion portion or member 2202. The occlusion device 2210 is sized to occupy the sac of the aneurysm, and the insertion member 2202 is configured to facilitate delivery of the occlusion device into the sac of the aneurysm. The occlusion device 2210 is shown in an expanded configuration and can be moved between a compressed or collapsed configuration and the expanded configuration in the same or similar manner as described above for previous embodiments.

The occlusion device 2210 includes a first porous member 2220 and a second porous member 2230. The first porous member 2220 includes a porous mesh configured to have a multi-dimensional shape when the occlusion device 2210 is in its expanded configuration. As such, the first porous member 2220 has a second width in the expanded configuration that is greater than a first width of the first porous member in the collapsed configuration. The first porous member 2220 can be configured to expand to any suitable multi-dimensional shape, including, for example, that resembling a parabola, as shown in FIG. 22, a sphere, a disc, or the like. The first porous member 2220 is configured to be positioned over a neck of the aneurysm when the expandable member 2210 is disposed within the sac of the aneurysm to disrupt and/or stop the flow of blood into the aneurysm from the parent blood vessel. Additionally, the porous mesh of the first porous member 2220 is configured to promote endothelial cell attachment at the neck of the aneurysm, which can help to heal over the neck of the aneurysm.

The second porous member 2230 includes a porous mesh configured to have a multi-dimensional shape when the occlusion device 2210 is in its expanded configuration. As such, the second porous member 2230 has a fourth width in the expanded configuration greater than a third width of the second porous member in the collapsed configuration. The second porous member 2230 can be configured to expand to any suitable multi-dimensional shape, including, for example, that resembling a tube, as shown in FIG. 22, a sphere, a disc, a parabola, or the like. In the embodiment illustrated in FIG. 22, the second width of the first porous member 2220 is greater than the fourth width of the second porous member 2230. The second porous member 2230 is configured to be disposed within the sac of the aneurysm such that the first porous member 2220 is disposed between the second porous member 2230 and the neck of the aneurysm. The second porous member 2230 is configured to be packed into the aneurysm to embolize the aneurysm.

A radiopaque marker 2244 is disposed between the first porous member 2220 and the second porous member 2230, and can be used to couple the first and second porous members. The occlusion device 2210 is configured to bend, curve, and/or fold at the radiopaque marker 2244, which can help the occlusion device 2210 comply with the shape of the sac of the aneurysm. Another radiopaque marker 2242 can be disposed on a proximate end of the occlusion device 2210, and can be used to couple the insertion portion 2202 to the occlusion device. The radiopaque markers 2242, 2244 are configured to be wholly disposed within the sac of the aneurysm when the occlusion device 2210 is disposed in the aneurysm in its expanded configuration.

Figure 23A:
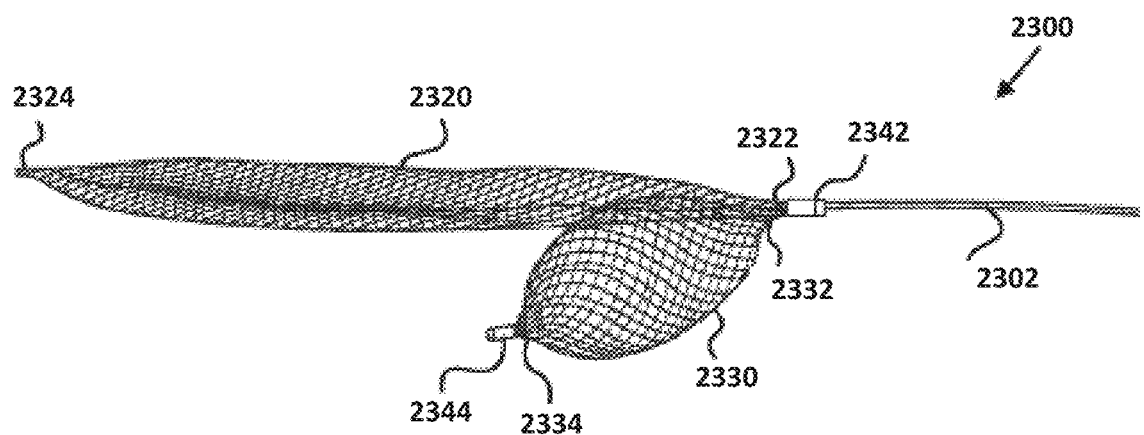
FIG. 23A is a view of a medical device in a partially collapsed configuration, according to an embodiment.
Figure 23B:
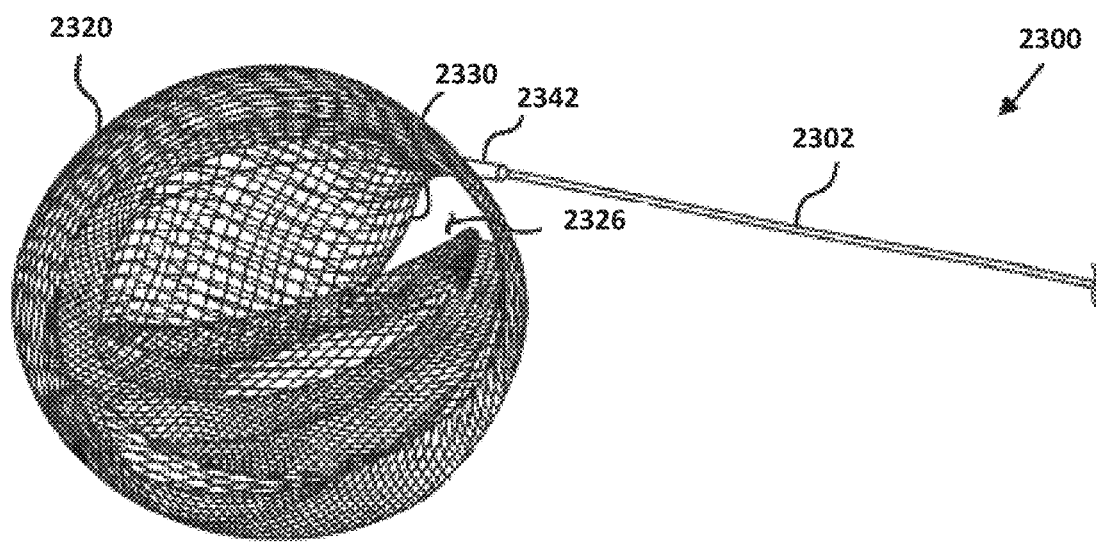
FIG. 23B is a view of the medical device of FIG. 23A in an expanded configuration, according to an embodiment.

FIGS. 23A and 23B illustrate another embodiment of a medical device. The medical device 2300 can include the same or similar features and functions as described above for previous embodiments. For example, the medical device 2300 includes a first porous member 2320, a second porous member 2330, and an insertion portion or member 2302 removably couplable to the first and second porous members 2320, 2330.

The first porous member 2320 has a first end 2322 and a second end 2324. As shown in FIG. 23A, the first porous member 2320 has a collapsed configuration for insertion through a blood vessel. In its collapsed configuration, the first porous member 2320 is substantially elongate with a first length. As shown in FIG. 14B, the first porous member 2320 has an expanded configuration for occupying a sac of an aneurysm. When the first porous member 2320 is in its expanded configuration, it has a three-dimensional shape and defines an open interior region 2326. The first porous member 2320 can have any suitable three-dimensional shape. For example, the first porous member 2320 can be configured to curve into a substantially spherical shape, as shown in FIG. 23B. Additionally, in its expanded configuration, the first porous member 2320 includes a first segment configured to overlap with a second segment, which can be similar in many respects as described above with respect to occlusion devices 1410 and 1510, for example. For example, the first porous member 2320 can include a mesh having a first segment configured to overlap with a second segment of the porous mesh to form a higher density portion of the first porous member 2320.

The second porous member 2330 has a first end 2332 and a second end 2334. The second porous member 2330 has a collapsed, first, configuration (not shown in FIG. 23A or 23B) for insertion through a blood vessel. In its collapsed configuration, the second porous member 2330 is substantially elongate with a second length less than the first length of the first porous member, and is configured to occupy a first volume. As shown in FIGS. 23A and 23B, the second porous member 2330 has an expanded, second, configuration for occupying at least a portion of the volume of the sac of the aneurysm. When the second porous member 2330 is in its expanded configuration, it has a three-dimensional shape and is configured to occupy a second volume greater than the first volume. The second porous member 2330 can have any suitable three-dimensional shape. For example, the second porous member 2330 can be configured to expand into a substantially ball (e.g., spherical, round, oblong, or the like) shape, as shown in FIGS. 23A and 23B. In the expanded configuration, the second porous member 2330 can have a porosity the same as, or different than, a porosity of the first porous member 2320. The second porous member 2330 is configured to be disposed in the interior region 2326 of the first porous member 2320 when each of the first porous member and the second porous member are in the deployed or expanded configurations.

In the embodiment illustrated in FIGS. 23A and 23B, the second porous member 2330 is coupled to the first porous member 2320. Specifically, the first end 2322 of the first porous member 2320 is coupled to the first end 2332 of the second porous member 2330. At least one of the first porous member 2320 and the second porous member 2330 includes a radiopaque marker. As shown in FIG. 23A, a first radiopaque marker 2342 can be disposed on the first ends 2322, 2332 of the first and second porous members 2320, 2330 to couple the first and second porous members together. A second radiopaque marker 2344 can be disposed on the second end 2334 of the second porous member 2330. When the first and second porous members 2320, 2330 are in their respective expanded configurations, the second radiopaque marker 2344 is disposed within the interior region defined by the first porous member 2320.

In use, the first and second porous members 2320, 2330, and the first and second radiopaque markers 2342, 23214, are wholly disposed within the aneurysm. The second porous member 2330 can be inserted into the aneurysm first and assume its expanded configuration therein. The first porous member 2320 can then be inserted into the aneurysm such that the first porous member curves, coils, or otherwise wraps around the second porous member 2330 as the first porous member moves to its expanded configuration. The first porous member 2320 is configured to be disposed within the aneurysm such that a portion of the first porous member is disposed over the neck of the aneurysm. For example, the higher density portion of the first porous member 2320 at which the first segment overlaps the second segment can be positioned over the neck of the aneurysm to promote endothelial cell attachment at the aneurysm neck. The second porous member 2330 can help to embolize the aneurysm by providing additional porous mesh within the sac of the aneurysm for cell attachment and/or clot formation. As such, the second porous member occupies a portion of the volume of the sac of the aneurysm such that blood flow through the aneurysm is further inhibited.

Although the medical device 2300 includes discrete first and second porous members 2320, 2330, respectively, in other embodiments, the first and second porous members can be differently constructed. For example, referring to FIG. 24, an embodiment of a medical device 1200 is illustrated. The medical device 2400 can include the same or similar features and functions as described above for medical device 2400, or other previous embodiments. For example, the medical device 2400 includes a first porous member 2420, a second porous member 2430, and an insertion portion or member (not shown in FIG. 24) removably couplable to the first and second porous members. Each of the first porous member 2420 and the second porous member 2430 can be similar in form and function as the first porous member 2320 and the second porous member 2330, respectively, described above.

Figure 24:
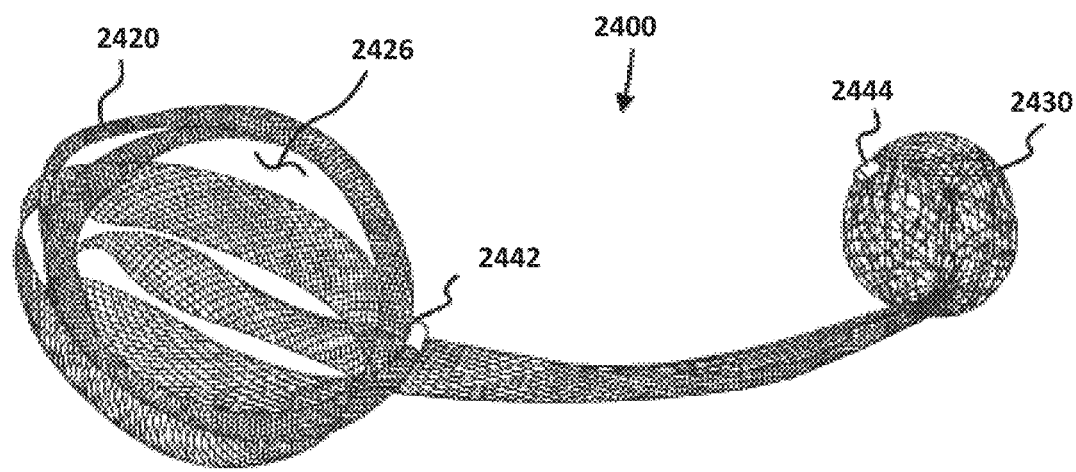
FIG. 24 is a view of a portion of a medical device in an expanded configuration according to an embodiment, with a first portion spaced apart from a second portion.

In the embodiment illustrated in FIG. 24, however, the second porous member 2430 is monolithically constructed with the first porous member 2420. It should be noted that in FIG. 24, the first and second porous members 2420, 2430, are shown in an expanded configuration but the second porous member 2430 is shown spaced apart from the first porous member 2420 for illustration purposes only. In use, in their respective deployed or expanded configurations, the second porous member 2430 is disposed within an interior region 2426 defined by the first porous member 2420 in a similar manner as that illustrated in FIG. 23 with respect to medical device 2300. Additionally, the medical device 2400 includes two radiopaque markers 2442, 2444. A first radiopaque marker 2442 is disposed at an end of a porous mesh of the first porous member 2420, and the second radiopaque marker 2444 is disposed at an opposing end of porous mesh of the second porous member 2430.

Figure 25A:
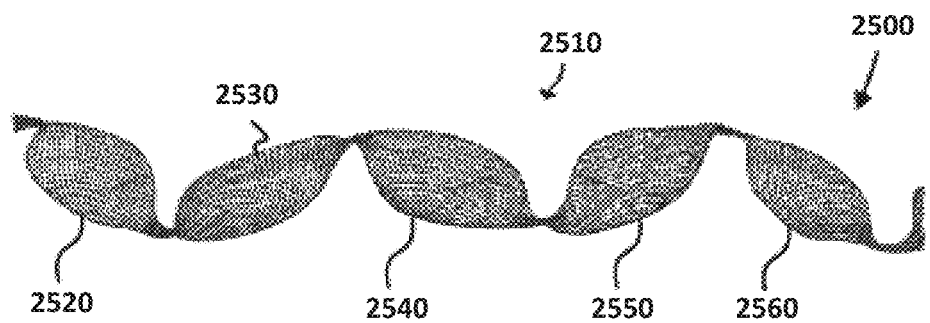
FIG. 25A is a view of a portion of a medical device in a collapsed configuration according to an embodiment.
Figure 25B:
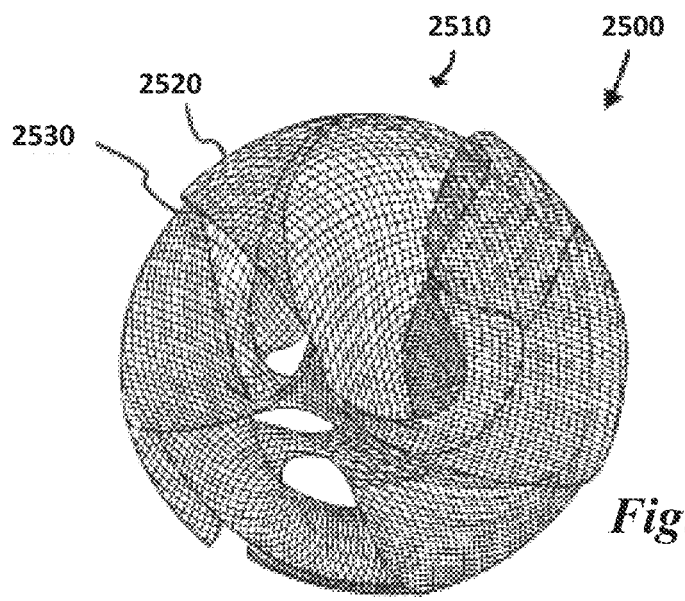
FIG. 25B is a view of a portion of a medical device in an expanded configuration according to an embodiment.

In some embodiments, a medical device includes an occlusion device that has a substantially continuous outer surface when in an expanded configuration. Referring to FIGS. 25A and 25B, a portion of a medical device 2500 according to an embodiment is illustrated in a collapsed configuration and an expanded configuration, respectively. The medical device 2500 can include the same or similar features and functions as described herein for other embodiments. For example, the medical device 2500 can include an occlusion device 2510 configured to move from the collapsed configuration (e.g., for delivery through a blood vessel) to the expanded configuration (e.g., for deployment within an aneurysm). The occlusion device 2510 includes at least a first portion 2520 and a second portion 2530, and can include additional portions 2540, 2550, 2560. When the occlusion device 2510 is in its expanded configuration, the occlusion device 2510 has a three-dimensional shape (e.g., a substantially spherical shape) with a substantially continuous outer surface such that edges of at least two of the portions 2520, 2530, 2540, 2550, 2560 overlap. For example, edges of the first portion 2520 and the second portion 2530 can overlap, as shown in FIG. 25B. In other words, the occlusion device 2510 moves into the expanded configuration such that few or no openings or spaces remain between edges of the portions 2520, 2530, 2540, 2550, 2560 of the occlusion device 2510.

Figure 26B:
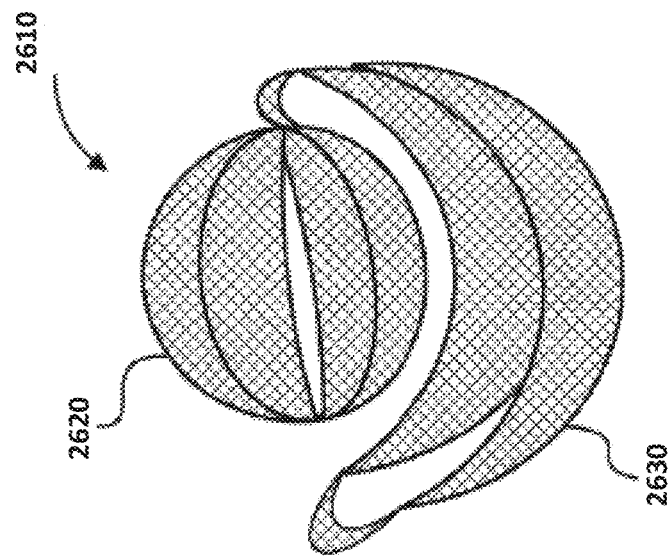
FIG. 26B is a schematic illustration of the medical device of FIG. 26A.
Figure 26A:
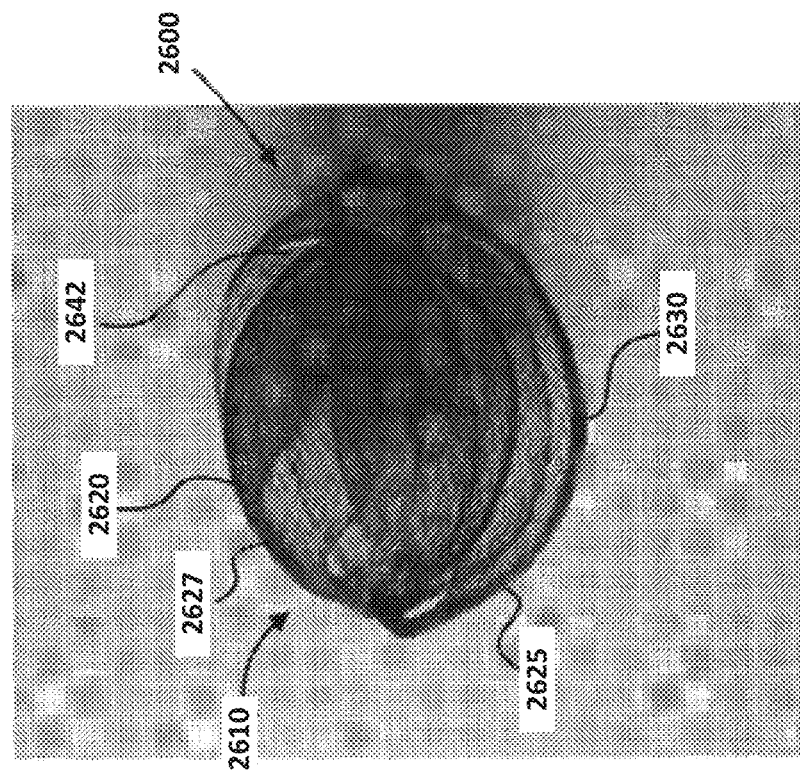
FIG. 26A is a view of a portion of a medical device in an expanded configuration, according to an embodiment.

FIG. 26A illustrates a portion of another embodiment of a medical device. The medical device 2600 can include the same or similar features and functions as described above for previous embodiments. For example, the medical device 2600 includes an occlusion device 2610 and an insertion portion or member (not shown in FIG. 26A). The occlusion device 2610 is shown in an expanded configuration and can be moved between a compressed or collapsed configuration in which the occlusion device 2610 is substantially elongate and the expanded configuration in the same or similar manner as described above for previous embodiments.

The occlusion device 2610 includes a ribbon-like strand of porous mesh and includes petal-like portions or sections 2625 and 2627 along its length. At least a portion of the porous mesh is configured to be positioned over a neck of an aneurysm when the occlusion device 2610 is in the expanded configuration. The occlusion device 2610 includes a first portion 2620 that includes the petal-like portions 2627 and a second portion 2630 that includes the petal-like portions 2627. The petal-like portions 2625 of the second portion 2630 are larger than the petal-like portions 2627 of the first portion 2620 such that when the occlusion device 2610 is moved to its expanded configuration, the petal-like portions 2625 of the second portion at least partially overlap the petal-like portions 2627 of the first portion 2620. During deployment of the occlusion device 2610 (e.g., when moved from its collapsed configuration to its expanded configuration) the petal-like portions 2625 of the second portion 2630 will deploy first, and then the petal-like portions 2627 of the first portion 2620 will deploy at least partially within an interior region defined by the second portion 2630. The petal-like portions 2625 of the second portion 2630 can be sized and configured to be disposed at a neck of an aneurysm when the occlusion device 2610 is in the expanded configuration. The petal-like portions 2627 of the first portion 2620 can be formed in a smaller diameter fixture than the petal-like portions 2625, and can be sized and configured to substantially fill the aneurysm and to hold the second portion 2630 in place at the neck of the aneurysm when the occlusion device 2610 is in the expanded configuration. For example, the petal-like portions 2627 of the first portion 2620 can have a diameter of about 2 mm-12 mm, and the petal-like portions 2625 of the second portion 2630 can have a corresponding diameter of about 1 mm larger than the petal-like portions 2627 of the first portion 2620. For example, the petal-like portions 2625 of the second portion 2630 can be about 3 mm-13 mm. FIG. 26B is a schematic illustration of the occlusion device 2610 in its expanded configuration showing the positional relationship of the first portion 2620 to the second portion 2630.

As described for previous embodiments, a first radiopaque marker 2642 is coupled to a first end of the occlusion device 2610 and a second radiopaque marker (not shown) is coupled to a second end of the occlusion device 2610. The occlusion device 2610 is configured to be wholly disposed within the aneurysm such that the radiopaque markers are wholly disposed within the aneurysm sac and the porous mesh is disposed over the neck of the aneurysm. In some embodiments, the radiopaque markers are configured to be positioned at a side of the aneurysm (i.e., disposed away from the neck of the aneurysm).

Figure 27:
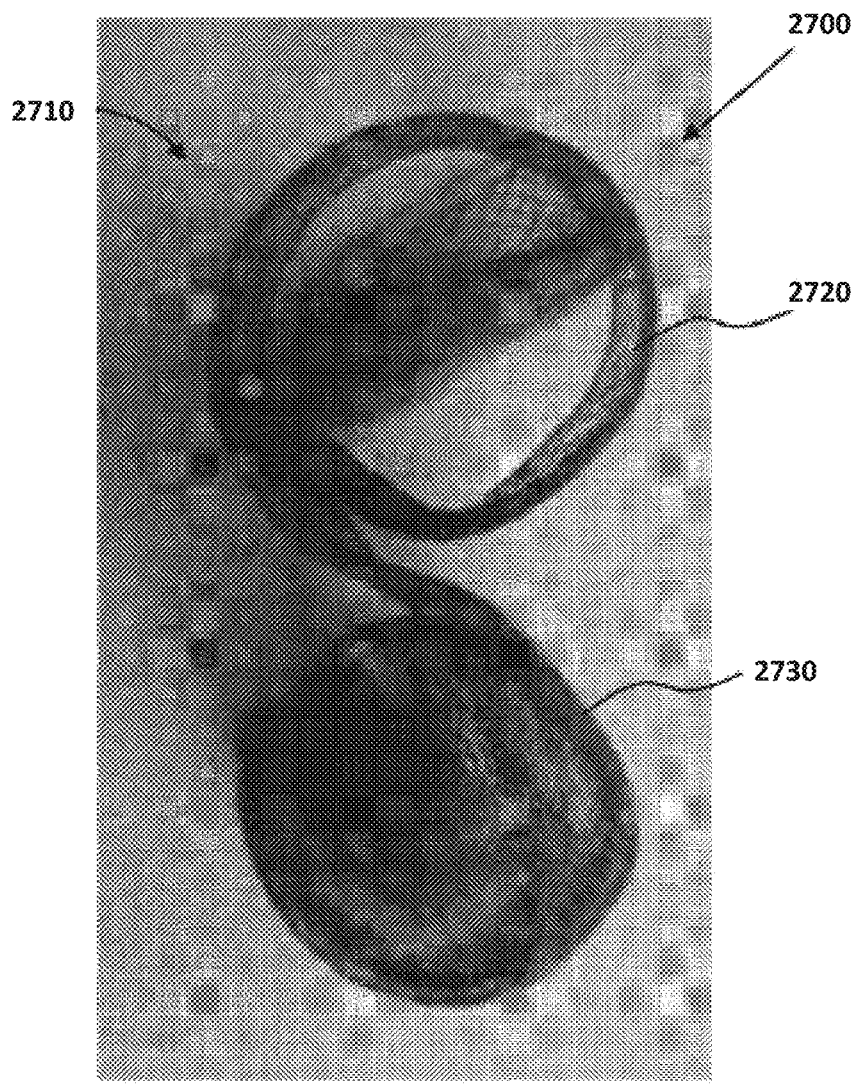
FIG. 27 is a view of a portion of a medical device in an expanded configuration, according to an embodiment.

FIG. 27 illustrates a portion of another embodiment of a medical device. The medical device 2700 can include the same or similar features and functions as described above for previous embodiments. For example, the medical device 2700 includes an occlusion device 2710 and an insertion portion or member (not shown in FIG. 27). The occlusion device 2710 is shown in an expanded configuration and can be moved between a compressed or collapsed configuration in which the occlusion device 2710 is substantially elongate and the expanded configuration in the same or similar manner as described above for previous embodiments.

As with the previous embodiment, the occlusion device 2710 includes a ribbon-like strand of porous mesh. At least a portion of the porous mesh is configured to be positioned over a neck of an aneurysm and at least another portion of the porous mesh substantially fills the volume of the aneurysm when the occlusion device 2710 is in the expanded configuration. The occlusion device 2710 includes a first portion 2720 and a second portion 2730. In this embodiment, each of the first portion 2720 and the second portion 2730 form a sphere when the occlusion device 2710 is in its expanded configuration. One of the first portion 2720 or the second portion 2730 can be configured to be disposed at a neck of the aneurysm and the other of the first portion 2720 or the second portion 2730 can substantially fill the volume of the aneurysm. For example, in this embodiment, the first portion 2720 can be configured to be deployed at the dome of an aneurysm and serve as an anchor for the second portion 2730 and the second portion 2730 can be disposed across the neck of the aneurysm when the occlusion device 2710 is in the expanded configuration. The occlusion device 2710 can also include radiopaque markers (not shown) as described above for previous embodiments.

Figure 28A:
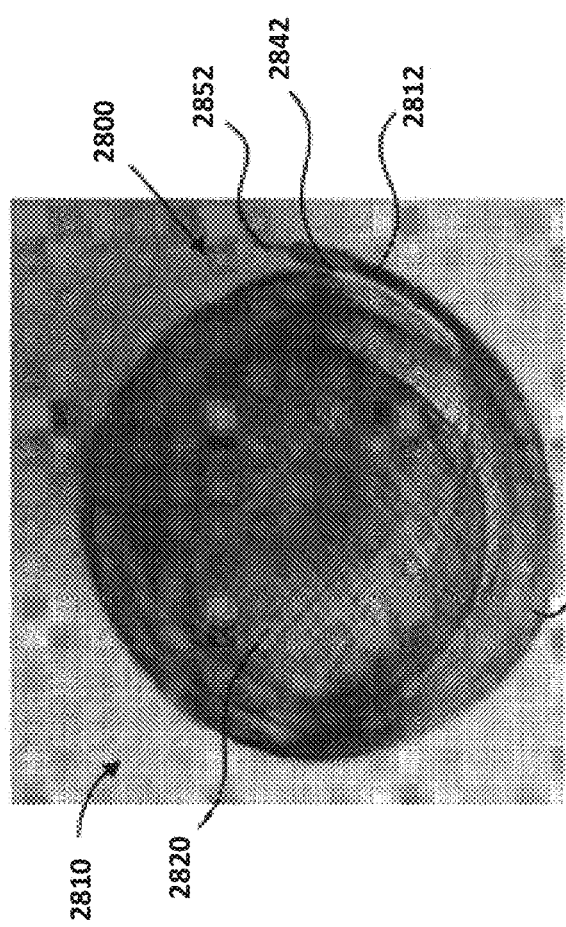
FIG. 28A is a view of a portion of a medical device in an expanded configuration, according to an embodiment.
Figure 28B:
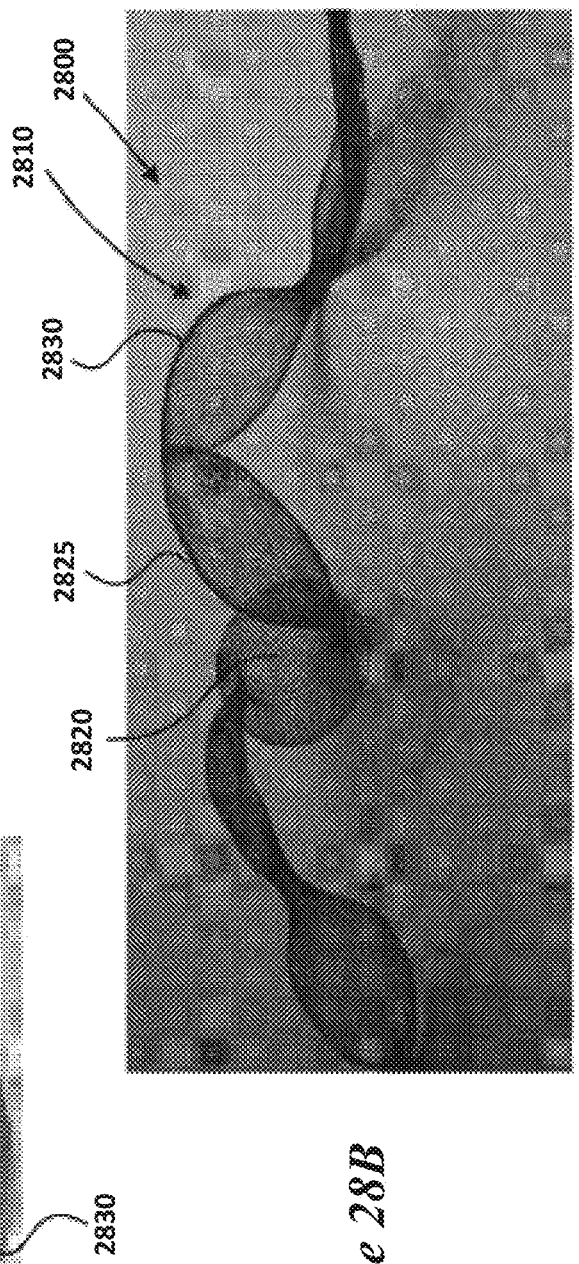
FIG. 28B is a view of a portion of the medical device of FIG. 28A in a collapsed configuration.

FIGS. 28A and 28B illustrate another embodiment of a medical device. The medical device 2800 can include the same or similar features and functions as described above for previous embodiments. For example, the medical device 2800 includes an occlusion device 2810 and an insertion portion or member (not shown). The occlusion device 2810 is shown in an expanded configuration and can be moved between a compressed or collapsed configuration as shown in FIG. 28B and the expanded configuration as shown in FIG. 28A in the same or similar manner as described above for previous embodiments.

As with the previous embodiment, the occlusion device 2810 includes a ribbon-like strand of porous mesh that includes a first portion 2820 in the form of a disc-shaped structure and a second portion 2830 that includes petal-like portions or sections along its length (similar to the embodiment of FIG. 26A). The disc or spherical shaped structure of the first portion 2820 can be disposed at various locations along the length (e.g., middle, end, etc.) of the occlusion device 2810. At least a portion of the porous mesh is configured to be positioned over a neck of an aneurysm when the occlusion device 2810 is in the expanded configuration. In this embodiment, when the occlusion device 2810 is in the expanded configuration, the petal-like portions of the second portion 2830 at least partially overlap the disc-shaped structure of the first portion 2820. For example, when the occlusion device 2810 is in its expanded configuration, the petal-like portions of the second portion 2830 can define a diameter greater than a diameter defined by the disc or spherical shaped structure of the first portion 2820. The occlusion device 2810 can also include a first radiopaque marker 2842 coupled to a first end 2812 of the occlusion device 2810 and a second radiopaque marker (not shown) coupled to a second end (not shown) of the occlusion device 2810. The occlusion device 2810 can also include a connector 2852 coupled to a first end 2812 of the occlusion device 2810.

When the occlusion device 2810 is in its expanded configuration, the occlusion device 2810 has a three-dimensional shape (e.g., a substantially spherical shape) with a substantially continuous outer surface such that edges of at least two of the petal-like portions 2825 overlap each other (in a similar manner as the embodiment of FIGS. 25A and 25B), and at least partially overlap the disc-shaped portion 2820. The occlusion device 2810 can move into the expanded configuration such that few or no openings or spaces remain between petal-like portions 2825 of the occlusion device 2810.

Figures 29A, 29B:
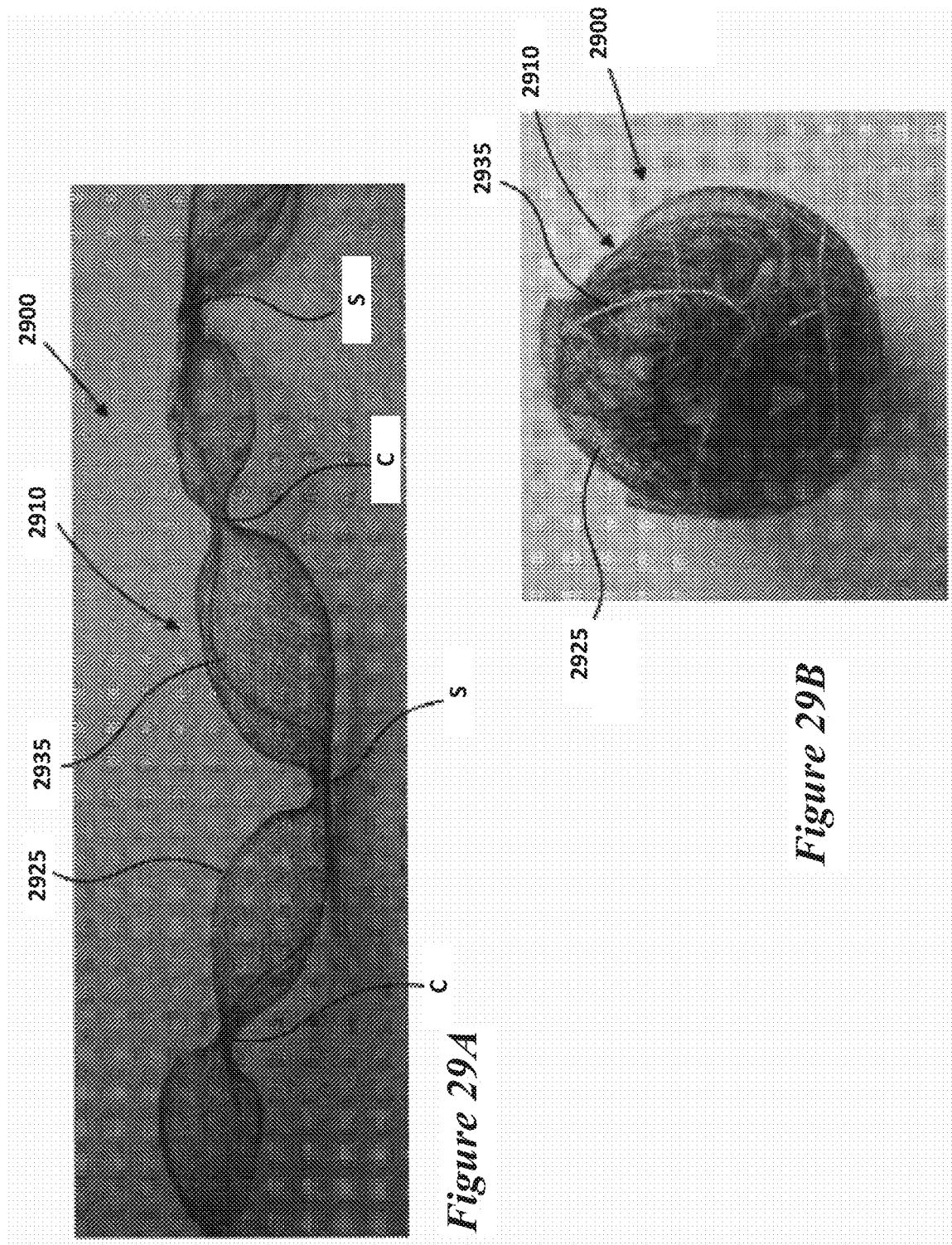
FIG. 29A is a view of a portion of a medical device in a collapsed configuration, according to another embodiment.
FIG. 29B is a view of the portion of the medical device of FIG. 29A in an expanded configuration.

FIGS. 29A and 29B illustrate a portion of another embodiment of a medical device. The medical device 2900 can include the same or similar features and functions as described above for previous embodiments. For example, the medical device 2900 includes an occlusion device 2910 and an insertion portion or member (not shown in FIGS. 29A and 29B). The occlusion device 2910 can be moved between a collapsed configuration as shown in FIG. 23 and an expanded configuration as shown in FIG. 24.

Similar to the embodiment of FIG. 26A, the occlusion device 2910 includes a ribbon-like strand of porous mesh that includes petal-like portions or sections 2925 along its length. At least a portion of the porous mesh is configured to be positioned over a neck of an aneurysm when the occlusion device 2910 is in the expanded configuration. When the occlusion device 2910 is in its expanded configuration, the occlusion device 2910 has a three-dimensional shape (e.g., a substantially spherical shape) with a substantially continuous outer surface such that edges of at least two of the petal-like portions 2925 overlap each other as shown in FIG. 29B.

In this embodiment, when the implantable implant 2910 is formed, the ribbon-like strand of porous mesh is wrapped around the forming fixture in a multi-directional fashion. For example, a portion of the mesh can be wrapped in a continuous manner around the fixture as indicated at C in FIG. 29A, and a portion of the mesh can be wrapped in an s-shape manner as indicated at S in FIG. 29A. With such forming, when the occlusion device 2910 is moved to its expanded configuration, the petal-like portions 2925 that have been formed by wrapping in a continuous manner will follow each other (each petal-like portion 2925 will cause the adjacent petal-like portion 2925 to collapse), and the petal-like portions 2925 that have been formed in a s-shape manner will individually self-deploy or collapse. The multi-directional heat forming of the occlusion device 2910 can allow the occlusion device 2910 to deploy fragmented within an aneurysm.

In this embodiment, the medical device 2900 also includes a PT coil or PT strand 2935 disposed along the length of the occlusion device 2910 to provide for a portion of the occlusion device 2910 to be radiopaque. As shown in FIG. 29A, the PT strand 2935 is disposed along a length of the occlusion device 2910 and across or within the petal-like portions 2925. The PT strand 2935 can be coupled to, for example, marker bands (not shown) disposed on a proximal end and a distal end of the occlusion device 2910. In some embodiments, a PT strand 2935 can be braided within the mesh of the occlusion device 2910.

In some embodiments, the PT strand 2935 can also be used to prevent over-stretching of the occlusion device 2910 when being delivered to a treatment site. For example, as described above, the PT strand 2935 can be coupled to the proximal end and the distal end of the occlusion device 2910. Thus, the PT strand 2935 can define a maximum length in which the occlusion device 2910 can be stretched or extended lengthwise during insertion and prevent over-stretching. In alternative embodiments, a separate component can be used to limit the length of the occlusion device 2910. For example, in some embodiments, a separate wire member in addition to a PT strand can be used. In some embodiments, an occlusion device may not include a PT strand, such as PT strand 2935. In such embodiments, a separate wire member can be coupled to the proximal end and distal end of the expandable member and used to limit the length or amount of stretch of the occlusion device in a similar manner.

In some embodiments, a medical device can include a strand formed with, for example, a suture that extends along or within the medical device. The suture strand can reinforce the medical device along its length. In some embodiments, a radiopaque coil can be placed over the suture strand to enhance visibility of the medical device under fluoroscopy.

Figures 30A, 30B:
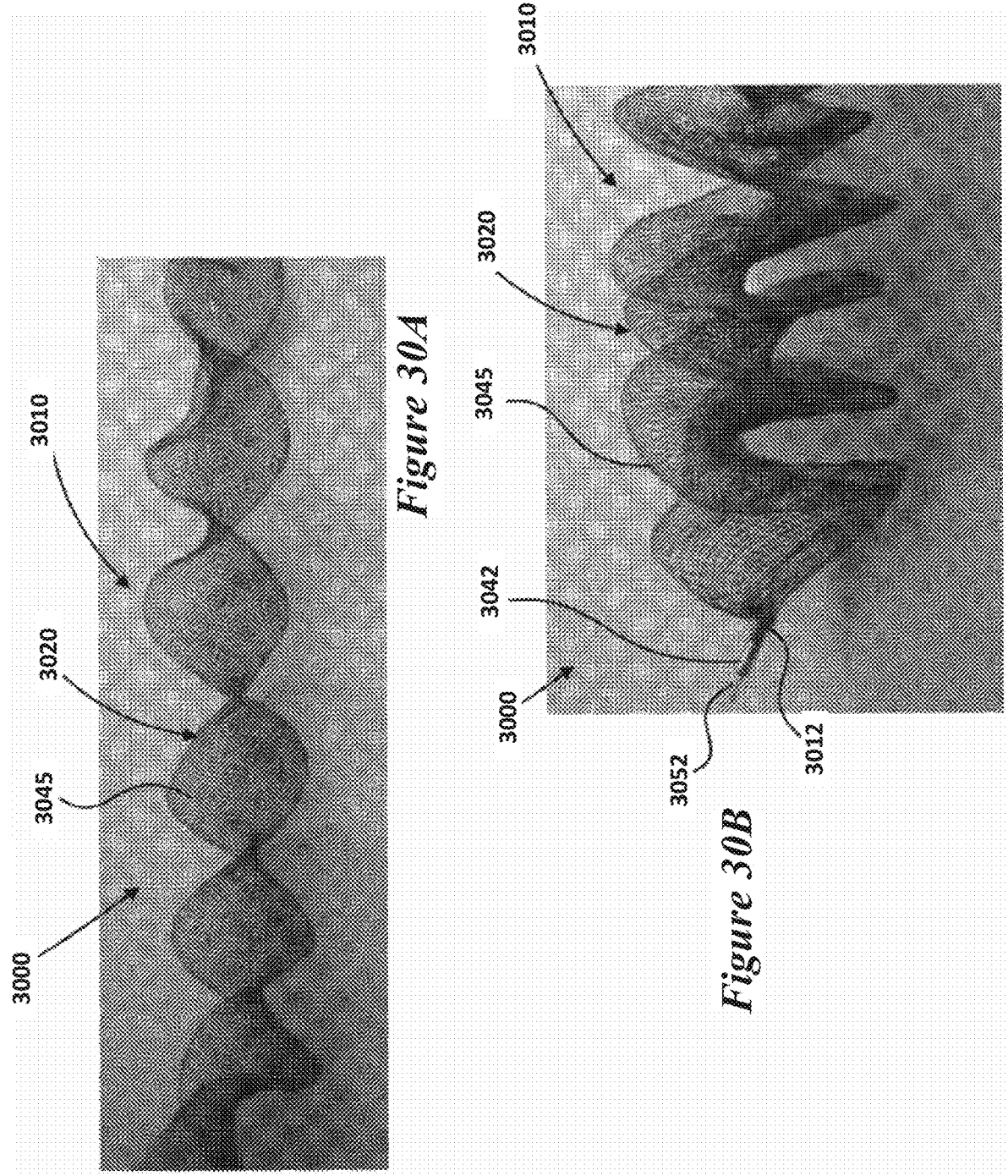
FIG. 30A is a view of a portion of a medical device in a collapsed configuration, according to an embodiment.
FIG. 30B is a view of the portion of the medical device of FIG. 30A in a partially expanded configuration.
Figure 30C:
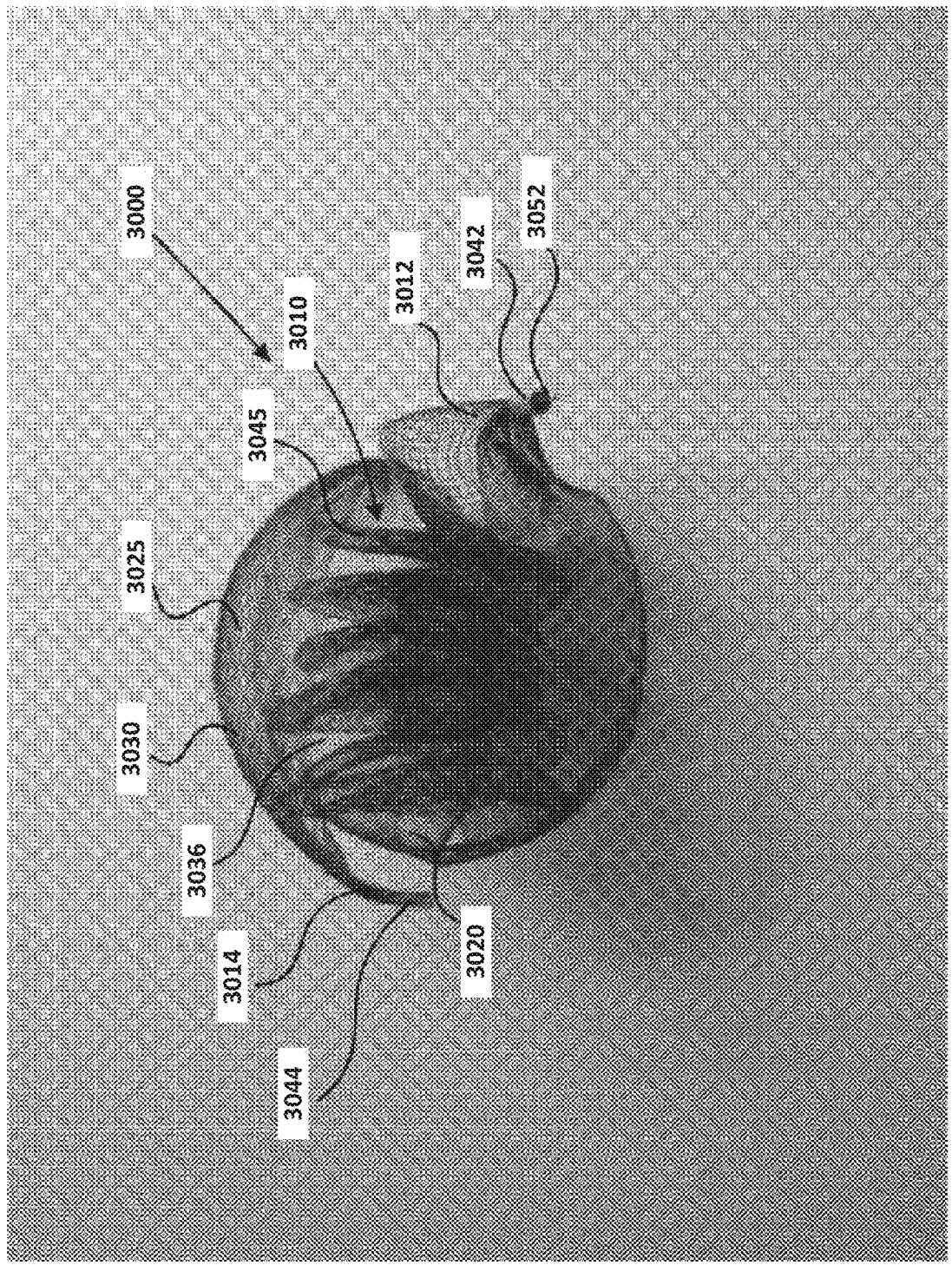
FIG. 30C is a view of a portion of the medical device of FIG. 30A in an expanded configuration.

FIGS. 30A-30C illustrate a portion of another embodiment of a medical device. The medical device 3000 can include the same or similar features and functions as described above for previous embodiments. For example, the medical device 3000 includes an occlusion device 3010 and an insertion portion or member (not shown in FIGS. 30A-30C). The occlusion device 3010 can be moved between a collapsed configuration (as shown in FIG. 30A, a partially expanded configuration as shown in FIG. 30B, and an expanded configuration as shown in FIG. 30C.

The occlusion device 3010 includes a ribbon-like strand of porous mesh that includes a first portion 3020 (see FIGS. 30A-30C) and a second portion 3030 (shown only in FIG. 30C). In this embodiment, the first portion 3020 and the second portion 3030 are separate components that can be deployed together. The first portion 3020 includes disc-shaped portions 3045 along its length, and the second portion 3030 includes petal-like portions 3025, as described above for previous embodiments. When the occlusion device 3010 is in its expanded configuration, the occlusion device 3010 has a three-dimensional shape (e.g., a substantially spherical shape) as shown in FIG. 30A.

During deployment of the medical device 3000, the second portion 3030 can be deployed first such that the petal-like portions 3025 are moved to an expanded configuration and define an interior region 3036. The first portion 3020 can then be deployed such that the disc-shape portions 3045 will collapse upon each other (as shown in FIGS. 30B and 30C) within the interior region 3036 of the second portion 3030, as shown in FIG. 30C. In other words, when the occlusion device 3010 is in the expanded configuration, the second portion 3030 at least partially overlaps the first portion 3020, as shown in FIG. 30C. At least a portion of the porous mesh is configured to be positioned over a neck of an aneurysm when the occlusion device 3010 is in the expanded configuration. For example, when the occlusion device 3010 is in its expanded configuration, the second portion 3030 can be disposed at the neck of the aneurysm to disrupt blood flow, and the first portion 3020 can help occlude the aneurysm at a relatively fast rate. Although this embodiment illustrates the first portion 3020 and the second portion 3030 as separate components, in an alternative embodiment, the first portion 3020 and the second portion 3030 can be formed with a single mesh component.

In this embodiment, the medical device 3000 can also include a PT coil or PT strand (not shown) disposed along the length of first portion 3020 and/or the second portion 3030 of the occlusion device 3010 in a similar manner as described above for medical device 2900. The PT strand can be coupled to a first marker band 3042 disposed at a first end 3012 of the occlusion device 3010 and a second marker band 3044 disposed on a second end of the occlusion device 3010 as shown in FIG. 30C. As described above, the PT strand can be braided within the mesh of the occlusion device 3010. As shown in FIGS. 30B and 30C, the expandable member 3010 also includes a connector member 3052 that can be used to couple the expandable member 3010 to a delivery device.

Figure 31A:
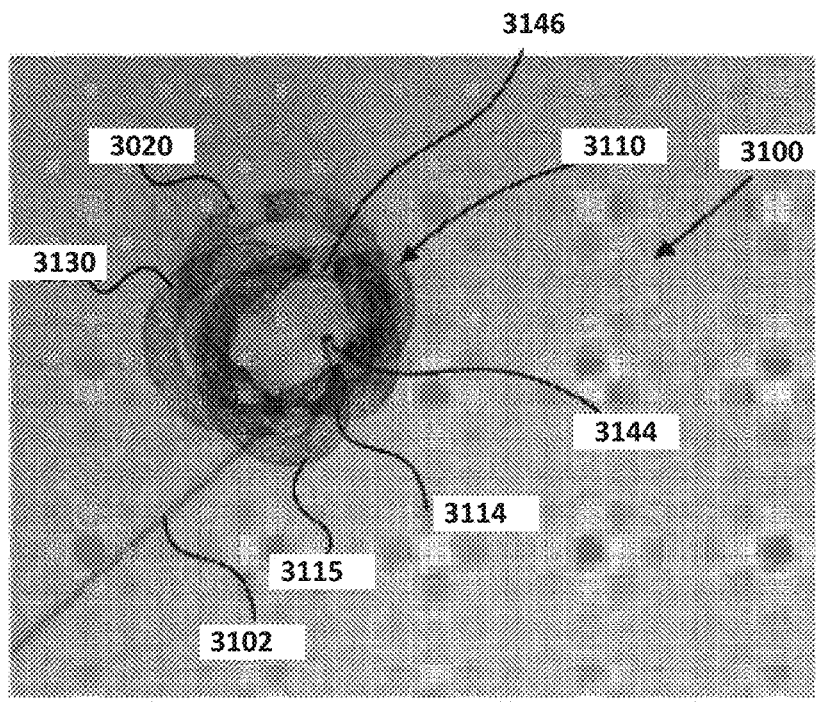
FIGS. 31A and 31B are each a different view of a portion of a medical device in an expanded configuration, according to an embodiment.
Figure 31B:
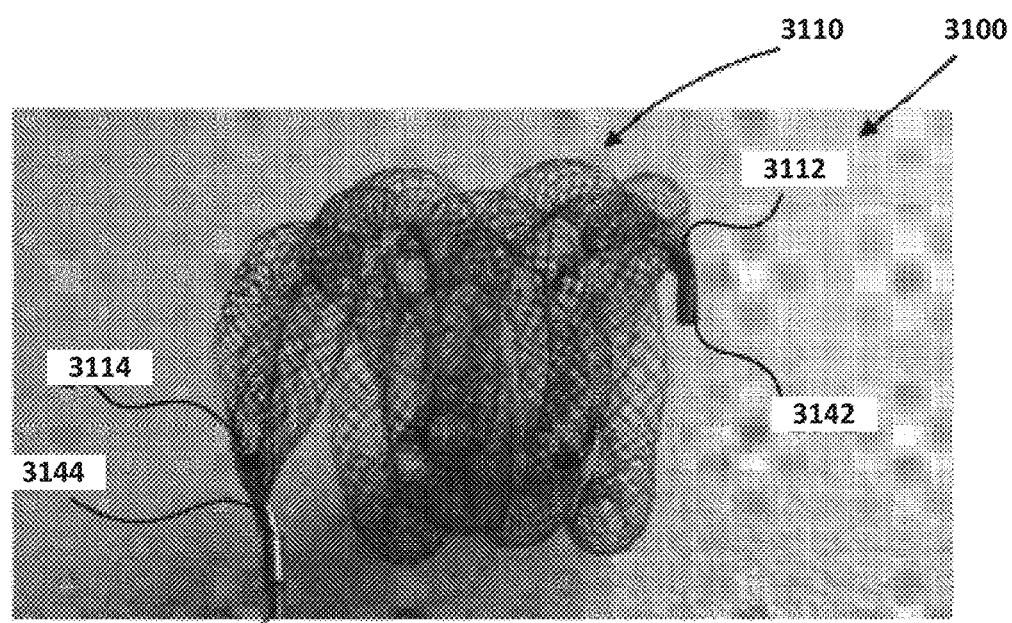

FIGS. 31A and 31B illustrate another embodiment of a medical device. A medical device 3100 can include all the same or similar features and functions as described above for previous embodiments. For example, the medical device 3100 includes an occlusion device 3110, an insertion portion or member 3102, a first radiopaque marker 3142 coupled to a first end 3112 of the occlusion device 3110 and a second radiopaque marker 3144 coupled to a second end 3114 of the occlusion device 3110. The occlusion device 3110 can be moved between a collapsed configuration (not shown) and an expanded configuration as shown in FIGS. 31A and 31B.

In this embodiment, the occlusion device 3110 includes three tubular or rounded strands 3120, 3130 and 3115 formed of a porous mesh similar to the tubular structures described above, for example, with respect to FIGS. 19 and 20. In some embodiments, the strands 3120, 3130 and 3115 can be braided. In alternative embodiments, the strands 3120, 3130 and 3115 can be formed with ribbon-like strands of porous mesh rather than tubular strands. When the occlusion device 3110 is in its expanded configuration, at least a portion of the tubular strands 3120, 3130 and 3115 can overlap each other as shown in FIG. 31B. The occlusion device 3110 can be used to fill a volume of an aneurysm and can be used alone or in conjunction with another occlusion device to fill the volume of an aneurysm.

The tubular mesh can be, for example, 1 mm tubular mesh. In this embodiment, the tubular strands 3120, 3130, 3115 can be heat-shaped such that the occlusion device 3110 has a 2D configuration when the occlusion device 3110 is in its expanded configuration. In this embodiment, three tubular strands are included, but in alternative embodiments a different number of tubular strands can be included. For example, an occlusion device can be formed with 1-10 tubular strands. The tubular strands 3120, 3130 and 3115 can be coupled together at various locations along their lengths with marker bands, such as marker band 3146 shown in FIG. 31B. In alternative embodiments, the tubular strands can be twisted together, or braided together rather than using marker bands. In some embodiments, the strands are not coupled together.

Figure 32:
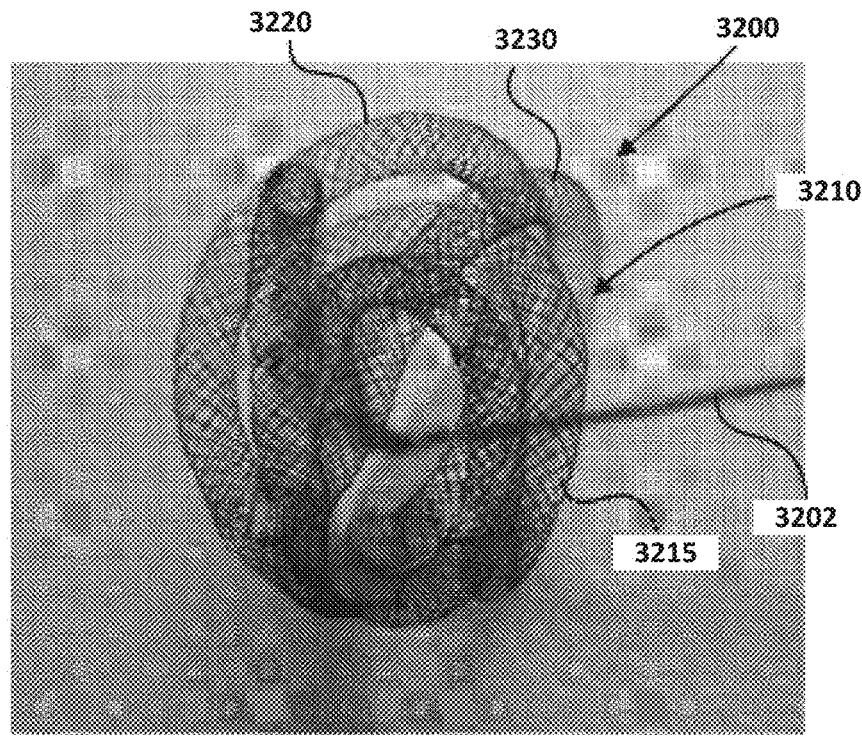
FIGS. 32 and 33 are each a view of a portion of a medical device in an expanded configuration, according to different embodiments.

FIG. 32 illustrates another embodiment of a medical device including tubular structures. A medical device 3200 can include all the same or similar features and functions as described above for previous embodiments. For example, the medical device 3200 includes an occlusion device 3210 and an insertion portion or member 3202. Although not shown in FIG. 32, the medical device 3200 can also include radiopaque markers coupled to end portions to the occlusion device 3210. The occlusion device 3210 can be moved between a collapsed configuration (not shown) and an expanded configuration as shown in FIG. 32.

The occlusion device 3210 includes three tubular or rounded strands 3220, 3230 and 3215 formed of a porous mesh similar to the tubular strands described above for medical device 2000. When the occlusion device 3210 is in its expanded configuration, at least a portion of the tubular strands 3220, 3230 and 3215 can overlap each other as shown in FIG. 32. In this embodiment, the tubular strands 3220, 3230, 3215 can be heat-shaped to have a 3D configuration when the occlusion device 3210 is in the expanded configuration. In this embodiment, three tubular strands are included, but in alternative embodiments a different number of tubular strands can be included. For example, an occlusion device can be formed with 1-10 tubular strands. The tubular strands 3220, 3230 and 3215 can be coupled together at various locations along their lengths with marker bands (not shown) as described above for medical device 3100, or can be coupled using other coupling methods, such as being twisted together, or braided together. In some embodiments, the tubular strands are not coupled together.

Figure 33:
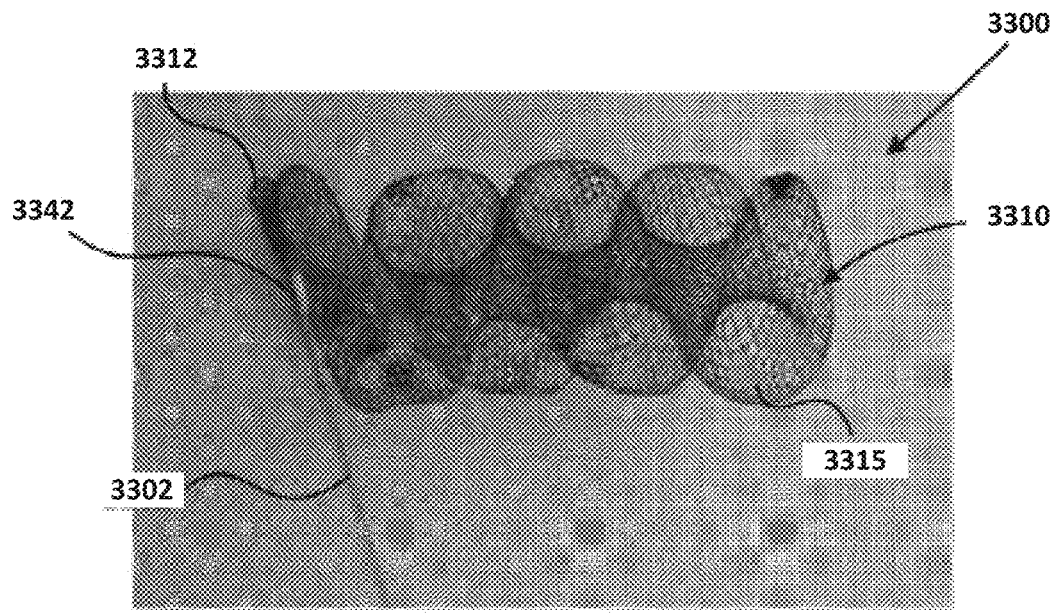

FIG. 33 illustrates another embodiment of a medical device including tubular structures. A medical device 3300 can include all the same or similar features and functions as described above for previous embodiments. For example, the medical device 3300 includes an occlusion device 3310 and an insertion portion or member 3302. Although not shown in FIG. 33, the medical device 3300 can also include radiopaque markers coupled to end portions to the occlusion device 3310, such as radiopaque marker 3342 coupled to an end 3312 shown in FIG. 33. The occlusion device 3310 can be moved between a collapsed configuration (not shown) and an expanded configuration as shown in FIG. 33.

In this embodiment, the occlusion device 3310 includes a single tubular or rounded braid structure 3315 formed of a porous mesh similar to the tubular structures described above for medical devices 2000 and 2100. When the occlusion device 3310 is in its expanded configuration, at least a first portion of the tubular structure 3315 can overlap a second portion of the tubular structure 3315, as shown in FIG. 33. In this embodiment, the tubular structure 3315 is formed in a 2D shape configuration and the tubular structure is formed with a larger porosity mesh than medical devices 2000 and 2100. For example, the tubular structure 3315 can be formed with a 3 mm mesh.

Figure 34A:
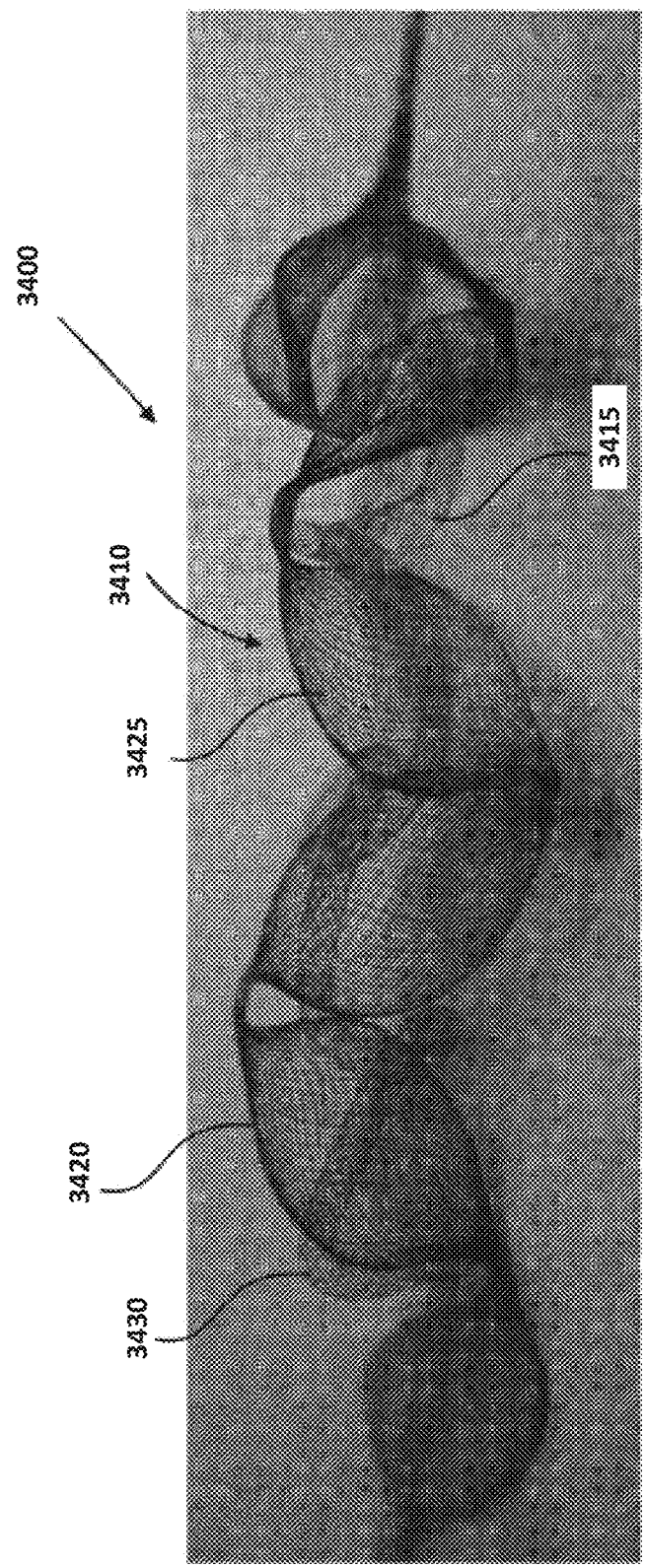
FIG. 34A is a view of a portion of a medical device in a collapsed configuration, according to an embodiment.
Figure 34B:
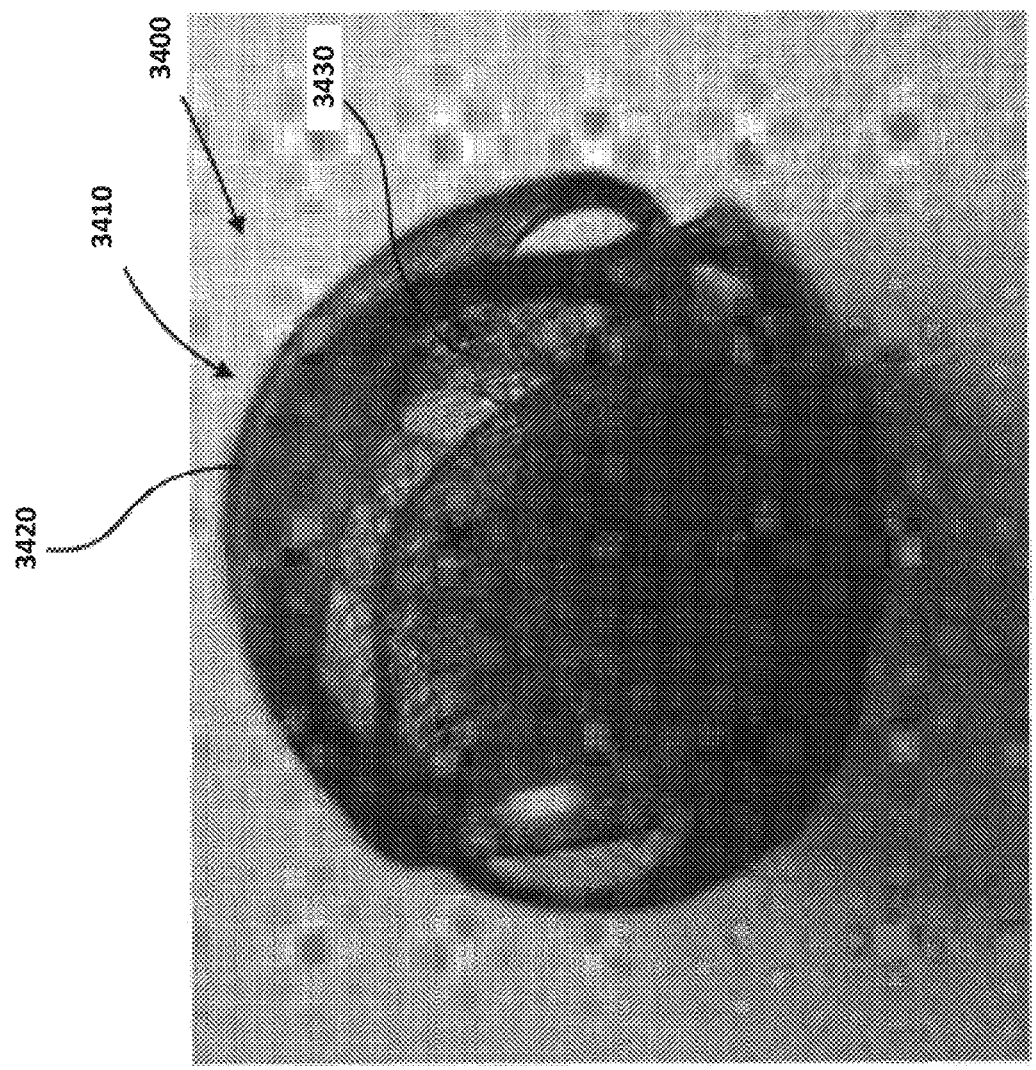
FIG. 34B is a view of the portion of the medical device of FIG. 34A, shown in an expanded configuration.

FIGS. 34A and 34B illustrate a portion of another embodiment of a medical device. The medical device 3400 can include the same or similar features and functions as described above for previous embodiments. The medical device 3400 includes an occlusion device 3410 and can include an insertion portion or member (not shown in FIGS. 34A and 34B). The occlusion device 3410 can be moved between a collapsed configuration as shown in FIG. 34A and an expanded configuration as shown in FIG. 34B.

In this embodiment, the occlusion device 3410 includes a first portion 3420 formed with a ribbon-like strand of porous mesh and includes petal-like portions 3425, and a second portion 3430 in the form of a tubular or rounded strand 3415 formed of a porous mesh similar to the tubular strands described above, for example, with respect to FIGS. 31A, 31B and 32. The tubular strand 3415 can be heat formed as either a 2D or 3D configuration. In some embodiments, the tubular strand 3415 can be braided.

When the occlusion device 3410 is in its expanded configuration, at least a portion of the first portion 3420 (e.g., petal-like portions 3425) can overlap the tubular strand 3415 of the second portion 3430. At least a portion of the occlusion device 3410 is configured to be positioned over a neck of an aneurysm when the occlusion device 3410 is in the expanded configuration. The petal-like portions 3425 and the tubular strand 3415 can each be a variety of different sizes (e.g., diameters), such that when the occlusion device 3410 is moved to its expanded configuration, the petal-like portions 3425 of the second portion 3410 define an interior region and the tubular strand 3415 of the first portion 3420 substantially fills the interior region of the second portion 3430. Thus, the tubular strand 3415 can be used as a filler to substantially fill a volume of an aneurysm as described above for occlusion devices 3110 and 3210.

The first portion 3420 and the second portion 3430 can be coupled together, for example, with marker bands at end portions of the first portion 3420 and the second portion 3430 and/or at other locations along a length of each of the first portion 3420 and the second portion 3430. The first portion 3420 and the second portion 3430 can have the same or substantially the same length or can have different lengths. For example, in some embodiments, the second portion 3430 can be longer than the first portion and vice versa.

Figure 34C:
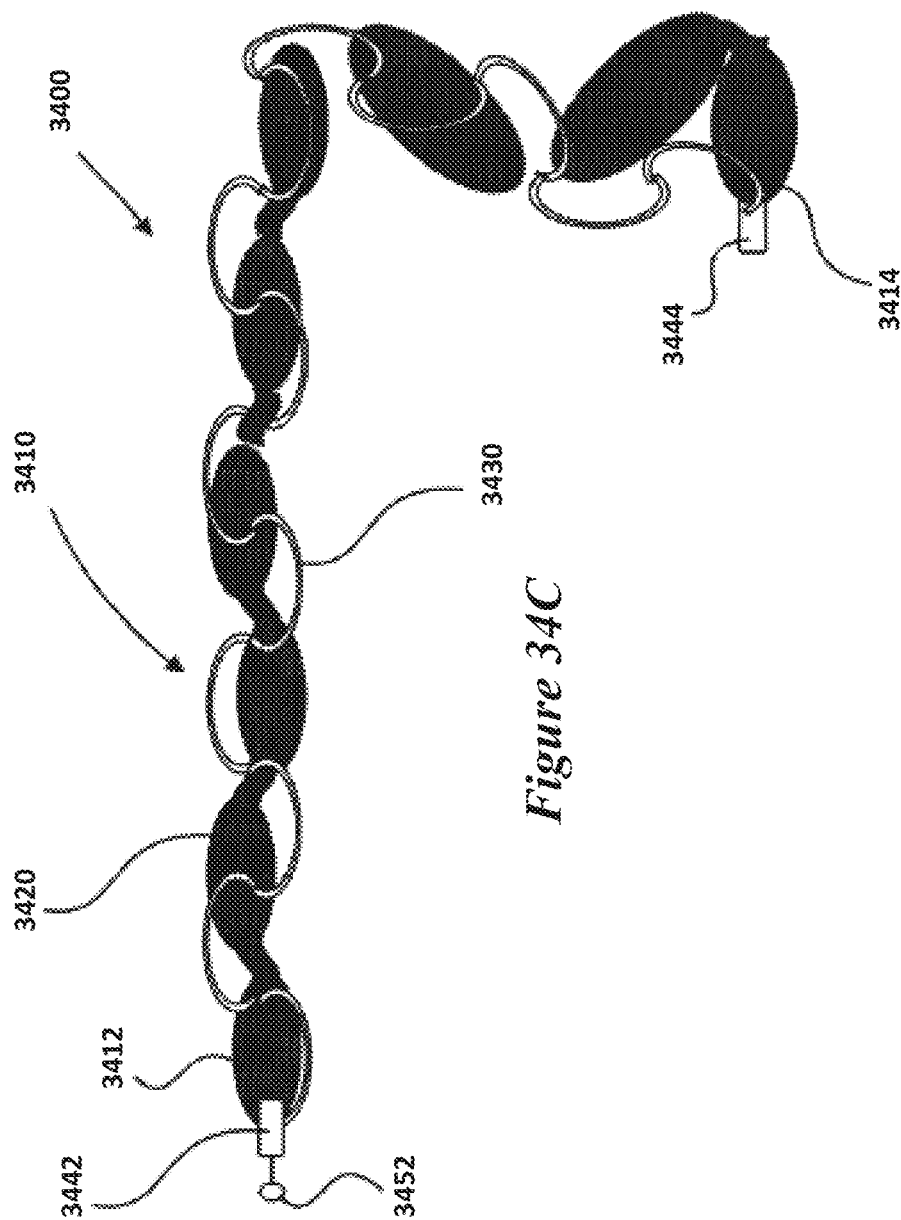
FIG. 34C is a schematic illustration of the portion of the medical device of FIG. 34B.

The occlusion device 3410 also includes a first radiopaque marker band 3442 disposed at a first end 3412 of the expandable member and a second radiopaque marker band 3444 disposed at a second end 3414 of the occlusion device 3410 as shown in FIG. 34C, which is a schematic illustration of the occlusion device 3410. As shown in FIG. 34C, which is a schematic illustration of the occlusion device 3410, the expandable member 3410 also includes a connector member 3452 that can be used to couple the expandable member to a delivery device.

Figures 35A, 35B:
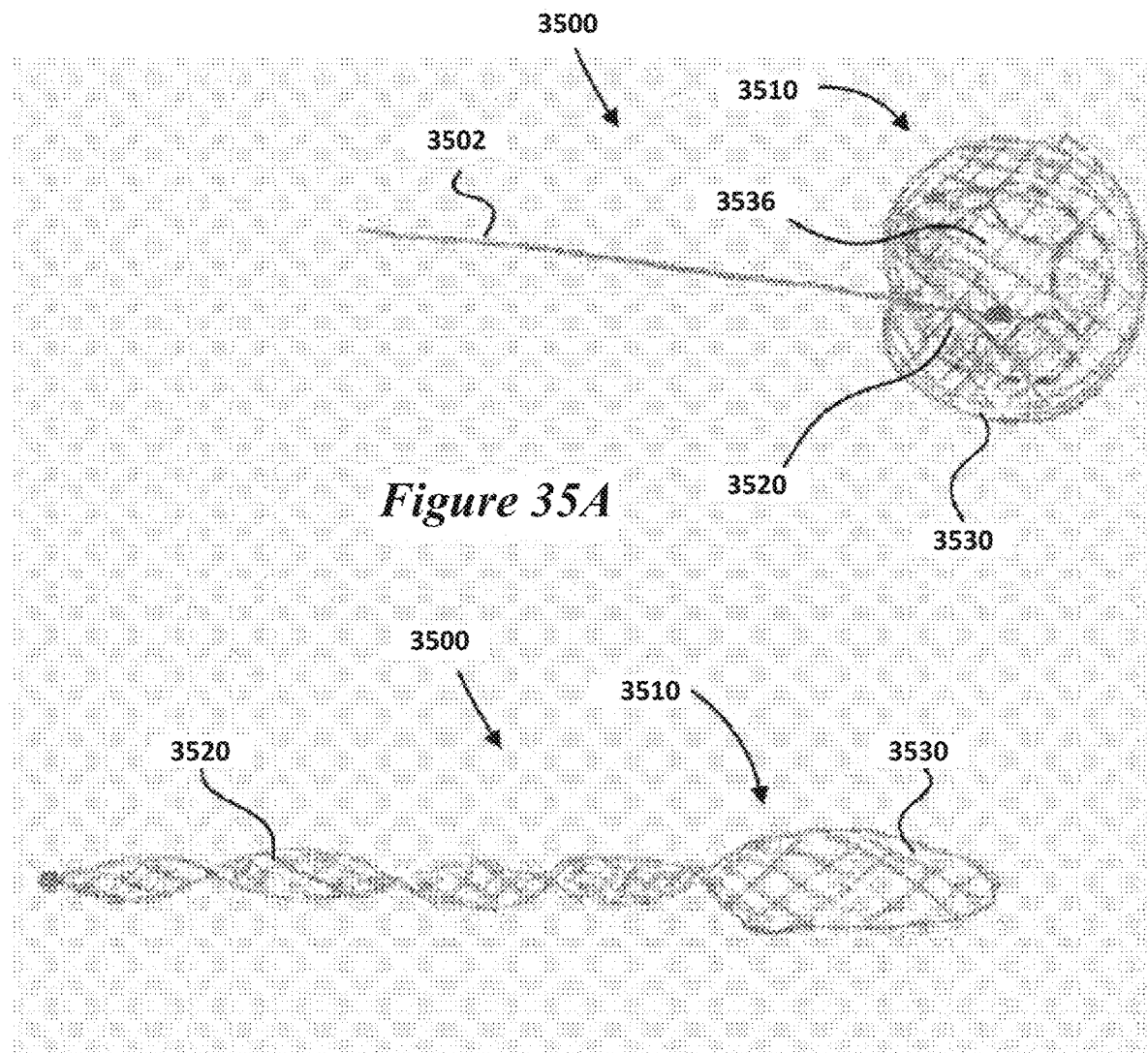
FIG. 35A is a view of a portion of a medical device in an expanded configuration, according to an embodiment.
FIG. 35B is a view of a portion of the medical device of FIG. 35A in a collapsed configuration.

FIGS. 35A and 35B illustrate a portion of another embodiment of a medical device. The medical device 3500 can include the same or similar features and functions as described above for previous embodiments. For example, the medical device 3500 includes an occlusion device 3510 and an insertion portion or member 3502. The occlusion device 3510 can be moved between a collapsed configuration, as shown in FIG. 35B and an expanded configuration, as shown in FIG. 35A.

The occlusion device 3510 includes a ribbon-like strand of porous mesh that includes a first portion 3520 and a second portion 3530 formed as a single component. In this embodiment, when the occlusion device 3510 is in the expanded configuration, the second portion 3530 forms a ball-like structure that defines an interior region 3536 and the first portion 3520 can be deployed within the interior region 3536. Specifically, during deployment of the medical device 3500, the second portion 3530 can be deployed first such that it can be expanded to the ball-shaped structure within an aneurysm, and then the first portion 3520 can be deployed within the interior region 3536 to substantially fill the second portion 3530 as shown in FIG. 35A.

Figure 36A:
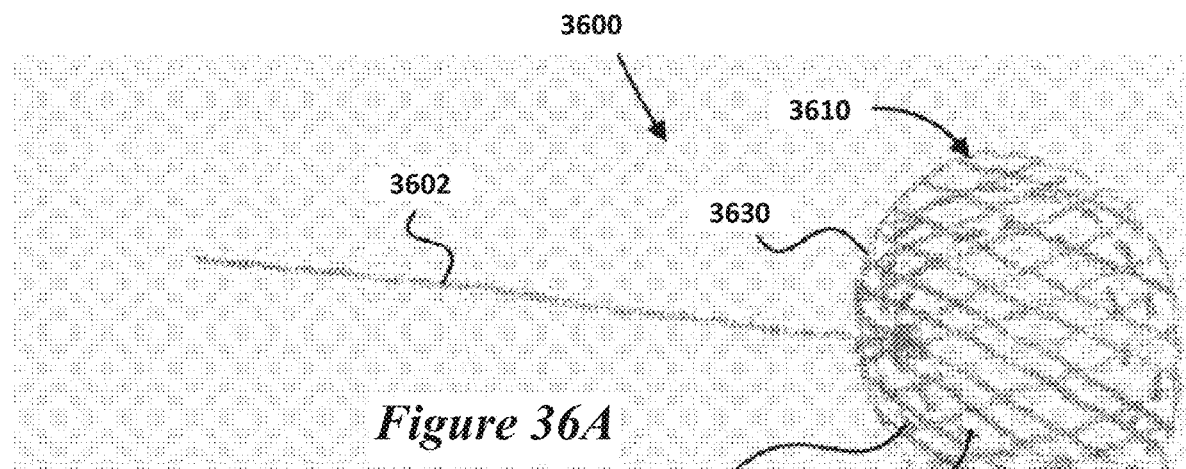
FIG. 36A is a view of a portion of a medical device in an expanded configuration, according to an embodiment.
Figure 36B:
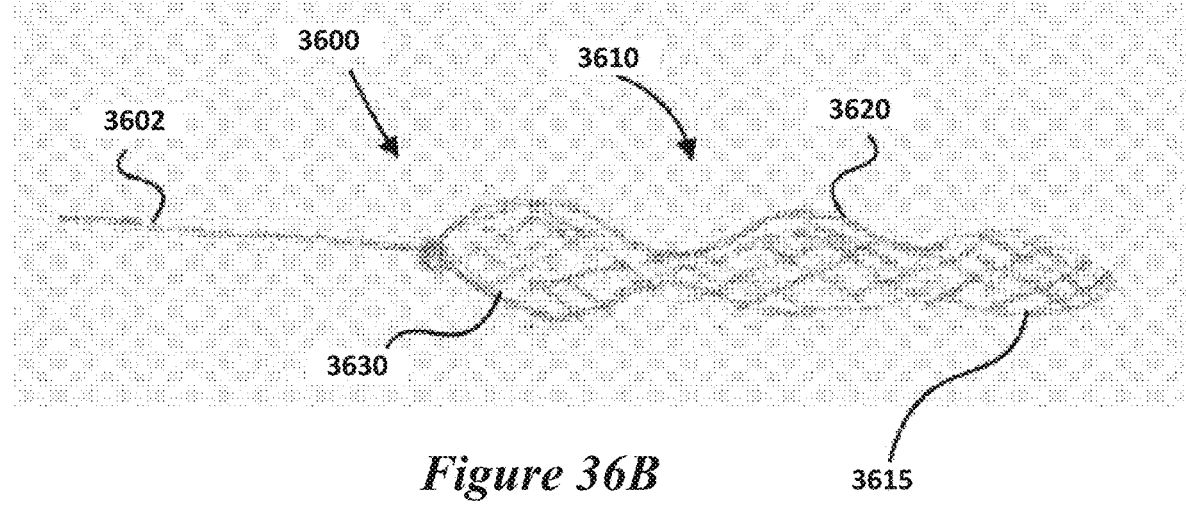
FIG. 36B is a view of a portion of the medical device of FIG. 36A in a collapsed configuration.
Figure 36C:
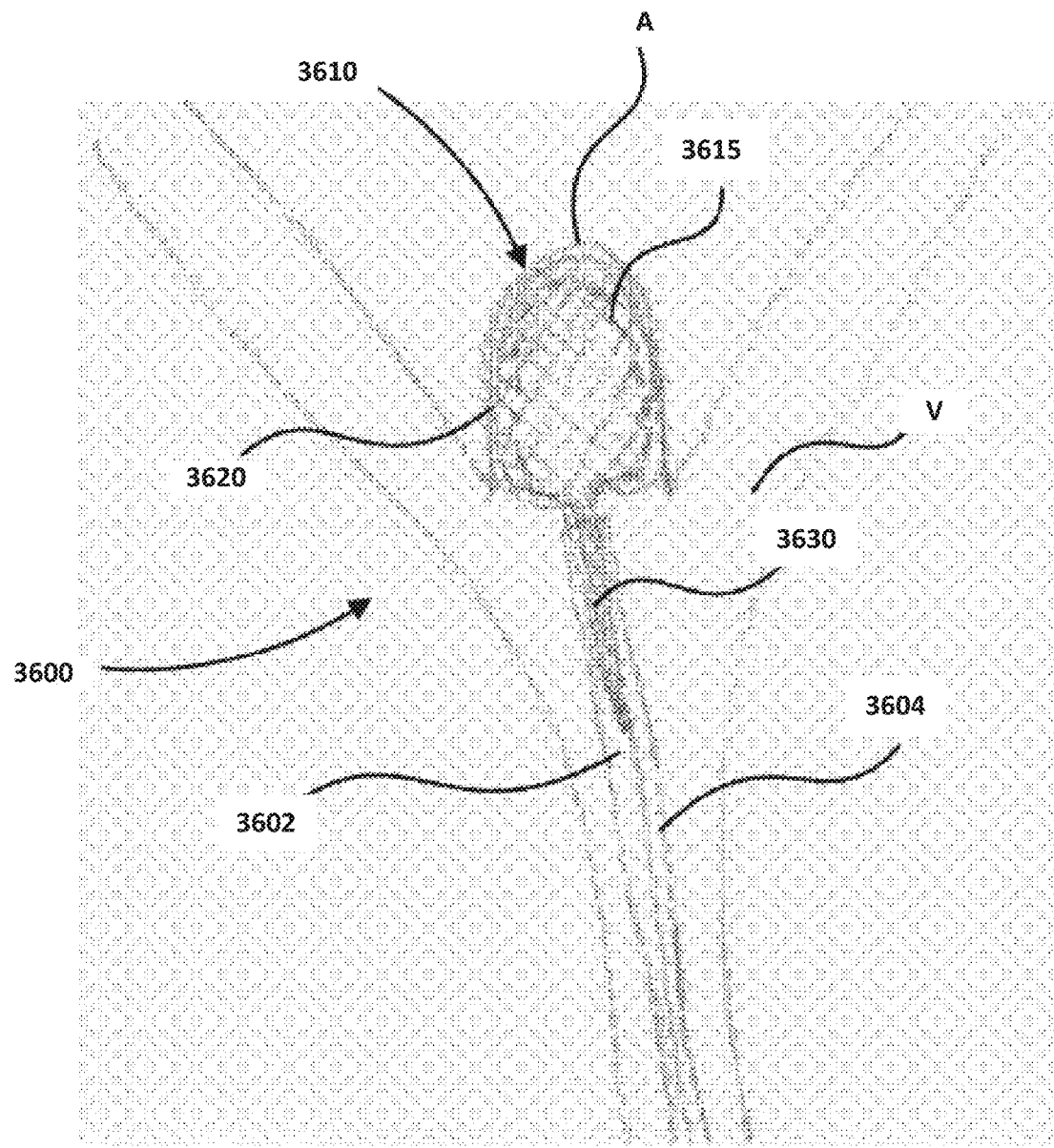
FIG. 36C is a view of a portion of the medical device of FIG. 36A shown partially deployed within an aneurysm.

FIGS. 36A-36C illustrate a portion of another embodiment of a medical device. The medical device 3600 can include the same or similar features and functions as described above for previous embodiments. For example, the medical device 3600 includes an occlusion device 3610 and an insertion portion or member 3602. The occlusion device 3610 can be moved between a collapsed configuration, as shown in FIG. 36B and an expanded configuration, as shown in FIG. 44.

The occlusion device 3610 is an example of a multi-layer implant that includes a ribbon-like strand of porous mesh that includes a first portion 3630, a second portion 3620 and a third portion 3615 formed with a single mesh component. Such an embodiment may be desirable in that the implant can fit in a small delivery catheter, but can have high flow disruption by having more than two layers of material, and forming the layers in-vivo. For example, in this embodiment, when the occlusion device 3610 is in the expanded configuration, the second portion 3620 can be expanded within the third portion 3615 and the first portion 3630 can be expanded within the second portion 3620. Specifically, during deployment within an aneurysm A, as shown in FIG. 36C, the medical device 3600 can first be inserted into a delivery catheter 3604 such that the occlusion device 3610 is moved to its collapsed configuration. At the deployment site, the occlusion device 3610 can be moved outside the delivery catheter 3604 and deployed within an aneurysm. During deployment, the third portion 3615 can be deployed first, then the second portion 3620 can be deployed within an interior region defined by the third portion 3615, and then the first portion 3630 can be deployed within an interior region defined by the second portion 3620. FIG. 36C illustrates the occlusion device 3610 with the third portion 3615 and the second portion 3620 deployed and the first portion 3630 still within the catheter 3604. In some embodiments, the insertion portion 3602 can be coupled to the second portion 3620, such that during detachment of the insertion portion 3602 (e.g., after the occlusion device 3610 has been deployed within an aneurysm), the detachment can occur inside the second portion to avoid any part of the implant from extending or hanging within the blood vessel V.

Figure 37A:
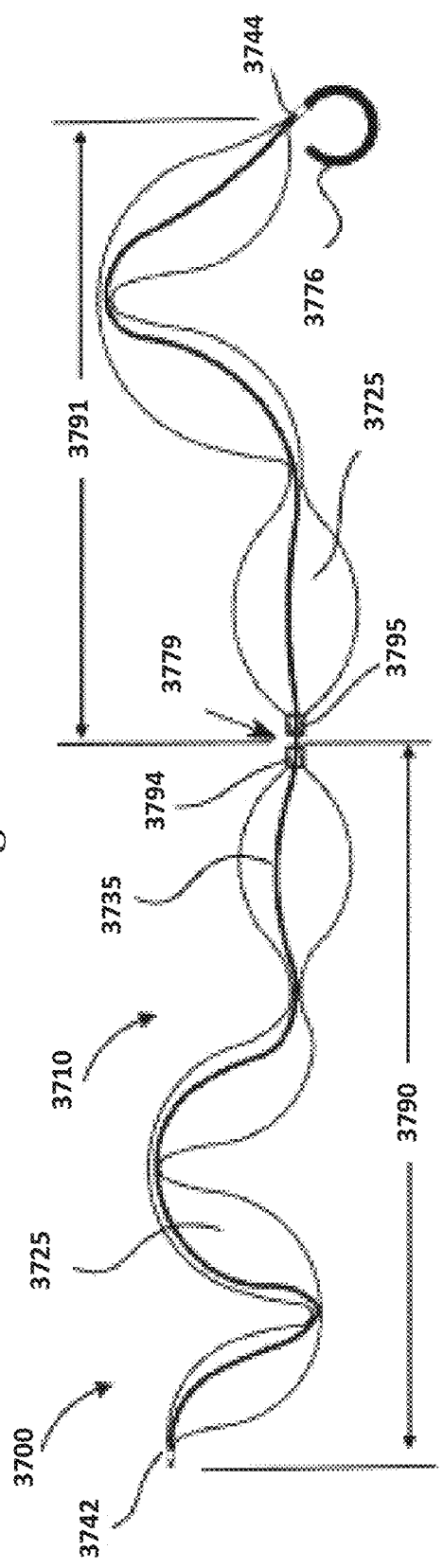
FIG. 37A is a schematic illustration of a portion of a medical device shown in a collapsed configuration, according to another embodiment.
Figure 37B:
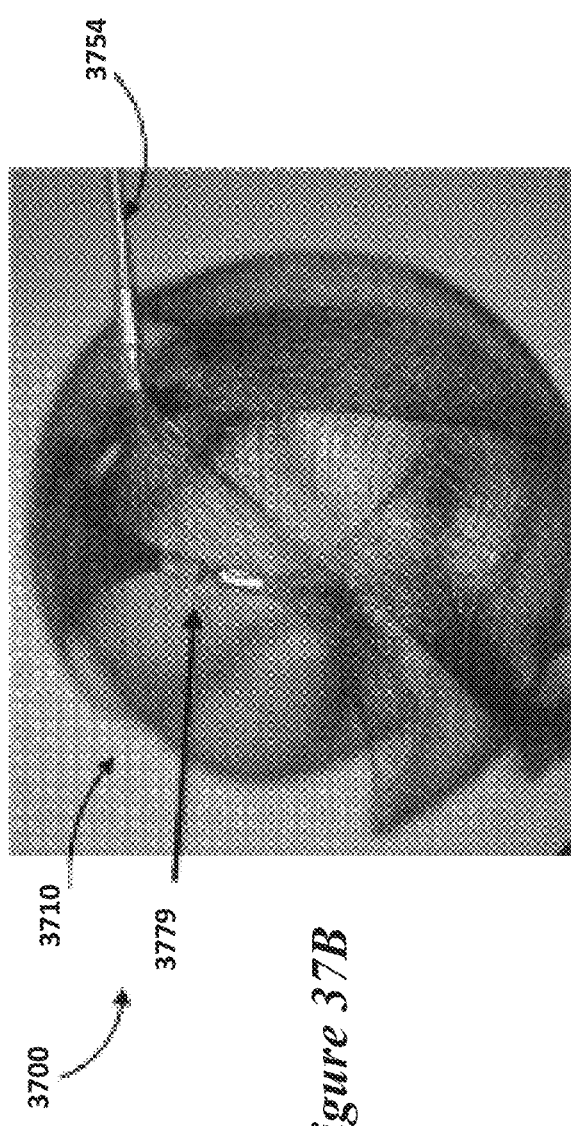
FIG. 37B is a view of the portion of the medical device of FIG. 37A, shown in an expanded configuration.
Figure 38:
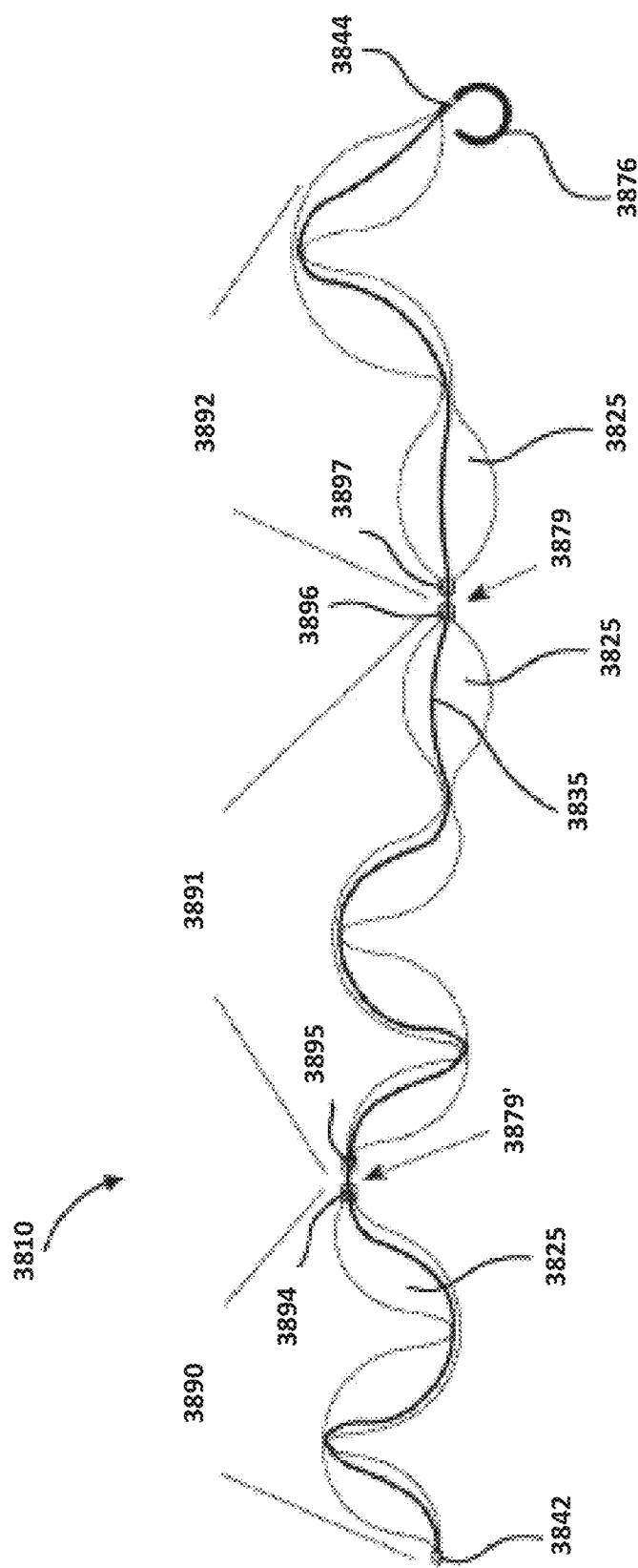
FIG. 38 is a schematic illustration of a portion of an occlusion device, according to another embodiment, shown in a collapsed configuration.

FIGS. 37A, 37B and 38 illustrate a portion of a medical device 3700 according to an embodiment. The medical device 3700 can include the same or similar features and functions as described herein for other embodiments. For example, the medical device 3700 can include an occlusion device 3710 configured to move from the collapsed configuration (e.g., for delivery through a blood vessel) to the expanded configuration (e.g., for deployment within an aneurysm) and an insertion member or device 3754 (shown in FIG. 37B) as described herein.

Similar to the occlusion device 2910, the occlusion device 3710 includes a ribbon-like strand of porous mesh that includes one or more petal-like portions or sections 3725 along its length. In this embodiment, there are four petal-like portions 3725 included within an outer petal segment 3791 of the occlusion device 3710 and three petal-like portions 3725 included within an inner petal segment 3790 of the occlusion device 3710.

At least a portion of the porous mesh can be configured to be positioned over a neck of an aneurysm when the occlusion device 3710 is in the expanded configuration. When the occlusion device 3710 is in its expanded configuration, the occlusion device 3710 has a three-dimensional shape (e.g., a substantially spherical shape) with a substantially continuous outer surface such that a portion (e.g., edges) of at least two of the petal-like portions 3725 overlap each other as shown in FIG. 37B. For example, as the occlusion device 3710 is being deployed within an aneurysm, the petal-like portions 3725 of the outer petal segment 3791 expands first and forms an outer layer that covers the aneurysm. The petal-like portions 3725 of the inner petal segment 3790 then form a second spherical layer of material inside the petal-like portions 3725 of the outer petal portion 3791 to provide greater surface area to further promote thrombosis.

In this embodiment, a suture strand 3735 extends along the length of the occlusion device 3710 to provide reinforcement to the occlusion device 3710 and can also provide for a radiopaque coil to be disposed over at least a portion of the suture strand 3735 to provide visibility of the occlusion device 3710 during, for example, fluoroscopy. As shown in FIGS. 37A and 37B, the suture strand 3735 is disposed along a length of the occlusion device 3710 and across or within the petal-like portions 3725. The suture strand 3735 can be coupled to, for example, marker bands 3742 and 3744 disposed on a proximal end and a distal end, respectively, of the occlusion device 3710.

In this embodiment, the outer petal segment 3791 and the inner petal segment 3790 can be formed as separate components and coupled together by the suture strand 3735. This creates an articulation point or joint 3779 between the outer petal segment 3791 and the inner petal segment 3790. For example, the inner petal segment 3790 can include the marker band 3742 at a proximal end and a marker band 3794 at a distal end. The outer petal segment 3791 can include the marker band 3744 at a distal end and a marker band 3795 at a proximal end. The articulation joint 3779 is defined where the marker band 3794 and the marker band 3795 are coupled to the suture strand 3735.

The articulation joint 3779 can provides greater freedom of motion of the petal-like portions 3725, which can allow more uniform expansion of the petal-like portions 3725. In 3790, the separate construction of the outer petal segment 3791 and the inner petal segment 3790 can allow for one spherical layer of the occlusion device to be formed at a time, which may be advantageous and/or easier to manufacture. The ability to manufacture the occlusion device 3710 in multiple segments can also allow for the addition to, or removal of, segments of an occlusion device to provide a selected length or size of the occlusion device to meet a particular need.

As shown in FIG. 37A, the occlusion device 3710 can also include a lead-in member 3776 coupled to a distal end portion of the occlusion device 3710 with the marker band 3744. The lead-in member 3776 can be formed with, for example a shape memory material such, as nitinol, such that the lead-in member 3776 has a biased curved shape when not constrained within, for example a cannula (not shown).

In some embodiments, the lead-in member 3776 can be coupled to the distal end portion of the occlusion device 3710 with a crimp. Although not shown, the occlusion device 3710 can also include a coupling member to releasably couple the occlusion device 3710 to the delivery device 3754 as described above for previous embodiments.

FIG. 38 illustrates another embodiment of a medical device 3800 that includes an occlusion device 3810 that has multiple articulation joints 3879. The medical device 3800 can include the same or similar features and functions as described herein for other embodiments. For example, the medical device 3800 can be configured to move from a collapsed configuration a shown in FIG. 38 (e.g., for delivery through a blood vessel) to an expanded configuration (not shown) (e.g., for deployment within an aneurysm). The medical device 3800 can also include an insertion member or device (not shown in FIG. 38) to which the occlusion device 3810 can be releasably coupled, as described above for previous embodiments.

The occlusion device 3810 includes a ribbon-like strand of porous mesh that includes one or more petal-like portions or sections 3825 along its length. In this embodiment, there are three petal-like portions 3825 included within a first petal segment 3892 of the occlusion device 3810, four petal-like portions 3825 included within a second petal segment 3891, and three petal-like portions 3825 included within a third petal segment 3890 of the occlusion device 3810.

As with the previous embodiment, at least a portion of the porous mesh can be configured to be positioned over a neck of an aneurysm when the occlusion device 3810 is in the expanded configuration. When the occlusion device 3810 is in its expanded configuration, the occlusion device 3810 can have a three-dimensional shape (e.g., a substantially spherical shape) with a substantially continuous outer surface as described above for previous embodiments.

A suture strand 3835 extends along the length of the occlusion device 3810 to provide reinforcement to the occlusion device 3810 and can also provide for a radiopaque coil to be disposed over at least a portion of the suture strand 3835 to provide visibility of the occlusion device 3810 during, for example, fluoroscopy. The suture strand 3835 can be coupled to, for example, marker bands 3842 and 3844 disposed on a proximal end and a distal end, respectively, of the occlusion device 3810.

As shown in FIG. 38, the occlusion device 3810 can also include a lead-in member 3876 coupled to a distal end portion of the occlusion device 3810 with the marker band 3844. The lead-in member 3876 can be formed the same as or similar to the lead-in members described above. Although not shown, the occlusion device 3810 can also include a coupling member to releasably couple the occlusion device 3810 to a delivery device as described above for previous embodiments.

In this embodiment, the first petal segment 3892, the second petal segment 3891 and the third petal segment 3890 can be formed as separate components and coupled together by the suture strand 3835. This creates a first articulation point or joint 3879 between the first petal segment 3892 and the second petal segment 3891, and a second articulation point or joint 3879' between the second petal segment 3891 and the third petal segment 3890. In this embodiment, the first petal segment 3892 includes the marker band 3844 on a distal end and a marker band 3897 on a proximal end, the second petal segment 3891 includes a marker band 3896 on a distal end and a marker band 3895 on a proximal end, and the third petal segment 3890 includes the marker band 3842 at a proximal end and a marker band 3894 at a distal end. The first articulation joint 3879 is defined where the marker band 3897 and the marker band 3896 are coupled to the suture strand 3835, and the second articulation joint 3879' is defined where the marker band 3895 and the marker band 3894 are couple to the suture strand 3835.

As discussed above for occlusion device 3710, the articulation joints 3879, 3879' can provide greater freedom of motion of the petal-like portions 3825 of the occlusion device 3810, which can allow more uniform expansion of the petal-like portions 3825 within an aneurysm. In addition, with three petal segments 3892, 3891, 3890, the occlusion device 3810 can have a greater density when deployed within an aneurysm which can further enhance thrombosis.

In alternative embodiments, an occlusion device can have a different number of articulation joints and a different number of petal segments than described above for occlusion devices 3710 and 3810. In sonic embodiments, it may be desirable to have at least two petal-like portions (e.g., 3725, 3825) between the articulation joints. In other words it may be desirable for each petal segment to have at least two petal-like portions. A greater number of articulation points or joints can provide increased freedom of motion of the petal-like portions, which can lead to a more uniform expansion of the occlusion device. The petal segments or layers can also have variable stiffness. For example, in an occlusion device, such as, occlusion device 3810, it may be desirable for the first petal segment to have a greater stiffness such that the first petal segment (e.g., petal segment 3892) can frame the aneurysm as the occlusion device is being deployed within the aneurysm. In this example it may be desirable for the second petal segment (e.g., petal layer 3891) to have a medium stiffness (e.g., stiffness less than the first petal segment and greater than the third petal segment) to fill the aneurysm, and the third petal segment (e.g., petal segment 3890) to be the softest segment to pack the aneurysm.

The petal width can also be varied between segments. For example, it may be desirable for the distal segment (e.g., first petal segment 3892) to have a greater width than the remaining segments and the proximal petal segments (e.g., the second petal segment 3891 and/or the third petal segment 3890) to be shorter and narrower to fit inside the distal segment (e.g., the first petal segment 3892).

Any of the occlusion devices described herein can include an outer marker band and an inner marker band coupled to a proximal end portion of the occlusion device that can be used to couple the occlusion device to an insertion device. In addition, any of the occlusion devices described herein can include a connector member (e.g., 2152, 3052, 3452) as described above, including a wire and ball member configured to be coupled to an insertion device. Further, although the ball members (insertion or implant ball members) are shown as circular, any of the ball members described herein can be other shapes, such as, for example, oval, elliptical, square, rectangular, triangular or other desired shape (as shown in a side view).

The various devices described herein can be made of any material suitable for the defined purpose, including, for example, drawn filled tube DFT®. DFT is available as wire, cable or ribbon. DFT is a metal-to-metal composite developed to combine the desired physical and mechanical attributes of two or more materials into a single wire or ribbon system, which can be used for the occlusion device.

Filaments or wires for the braid or mesh (e.g., the occlusion devices) can include, for example, filaments of materials such as MP35N, stainless steel, nitinol, cobalt chromium, titanium, platinum, tantalum, tungsten, or alloys thereof, or polyester, polyethylene (PET), Dacron, PEEK, vectron, and suture materials. Each strand may have a diameter between 0.0005"-0.010", e.g., about 0.002". In some embodiments, an outer material of the mesh or braid can be formed with nitinol that is superelastic at body temperature, and an inner material can be radiopaque, or alternatively platinum wires may be included in the braid to provide additional radiopacity. For example, in some embodiments, an occlusion device can include radiopaque material(s) woven within the mesh material such that the occlusion device can be highly visible without the use of a radioactive die.

Suitable materials can be chosen based on their electropositivity. For example, an occlusion device can include titanium, tungsten, or another material listed below in Table 1, or any combination thereof. In use, the electropositive material of the expanded occlusion device creates an electrically favorable region within the vascular defect and through the blood, and the region in the defect containing blood, fluid or tissue is then predisposed for endothelialization to occur.

TABLE 1

| PERIODIC TABLE ELEMENT | ABBREVIATION | FULL NAME | COMPOSITE CHARGE VALUE |
|---|---|---|---|
| 22 | Ti | titanium | 1.36 |
| 23 | V | vanadium | 1.53 |
| 40 | Zr | zirconium | 1.22 |
| 41 | Nb | niobium or columbium | 1.33 |
| 42 | Mo | molybdenum | 1.47 |
| 72 | Hf | hafnium | 1.16 |
| 73 | Ta | tantalum | 1.30 |
| 74 | W | tungsten | 1.47 |

In some embodiments, the occlusion devices described herein can be formed with tubular braid, or sheets of woven filaments (forming a mesh, weave or fabric). The filaments can be wire or polymer or other suitable material. The occlusion devices can be braided wire (e.g. NiTi wire), and can include a mixture of wire types and wire sizes (e.g. NiTi and Platinum wire, and e.g. 0.001" wire braided with 0.00125" wire). The occlusion devices can also be made with polymer fibers, or polymer fibers and metal wire mixed together. In some embodiments, the filaments or wires for the braid or mesh can be formed with a radiopaque material. In some embodiments, the filaments or wires for the braid or mesh can include, for example, a wire coextruded with a platinum core surrounded by nitinol (NiTi). In other words, the wire includes two concentric circles when viewed in a cross-sectional view, with the center or core wire being platinum, and the outer wire being nitinol. The percentage of platinum can be, for example, between 5% platinum to 50% platinum and several variations in between (e.g., 10%, 15%, 20%, 25%, 30%, 35%, 40%, 45%). Said another way, a percentage of a diameter of the wire can be, for example 5% to 50% platinum. In some embodiments, the percentage of platinum to nitinol is 30% platinum and 70% nitinol. In some embodiments, the occlusion devices can be formed with one or more bioabsorbable materials. In some embodiments, after the occlusion device is formed, the mesh of the implant can be etched to remove an outer oxide layer. This can provide corrosion reduction and/or help thrombosis form faster.

The occlusion devices described herein can be formed with one or more soft pliable materials such that the occlusion device can be deployed, for example, in a ruptured or unruptured aneurysm. In some embodiments an occlusion device as described herein can be formed with one or more materials such that the occlusion device has variable stiffness. For example, a first portion of the occlusion device can be formed with a first material and a second portion of the occlusion device can be formed with a second material different than the first material, or the first material can have a different thickness than the second material. For example, in some embodiments, a distal end portion of the occlusion device can be formed with a first material and a proximal end portion of the occlusion device can be formed with a second material different than the first material. In some embodiments, a proximal end portion of an occlusion device can be formed with a first material that provides for greater stiffness than a second material with which a distal end portion of the occlusion device is formed. Such an embodiment may be desirable such that the softer distal end portion of the implant can be deployed within an aneurysm and the stiffer proximal end portion can provide more structure to help support the implant at, for example, a neck of the aneurysm.

The mesh of the occlusion devices can be made by a variety of different forms, including, but not limited to, braiding, weaving, welding, or laser cutting. The mesh can have an operating length, for example, in a range of about 0.5 cm to about 70 cm. In some embodiments, the mesh can have a length of 30 cm. In some embodiments, the mesh can have a diameter in a range of about 0.5 mm-60 mm. In some embodiments, the mesh can have a diameter of up to about 10 mm when expanded (e.g., about 9.5 mm for an outer porous member or portion, about 8 mm for an inner porous member or portion). The mesh can have a single density or can have two or more densities. For example, in some embodiments, the number of variable densities can be in a range of about 2 to about 10. For example, a first density can be about 100 PPI and a second density can be about 40 PPI (PPI=pics per inch). The braid pattern can be any pattern suitable, for example, a one-over-one configuration, or two-over-one configuration, etc. Strand count for the mesh can be in a range of about 4 strands to about 288 strands. In some embodiments, the strand count is about 48 strands. Common multiples of 4, 8, 16, 24, 32, 64, 72, 96, 128, 144, 192 and 288 strands for braid are available using commercial braiders.

A single occlusion device can include wires of the same size or a combination of 2 different wire sizes. For example, the occlusion device can have 24 wires of 0.001" and 24 wires of 0.0005". The thicker wires can impart additional strength to the occlusion device and the thinner wire can provide density. In addition, any combination of wire count, wire diameter, braid angle or pics per inch can be used to make the mesh of the occlusion device.

Although the embodiments (e.g., occlusion device 2210) illustrated and described herein include one or two porous members or portions (e.g., porous members 2220, 2230), in other embodiments, any suitable number of porous members or portions can be included. For example, in some embodiments, the occlusion device 2210 can also include a third porous member (not shown) having a first end and a second end and coupled to at least one of the first porous member 2220 and the second porous member 2230. Like the first and second porous members 2220, 2230, the third porous member can have a collapsed configuration for insertion through the blood vessel and an expanded configuration for occupying the sac of the aneurysm. The third porous member can be substantially elongate and have a width in its expanded configuration that is greater than its width in its collapsed configuration.

5.0 CONCLUSION

Although many of the embodiments are described above with respect to devices, systems, and methods for treating a cerebral aneurysm, other applications and other embodiments in addition to those described herein are within the scope of the technology. For example, the occlusion devices, systems, and methods of the present technology can be used to treat any vascular defect and/or fill or partially fill any body cavity or lumen or walls thereof. Additionally, several other embodiments of the technology can have different states, components, or procedures than those described herein. For example, in some aspects of the present technology, the occlusion device 100 includes more than one mesh 101 and/or braid. In further aspects, the mesh 101 is not a braided structure. Moreover, although the proximal portion 104 of the occlusion device 100 is described herein with reference to the particular mesh configuration 101 shown in FIGS. 1A-3B, the intermediate and distal portions 106, 108 of the present technology can be used with any suitable vascular occlusion device. For example, the intermediate and distal portions 106, 108 of the present technology can be used with any of the expandable implants described with reference to FIGS. 13A-38.

It will be appreciated that specific elements, substructures, advantages, uses, and/or other features of the embodiments described with reference to FIGS. 1A-4E and 6-12 can be suitably interchanged, substituted or otherwise configured with one another in accordance with additional embodiments of the present technology. For example, the portions of the occlusion devices described with reference to FIGS. 6-12 can be combined with any of the occlusion devices shown in FIGS. 1A-4E. Furthermore, suitable elements of the embodiments described above with reference to FIGS. 1A-4E and 6-12 can be used as standalone and/or self-contained devices. A person of ordinary skill in the art, therefore, will accordingly understand that the technology can have other embodiments with additional elements, or the technology can have other embodiments without several of the features shown and described above with reference to FIGS. 1A-4E and 6-12.

We claim:

1. A vascular occlusion device for treating an aneurysm, wherein a neck of the aneurysm opens to a blood vessel, the device comprising:
    a proximal portion having a mesh configured to be positioned within the aneurysm;
    a distal portion including a directing region having:
        a proximal terminus,
        a distal terminus, and
        a length measured between the proximal terminus and the distal terminus, wherein the length of the directing region is from about 25% to about 75% of a diameter of the aneurysm; and
    an intermediate mesh portion between the proximal and distal portions that, when in a deployed configuration, forms a preset bend in the device that orients the directing region at an angle to a portion of the proximal portion adjacent the intermediate mesh portion, wherein the angle is between about 45 degrees and about 135 degrees, and
    wherein, when the device is being pushed distally out of a delivery catheter into the aneurysm, the directing region directs the distal portion to inhibit the distal portion from exiting the aneurysm through the neck such that the proximal portion crosses the neck and generally remains within the aneurysm, wherein the device is configured to be implanted within the aneurysm.

2. The device of claim 1, wherein the directing region includes an elongated, generally cylindrical mesh.

3. The device of claim 1, wherein the intermediate mesh portion includes a portion of the mesh having a preset, curved shape.

4. The device of claim 1, wherein the directing region has a generally linear shape.

5. The device of claim 1, wherein the mesh of the proximal portion is a braid.

6. The device of claim 1, wherein the length of the directing region is between about 0.05 inches and about 0.20 inches.

7. The device of claim 1, wherein the length of the directing region is between about 0.021 inches and about 0.20 inches.

8. The device of claim 1, wherein the length of the directing region is between about 0.021 inches and about 0.18 inches.

9. The device of claim 1, wherein the angle is between about 65 degrees and about 115 degrees.

10. The device of claim 1, wherein the angle is between about 70 degrees and about 110 degrees.

11. The device of claim 1, wherein the angle is between about 80 degrees and about 105 degrees.

12. A vascular occlusion device for treating an aneurysm, wherein a neck of the aneurysm opens to a blood vessel, the device comprising:

an expandable mesh having an elongated configuration and a deployed configuration, wherein, in the deployed configuration, the mesh includes:

a proximal portion formed of a braid configured to contact and conform to an inner surface of the aneurysm, a distal portion, an intermediate mesh portion extending between the proximal portion and the distal portion, wherein the intermediate mesh portion is curved such that the distal portion is positioned at a predetermined angle with respect to the proximal portion; and a directing region at the distal portion of the expandable mesh having a proximal terminus and a distal terminus, wherein the directing region extends from the proximal terminus to the distal terminus, and wherein the directing region is positioned at an angle relative to the proximal portion between about 45 degrees and about 135 degrees, and wherein, when the device is being pushed distally out of a delivery catheter into the aneurysm, the directing region directs the distal portion to inhibit the distal portion from exiting the aneurysm through the neck such that the proximal portion crosses the neck and generally remains within the aneurysm, wherein the device is configured to be implanted within the aneurysm.

13. The device of claim 12, wherein the directing region includes an elongated, generally cylindrical portion of the mesh.

14. The device of claim 12, wherein the directing region has a generally linear shape.

15. The device of claim 12, wherein the proximal portion of the mesh forms a predetermined three-dimensional structure when the mesh is in a deployed configuration.

16. The device of claim 12, wherein the proximal portion of the mesh forms a plurality of curved, broad portions that together form a three-dimensional spherical structure when the mesh is in the deployed configuration.

17. The device of claim 12, wherein, when the mesh is in the deployed configuration, the proximal portion of the mesh forms a plurality broad portions that together form a first three-dimensional structure.

18. The device of claim 12, a length of the directing region is between about 0.05 inches and about 0.20 inches.

* * * * *

UNITED STATES PATENT AND TRADEMARK OFFICE
CERTIFICATE OF CORRECTION

| | | |
|---|---|---|
| PATENT NO. | : 11,376,012 B2 | Page 1 of 1 |
| APPLICATION NO. | : 16/526706 | |
| DATED | : July 5, 2022 | |
| INVENTOR(S) | : Aboytes et al. | |

It is certified that error appears in the above-identified patent and that said Letters Patent is hereby corrected as shown below:

On the Title Page

Item (54), in Column 1, in "Title", Line 1, after "FOR" insert -- THE --.

In the Specification

In Column 1, Line 1, after "FOR" insert -- THE --.

In the Claims

In Column 42, in Claim 18, Line 38, delete "a length" and insert -- wherein the length --, therefor.

Signed and Sealed this
Twenty-fifth Day of October, 2022

*Katherine Kelly Vidal*

Katherine Kelly Vidal
*Director of the United States Patent and Trademark Office*